(12) United States Patent
Jin et al.

(10) Patent No.: US 9,669,003 B2
(45) Date of Patent: Jun. 6, 2017

(54) USE OF FLAVONE AND FLAVANONE DERIVATIVES IN PREPARATION OF SEDATIVE AND HYPNOTIC DRUGS

(76) Inventors: Yongri Jin, Changchun (CN); Dayun Sui, Changchun (CN); Xuwen Li, Changchun (CN); Xiaofeng Yu, Changchun (CN); Mingyu Gui, Changchun (CN)

( * ) Notice: Subject to any disclaimer, the term of this patent is extended or adjusted under 35 U.S.C. 154(b) by 0 days.

(21) Appl. No.: 14/407,294

(22) PCT Filed: Jun. 13, 2012

(86) PCT No.: PCT/CN2012/076816
§ 371 (c)(1),
(2), (4) Date: Mar. 23, 2015

(87) PCT Pub. No.: WO2013/185301
PCT Pub. Date: Dec. 19, 2013

(65) Prior Publication Data
US 2015/0196529 A1    Jul. 16, 2015

(51) Int. Cl.
| A61K 31/353 | (2006.01) |
| A61K 31/352 | (2006.01) |
| C07D 311/30 | (2006.01) |
| C07D 405/04 | (2006.01) |
| C07D 405/10 | (2006.01) |
| C07D 409/04 | (2006.01) |
| C07D 409/10 | (2006.01) |
| C07D 409/14 | (2006.01) |

(52) U.S. Cl.
CPC ......... *A61K 31/353* (2013.01); *A61K 31/352* (2013.01); *C07D 311/30* (2013.01); *C07D 405/04* (2013.01); *C07D 405/10* (2013.01); *C07D 409/04* (2013.01); *C07D 409/10* (2013.01); *C07D 409/14* (2013.01)

(58) Field of Classification Search
CPC .. A61K 31/353; A61K 31/352; C07D 405/10; C07D 409/04; C07D 405/04; C07D 409/14; C07D 409/10; C07D 311/30
See application file for complete search history.

(56) References Cited

FOREIGN PATENT DOCUMENTS

WO    WO 03/061678 A1    7/2003

OTHER PUBLICATIONS

Wolff, Some consideration for prodrug design, Burger's Medicinal Chemistry and Drug Discovery, $5^{th}$ Edition, vol. 1, pp. 975-977, 1995.*
Banker et al, Prodrug, Modern Pharmaceutics, $3^{rd}$ Edition, pp. 451 and 596, 1996, Modern Pharmaceutics.*
Cho et al., "Hypnotic effects and GABAergic mechanism of licorice Glycyrrhiza glabra) ethanol extract and its major flavonoid constituent glabrol", Bioorganic & Medicinal Chemistry, Apr. 11, 2012, 20, 11, pp. 3493-3501.
Karim et al., "2'-methoxy-6-methylflavone: a novel anxiolytic and sedative with subtype selective activating and modulating actions at GABAA receptors", British Journal of Pharmacology, Feb. 2012, 165, 4, 880-896.
Peng, "Isolation and purification of flavones from Murraya exotica L by high-speed counter-current chromatography", Chinese Master's Theses Full-text Database, Medicine and Health Sciences, Apr. 15, 2011, 4.
Shi et al., "Effect of citrus reticulata blanco extract on sleep function and spontaneous activity in mice", Zhongguo Iinchuang kangfu, Jun. 28, 2005, 9, 24, 116, 117.
Shrestha et al., "Rhus parviflora and its biflavonoid constituent, rhusflavone, induce sleep through the positive allosteric modulation of GABAA-benzodiazepine receptors", Journal of Ethnopharmacology, May 2, 2012, 142, 1, pp. 213-220.
Viola et al., :Sedative and hypnotic properties of Salvia guaranitica and of its active principle, Cirsiliol, Phytomedicine, 1997, vol. 4, 1 pp. 47-51.
Wang, "Studies on flavonoids from leaves of Murraya exotica L.", Chinese Master's Theses Full-text Database, Medicine and Health Sciences, Sep. 15, 2007, 3.
Wolfman et al., "Anxioselective properties of 6, 3'-dinitroflavone, a high-affinity benzodiazepine receptor ligand", European Journal of Pharmacology, 1996, 318, 1, pp. 23-30.
Zanoli et al., "Behavioral characterization of the flavonoids apigenin and chrysin", Fitoterapia, 2000, 71, Suppl. 1, pp. S117-S123.

* cited by examiner

*Primary Examiner* — Sudhakar Katakam
(74) *Attorney, Agent, or Firm* — Birch, Stewart, Kolasch & Birch, LLP

(57) ABSTRACT

Disclosed is a use of flavones derivatives and flavanone derivatives in preparation of sedative and hypnotic drugs.

8 Claims, No Drawings

USE OF FLAVONE AND FLAVANONE DERIVATIVES IN PREPARATION OF SEDATIVE AND HYPNOTIC DRUGS

TECHNICAL FIELDS

Embodiments of the present invention are directed to new bioactivities and medical uses of flavones derivatives and flavanone derivatives, and more particularly, embodiments of the present invention are directed to the inhibiting effects on central nervous system and bioactivities in sedation and hypnosis of flavones and flavanone derivatives, and uses of the same in the preparation of sedative and hypnotic drugs.

BACKGROUNDS

As one of the most common clinic symptoms, insomnia is an originating and continuous disorder of sleep, rendering the sleep quality insufficient for normal physiological requirements of human body, thereby affecting the usual activities of patients, causing sleep disorder syndrome with symptoms like weariness, attention deficit and lags in response.

Hypnotic drugs are drugs which help people to sleep, and ideal requirements on this class of drugs include: (1) reducing the time to fall asleep, i.e., reducing sleep induction period; (2) elongating sleeping time and increasing the depth of sleep; (3) the ratio of slow wave sleep phase and rapid eye movement phase remaining unchanged. Sedative and hypnotic drugs may be screened on the basis of the mechanism of sedation and hypnosis, and may also be screened via animal model means.

Screening sedative and hypnotic drugs via animal model means may suffer from heavy workload, long time, high costs and unclear sedative and hypnotic working mechanism, but the experimental results of the same is more reliable.

Currently, animal models and methods for screening sedative and hypnotic drugs include: (1) general behavior observation; (2) voluntary action observation; (3) elongation of the sleep time under pentobarbital sodium; (4) experimentations with pentobarbital sodium doses below the threshold; (5) Wake up to bed experiments with pentobarbital sodium.

The tested drug is proved to be effective in sedation and hypnosis if the following phenomena are observed: (1) voluntary actions of the mice significantly decrease; (2) the time of sleep caused by pentobarbital sodium increases, and the number of mice increases for which are administered pentobarbital sodium below the threshold and fall into sleep, or the mice go back to sleep for which have been administered pentobarbital sodium and wake up subsequently. In the above animal experiments, it is generally required to employ two doses for the tested drug.

Currently, both western medicine and Chinese traditional medicine are used for treating insomnia. Although western medicine has advantages of rapid onset and outstanding efficiency, it may bring prominent toxicity and side effects, and may easily cause drug resistance and drug dependence. Chinese traditional medicine has lower toxicity and side effects, unlikely brings drug resistance and drug dependence, however, it has slow onset and the effect thereof is not as significant as western medicine. Therefore, currently there are still demands for developing drugs for treating insomnia with good therapeutic effects, low toxicity and little side effects.

SUMMARY OF THE INVENTION

Embodiments of this invention provides use of flavone derivatives shown by the structure in Formula (I) or flavanone derivatives shown by the structure in Formula (II), pre-drugs, metabolites, isomers, pharmaceutically accepted salts in the preparation of sedative and hypnotic drugs.

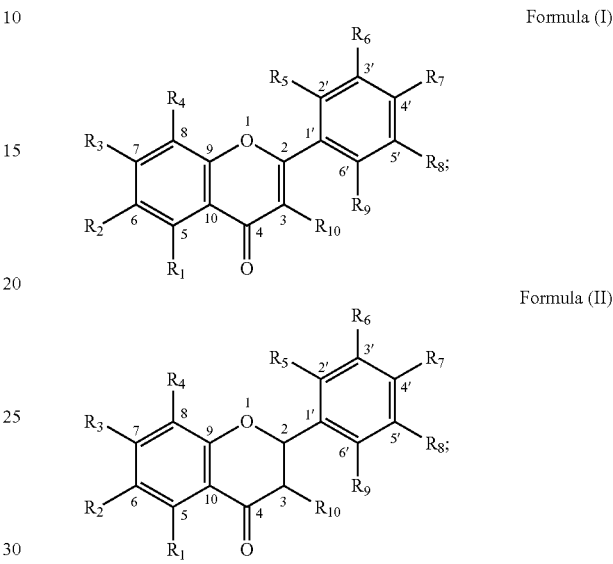

Wherein $R_1$, $R_2$, $R_3$, $R_4$, $R_5$, $R_6$, $R_7$, $R_8$, $R_9$ and $R_{10}$ may be same or different, and they may be any one independently selected from hydrogen (—H), nitro group (—NO$_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group, wherein:

the halogen may be any one of fluoride (—F), chloride (—Cl), bromide (—Br) and iodide (—I);

the alkoxy group or substituted alkoxy group has a structure Formula (1):

In Formula (1), $R_{11}$ is an alkyl group or substituted alkyl group, and it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{11}$ is branched alkyl group, straight chain alkyl group, substituted branched alkyl group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{11}$ is a cycloalkyl group or substituted cycloalkyl group, it is preferably a C3-C8 alkyl group, and more preferably a C3-C6 alkyl group; when $R_{11}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{11}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the alkoxy group or substituted alkoxy group may be methoxy group, ethoxy group, amoxy group, undecyloxy group, and the like.

The alkyl group or substituted alkyl group may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when it is branched alkyl group, straight chain alkyl group, substituted branched alkyl group or substituted straight chain alkyl group, it is preferably a C1-C25 alkyl group, more preferably a C2-C18 alkyl group, most preferably a C4-C16 alkyl group, and particularly most preferably a C8-C15 alkyl group; when it is a cycloalkyl group or substituted cycloalkyl group, it is preferably a C3-C8 alkyl group, and more preferably a C4-C6 alkyl group; when it is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when it is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the alkyl group or substituted alkyl group may be chloro-pentyl group, chloromethyl group, sulfonic butyl group, benzyl group, amino methyl group, ethyl group, eicosyl group, and the like.

The alkynyl group or substituted alkynyl group has a structure of Formula (2):

$$R_{12}-C\equiv C-\qquad\text{Formula (2);}$$

In Formula (2), $R_{12}$ is one of hydrogen, alkyl group, substituted alkyl group, phenyl group and substituted phenyl group; when $R_{12}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{12}$ is branched alkyl group, straight chain alkyl group, substituted branched alkyl group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{12}$ is a cycloalkyl group or substituted cycloalkyl group, it is preferably a C3-C8 alkyl group, and more preferably a C3-C6 alkyl group; when $R_{12}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{12}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; when $R_{12}$ is a substituted phenyl group, the substitution group thereof may be one or more of nitro group, halogen, hydroxyl group, carboxyl group, amino group, and sulfonic group; particularly, the alkynyl group or substituted alkynyl group may be phenylethynyl group, ethynyl group and the like.

The alkenyl group or substituted alkenyl group has a structure of Formula (3):

$$R_{13}-C\equiv C-\qquad\text{Formula (3);}$$

In Formula (3), $R_{13}$ is one of hydrogen, alkyl group, substituted alkyl group, phenyl group and substituted phenyl group; when $R_{13}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{13}$ is branched alkyl group, straight chain alkyl group, substituted branched alkyl group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{13}$ is a cycloalkyl group or substituted cycloalkyl group, it is preferably a C3-C8 alkyl group, and more preferably a C3-C6 alkyl group; when $R_{13}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{13}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; when $R_{13}$ is a substituted phenyl group, the substitution group thereof may be one or more of nitro group, halogen, hydroxyl group, carboxyl group, amino group, and sulfonic group; particularly, the alkenyl group or substituted alkenyl group may be butenyl group, ethenyl group, pentenyl group, chloro-pentenyl group and the like.

The amide group has a structure of Formula (4) or a structure of Formula (5):

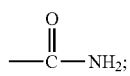

Formula (4)

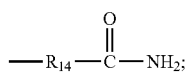

Formula (5)

In Formula (5), $R_{14}$ is an alkyl group or substituted alkyl group, and may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{14}$ is branched alkyl group, straight chain alkyl group, substituted branched alkyl group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{14}$ is a cycloalkyl group or substituted cycloalkyl group, it is preferably a C3-C8 alkyl group, and more preferably a C3-C6 alkyl group; when $R_{14}$ is a heterocyclic alkyl group or substituted heterocyclic alkyl group, the heteroatom may be one or more of S, O, N and so on, and the number of carbon atoms in the heterocyclic alkyl group is preferably 3-8, and more preferably 3-6; when $R_{14}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the amide group may be —$CONH_2$, —$C_5H_{10}CONH_2$, and the like.

The aryl group or substituted aryl group is a substitution group having an aromatic group, such as phenyl group, substituted phenyl group, polycyclic aryl group, substituted polycyclic aryl group, associated aryl group or substituted associated aryl group, and the like, preferably, it is phenyl group or substituted phenyl group; in embodiments of the present invention, the number of carbon atoms in the aryl group or substituted aryl group is preferably 6-50, more preferably 6-40; particularly, when it is a polycyclic aryl group or substituted polycyclic aryl group, the number of carbon atoms is preferably 10-22, and more preferably 10-18; when it is an associated aryl group or substituted associated aryl group, the number of carbon atoms is preferably 12-30, and more preferably 12-24. When it is substituted phenyl group, substituted polycyclic aryl group or substituted associated aryl group, the substitution group thereof may be one or more of nitro group, halogen, hydroxyl group, carboxyl group, amino group, sulfonic group, phenyl group and substituted phenyl group; particularly, the aryl group or substituted aryl group may be phenyl group or chloro-phenyl group.

The carbonic ester group has a structure in Formula (6):

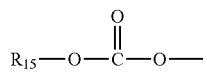

Formula (6)

In Formula (6), when $R_{15}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{15}$ is branched alkyl group, straight chain alkyl group, substituted branched group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{15}$ is a cycloalkyl group or substituted cycloalkyl group, it is preferably a C3-C8 alkyl group, and more preferably a C3-C6 alkyl group; when $R_{15}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{15}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the carbonic ester group may be $CH_3OCOO$—, $C_{15}H_{31}OCOO$—, and the like.

The ester group has a structure of Formula (7):

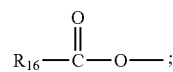

Formula (7)

In Formula (7), when $R_{16}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{16}$ is branched alkyl group, straight chain alkyl group, substituted branched group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{16}$ is a cycloalkyl group or substituted cycloalkyl group, it is preferably a C3-C8 alkyl group, and more preferably a C3-C6 alkyl group; when $R_{16}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{16}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the ester group may be $C_{10}H_{21}COO$—, and the like.

The acyl group has a structure of Formula (8):

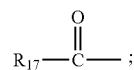

Formula (8)

In Formula (8), when $R_{17}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{17}$ is branched alkyl group, straight chain alkyl group, substituted branched group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{17}$ is a cycloalkyl group or substituted cycloalkyl group, it is preferably a C3-C8 alkyl group, and more preferably a C3-C6 alkyl group; when $R_{17}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{17}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the acyl group may be $C_5H_{11}CO$—, and the like.

The thioether group has a structure of Formula (9):

$$R_{18}\text{—}S\text{—} \quad \text{Formula (9);}$$

In Formula (9), $R_{18}$ is one of alkyl group, substituted alkyl group, alkenyl group, substituted alkenyl group, alkynyl group, substituted alkynyl, phenyl group and substituted phenyl group; when $R_{18}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{18}$ is branched alkyl group, straight chain alkyl group, substituted branched group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{18}$ is a cycloalkyl group or substituted cycloalkyl group, it is preferably a C3-C8 alkyl group, and more preferably a C3-C6 alkyl group; when $R_{18}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{18}$ is a alkynyl group or a substituted alkynyl group, it is preferably a C1-C25 alkynyl group, more preferably a C2-C18 alkynyl group, most preferably a C4-C16 alkynyl group, and particularly most preferably a C8-C15 alkynyl group; when $R_{18}$ is a alkenyl group or a substituted alkenyl group, it is preferably a C1-C25 alkenyl group, more preferably a C2-C18 alkenyl group, most preferably a C4-C16 alkenyl group, and particularly most preferably a C8-C15 alkenyl group; when $R_{18}$ is a substituted alkyl group, substituted alkynyl group or substituted alkenyl group, the substitution group thereof may be one or more of nitro group, halogen, hydroxyl group, carboxyl group, amino group, sulfonic group, phenyl group and substituted phenyl group; when $R_{18}$ is a substituted phenyl group, the substitution group thereof may be one or more of nitro group, halogen, hydroxyl group, carboxyl group, amino group and sulfonic group; particularly, the thioether group may be $C_4H_7S\text{—}$, $C_8H_{17}S\text{—}$, $BrNO_2C_{15}H_{29}S\text{—}$, and the like.

The sulfonyl group has a structure of Formula (10):

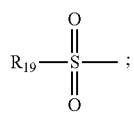

Formula (10)

In Formula (10), when $R_{19}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{19}$ is branched alkyl group, straight chain alkyl group, substituted branched group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{19}$ is a cycloalkyl group or substituted cycloalkyl group, it is preferably a C3-C8 alkyl group, and more preferably a C3-C6 alkyl group; when $R_{19}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{19}$ is a substituted branched alkyl group, substituted straight chain alkyl group, substituted cycloalkyl group or substituted heterocyclic alkyl group, the substitution group thereof may be one or more of nitro group, halogen, hydroxyl group, carboxyl group, amino group, sulfonic group, phenyl group and substituted phenyl group; particularly, the sulfonyl group may be $C_4H_9SO_2\text{—}$, $C_{11}H_{21}SO_2\text{—}$, and the like.

The group including a carbon-nitrogen double bond has a structure of Formula (11):

$$R_{20}\text{—}C\text{=}N\text{—} \quad \text{Formula (11);}$$

In Formula (11), $R_{20}$ is one of alkyl group, substituted alkyl group, alkenyl group, substituted alkenyl group, alkynyl group, substituted alkynyl, phenyl group and substituted phenyl group; when $R_{20}$ is alkyl group or substituted alkyl group, it may be branched alkyl group, straight chain alkyl group, cycloalkyl group, heterocyclic alkyl group, substituted branched alkyl group, substituted straight chain alkyl group, substituted cycloalkyl group or substituted heterocyclic alkyl group; when $R_{20}$ is branched alkyl group, straight chain alkyl group, substituted branched group or substituted straight chain alkyl group, it is preferably a C1-C25 alkyl group, more preferably a C2-C18 alkyl group, most preferably a C4-C16 alkyl group, and particularly most preferably a C8-C15 alkyl group; when $R_{20}$ is a cycloalkyl group or substituted cycloalkyl group, it is preferably a C3-C8 alkyl group, and more preferably a C3-C6 alkyl group; when $R_{20}$ is a heterocyclic alkyl group or substituted heterocyclic alkyl group, the heteroatom may be one or more of S, O and N and so on, and the number of carbon atoms in the heterocyclic alkyl group is preferably 3-8, and more preferably 3-6; when $R_{20}$ is a alkynyl group or a substituted alkynyl group, it is preferably a C1-C25 alkynyl group, more preferably a C2-C18 alkynyl group, most preferably a C4-C16 alkynyl group, and particularly most preferably a C8-C15 alkynyl group; when $R_{20}$ is a alkenyl group or a substituted alkenyl group, it is preferably a C1-C25 alkenyl group, more preferably a C2-C18 alkenyl group, most preferably a C4-C16 alkenyl group, and particularly most preferably a C8-C15 alkenyl group; when $R_{20}$ is a substituted branched alkyl group, substituted alkynyl group or substituted alkenyl group, the substitution group thereof may be one or more of nitro group, halogen, hydroxyl group, carboxyl group, amino group, sulfonic group, phenyl group and substituted phenyl group; when $R_{20}$ is a substituted phenyl group, the substitution group thereof may be one or more of nitro group, halogen, hydroxyl group, carboxyl group, amino group and sulfonic group; particularly, the group including a carbon-nitrogen double bond may be $C_4H_6N\text{—}$, and the like.

The aryloxy group or substituted aryloxy group has a structure of Formula (12):

$$R_{21}\text{—}O\text{—} \quad \text{Formula (12);}$$

In Formula (12), $R_{21}$ is aryl group or substituted aryl group, such as phenyl group, substituted phenyl group, polycyclic aryl group, substituted polycyclic aryl group, associated aryl group or substituted associated aryl group, and the like, preferably, it is phenyl group or substituted phenyl group; in embodiments of the present invention, the number of carbon atoms in $R_{21}$ is preferably 6-50, more preferably 6-40; particularly, when it is a polycyclic aryl group or substituted polycyclic aryl group, the number of carbon atoms is preferably 10-22, and more preferably 10-18; when it is an associated aryl group or substituted associated aryl group, the number of carbon atoms is preferably 12-30, and more preferably 12-24. When it is substituted phenyl group, substituted polycyclic aryl group or substituted associated aryl group, the substitution group thereof may be one or more of nitro group, halogen, hydroxyl group, carboxyl group, amino group, and sulfonic group; particularly, the aryloxy group or substituted aryloxy group may be phenoxy group or chloro-phenoxy group and so on.

In embodiments of the present invention, none of $R_1 \sim R_{10}$ is $-RCF_2R'$, wherein R represents oxygen, sulfur, halogen, alkyl group, alkenyl group, alkynyl group, phenyl group, aralkyl group or hydroxyl group, and R' represents hydrogen, oxygen, sulfur, halogen, alkyl group, alkenyl group, alkynyl group, phenyl group, aralkyl group or hydroxyl group.

Furthermore, said $R_1$, $R_2$, $R_3$, $R_4$, $R_5$, $R_6$, $R_7$, $R_8$, $R_9$ and $R_{10}$ may be the same or different, and they may be independently selected from hydrogen, nitro group, halogen, cyano group, hydroxyl group, thiocyanate group, carboxyl group, amino group, C1~C25 alkoxy group or substituted alkoxy group, C1~C25 alkyl group or substituted alkyl group, C1~C25 alkynyl group or substituted alkynyl group, C1~C25 alkenyl group or substituted alkenyl group, C1~C25 alkyl amide group, phenyl group or substituted phenyl group, C1~C25 alkyl carbonic ester group, C1~C25 alkyl ester group, C1~C25 alkyl acyl group, C1~C25 alkyl thioether group, C1~C25 alkyl sulfonic group, phenoxy group or substituted phenoxy group.

Furthermore, at least one of $R_1$, $R_2$, $R_3$, $R_4$, $R_5$, $R_6$, $R_7$, $R_8$, $R_9$ and $R_{10}$ is not hydrogen; furthermore, at least two of $R_1$, $R_2$, $R_3$, $R_4$, $R_5$, $R_6$, $R_7$, $R_8$, $R_9$ and $R_{10}$ are not hydrogen; furthermore, at least three of $R_1$, $R_2$, $R_3$, $R_4$, $R_5$, $R_6$, $R_7$, $R_8$, $R_9$ and $R_{10}$ are not hydrogen; furthermore, at least four of $R_1$, $R_2$, $R_3$, $R_4$, $R_5$, $R_6$, $R_7$, $R_8$, $R_9$ and $R_{10}$ are not hydrogen; furthermore, at least five of $R_1$, $R_2$, $R_3$, $R_4$, $R_5$, $R_6$, $R_7$, $R_8$, $R_9$ and $R_{10}$ are not hydrogen; furthermore, at least six of $R_1$, $R_2$, $R_3$, $R_4$, $R_5$, $R_6$, $R_7$, $R_8$, $R_9$ and $R_{10}$ are not hydrogen; furthermore, at least seven of $R_1$, $R_2$, $R_3$, $R_4$, $R_5$, $R_6$, $R_7$, $R_8$, $R_9$ and $R_{10}$ are not hydrogen; furthermore, at least eight of $R_1$, $R_2$, $R_3$, $R_4$, $R_5$, $R_6$, $R_7$, $R_8$, $R_9$ and $R_{10}$ are not hydrogen; furthermore, at least nine of $R_1$, $R_2$, $R_3$, $R_4$, $R_5$, $R_6$, $R_7$, $R_8$, $R_9$ and $R_{10}$ are not hydrogen; furthermore, none of $R_1$, $R_2$, $R_3$, $R_4$, $R_5$, $R_6$, $R_7$, $R_8$, $R_9$ and $R_{10}$ is hydrogen.

Furthermore, 2 or more of $R_1$, $R_2$, $R_3$, $R_4$, $R_5$, $R_6$, $R_7$, $R_8$, $R_9$ and $R_{10}$ are alkoxy groups; furthermore, 3 or more of $R_1$, $R_2$, $R_3$, $R_4$, $R_5$, $R_6$, $R_7$, $R_8$, $R_9$ and $R_{10}$ are alkoxy groups; furthermore, 4 or more of $R_1$, $R_2$, $R_3$, $R_4$, $R_5$, $R_6$, $R_7$, $R_8$, $R_9$ and $R_{10}$ are alkoxy groups; furthermore, 5 or more of $R_1$, $R_2$, $R_3$, $R_4$, $R_5$, $R_6$, $R_7$, $R_8$, $R_9$ and $R_{10}$ are alkoxy groups; furthermore, 6 or more of $R_1$, $R_2$, $R_3$, $R_4$, $R_5$, $R_6$, $R_7$, $R_8$, $R_9$ and $R_{10}$ are alkoxy groups; furthermore, 7 or more of $R_1$, $R_2$, $R_3$, $R_4$, $R_5$, $R_6$, $R_7$, $R_8$, $R_9$ and $R_{10}$ are alkoxy groups; furthermore, 8 or more of $R_1$, $R_2$, $R_3$, $R_4$, $R_5$, $R_6$, $R_7$, $R_8$, $R_9$ and $R_{10}$ are alkoxy groups; furthermore, 9 or more of $R_1$, $R_2$, $R_3$, $R_4$, $R_5$, $R_6$, $R_7$, $R_8$, $R_9$ and $R_{10}$ are alkoxy groups; furthermore, all of $R_1$, $R_2$, $R_3$, $R_4$, $R_5$, $R_6$, $R_7$, $R_8$, $R_9$ and $R_{10}$ are alkoxy groups.

Furthermore, 2 or more of $R_1$, $R_2$, $R_3$, $R_4$, $R_5$, $R_6$, $R_7$, $R_8$, $R_9$ and $R_{10}$ are methoxy groups; furthermore, 3 or more of $R_1$, $R_2$, $R_3$, $R_4$, $R_5$, $R_6$, $R_7$, $R_8$, $R_9$ and $R_{10}$ are methoxy groups; furthermore, 4 or more of $R_1$, $R_2$, $R_3$, $R_4$, $R_5$, $R_6$, $R_7$, $R_8$, $R_9$ and $R_{10}$ are methoxy groups; furthermore, 5 or more of $R_1$, $R_2$, $R_3$, $R_4$, $R_5$, $R_6$, $R_7$, $R_8$, $R_9$ and $R_{10}$ are methoxy groups; furthermore, 6 or more of $R_1$, $R_2$, $R_3$, $R_4$, $R_5$, $R_6$, $R_7$, $R_8$, $R_9$ and $R_{10}$ are methoxy groups; furthermore, 7 or more of $R_1$, $R_2$, $R_3$, $R_4$, $R_5$, $R_6$, $R_7$, $R_8$, $R_9$ and $R_{10}$ are methoxy groups; furthermore, 8 or more of $R_1$, $R_2$, $R_3$, $R_4$, $R_5$, $R_6$, $R_7$, $R_8$, $R_9$ and $R_{10}$ are methoxy groups; furthermore, 9 or more of $R_1$, $R_2$, $R_3$, $R_4$, $R_5$, $R_6$, $R_7$, $R_8$, $R_9$ and $R_{10}$ are methoxy groups; furthermore, all of $R_1$, $R_2$, $R_3$, $R_4$, $R_5$, $R_6$, $R_7$, $R_8$, $R_9$ and $R_{10}$ are methoxy groups.

Furthermore, $R_{10}$ is hydrogen, hydroxyl group or methoxy group.

In embodiments of the present invention, the flavone derivatives represented by the structure of formula (I) or the flavanone derivatives represented by the structure of formula (II) include, but are not limited within the compounds shown in Table 1:

TABLE 1

Specific examples of the flavone derivatives and flavanone derivatives provided in embodiments of the present invention.

| No. | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 1 | —OCH$_3$ | —OCH$_3$ | —OCH$_3$ | —OCH$_3$ | —OCH$_3$ | —OCH$_3$ | —OCH$_3$ | —OCH$_3$ | —OCH$_3$ | —OCH$_3$ |
| 2 | —H | —C$_5$H$_{10}$Cl | —NO$_2$ | —C$_6$H$_5$CC— | —F | —CH$_2$Cl | —CN | —OH | —C$_{20}$H$_{41}$ | —C$_3$H$_5$ |
| 3 | —F | —H | —SCN | —NO$_2$ | —C$_6$H$_5$ | —COOH | —CH$_2$Cl | —CN | —OH | —C$_4$H$_7$ |
| 4 | —NO$_2$ | —OCH$_3$ | —H | —C$_4$H$_7$S | —NO$_2$ | —C$_6$H$_5$CC— | —F | —CH$_2$Cl | —CN | —OH |
| 5 | —CN | —C$_4$H$_7$S | —NO$_2$ | —H | —C$_5$H$_{10}$Cl | —C$_5$H$_{10}$Cl | —C$_6$H$_5$CC— | —CH$_2$CH— | —C$_7$H$_{15}$CHCH— | —CN |
| 6 | —SCN | —NH$_2$CO | —H | —FC$_6$H$_4$CH$_2$— | —H | —C$_5$H$_{10}$Cl | —C$_7$H$_{15}$ | —CCH | —CH$_3$CH$_2$O— | —OH |
| 7 | —OH | —C$_6$H$_5$CC— | —I | —CH$_2$Cl | —CN | —F | —C$_5$H$_{10}$Cl | —NO$_2$ | —C$_4$H$_8$N— | C$_5$H$_{11}$O— |
| 8 | —CH$_2$Cl | —CN | —OH | —C$_{20}$H$_{40}$Cl | —C$_3$H$_5$ | —CH$_2$Cl | —H | —FC$_6$H$_4$CH$_2$— | —NH$_2$CO | —NH$_2$CO |
| 9 | —CH$_3$C(CH$_3$)$_2$ | —C$_4$H$_7$S | —NO$_2$ | —C$_6$H$_5$CC— | —F | —F | —CN | —H | —C$_7$H$_{15}$ | —C$_4$H$_7$S |
| 10 | —C$_5$H$_{10}$Cl | —NO$_2$ | —OH | —H | —NO$_2$ | —CN | —OH | —SCN | —C$_3$H$_5$ | —NH$_2$CO |
| 11 | —C$_5$H$_{11}$O— | —H | —C$_6$H$_5$ | —C$_6$H$_5$ | —C$_6$H$_5$CC— | —F | —F | —CH$_3$C(CH$_3$)$_2$ | —C$_3$H$_5$ | —OH |
| 12 | —COOH | —OH | —C$_8$H$_{15}$Cl$_2$ | —C$_6$H$_5$CC— | —H | —OH | —C$_5$H$_{10}$Cl | —C$_4$H$_9$SO$_3$ | —C$_6$H$_5$CC— | —CHCH$_2$ |
| 13 | —CH$_2$N$_2$ | —H | —OCH$_3$ | —CH$_3$C(CH$_3$)$_2$ | —CH$_2$Cl | —C$_5$H$_{10}$Cl | —OH | —C$_4$H$_9$SO$_3$ | —NO$_2$ | —C$_4$H$_8$N— |
| 14 | —NH$_2$CO | —H | —C$_6$H$_5$CC— | —C$_6$H$_5$CC— | —H | —OH | —C$_5$H$_{10}$Cl | —C$_5$H$_{10}$Cl | —C$_{20}$H$_{40}$Cl | —C$_3$H$_5$ |
| 15 | —C$_5$H$_{11}$NH$_2$CO | —NH$_2$CO | —SCN | —NH$_2$CO | —FC$_6$H$_4$CH$_2$— | —FC$_6$H$_4$CH$_2$— | —C$_6$H$_5$CC— | —H | —H | —CCH |
| 16 | —CH$_3$OCOO | —H | —H | —H | —H | —SCN | —CH$_3$C(CH$_3$)$_2$ | —C$_3$H$_5$ | —CCH | —C$_4$H$_7$S |
| 17 | —C$_{15}$H$_{31}$OCOO | —H | —H | —H | —H | —NO$_2$C$_2$H$_5$S | —C$_5$H$_{10}$Cl | —C$_3$H$_5$ | —C$_4$H$_7$S | —C$_{15}$H$_{31}$OCOO |
| 18 | —CN | —H | —H | —H | —H | —H | —H | —F | —H | —CN |
| 19 | —H | —H | —H | —H | —H | —SCN | —C$_7$H$_{15}$ | —C$_7$H$_{15}$ | —H | —CN |
| 20 | —H | —C$_8$H$_{15}$Cl$_2$ | —H | —NO$_2$ | —F | —F | —F | —F | —H | —C$_5$H$_{11}$O— |
| 21 | —H | —OCH$_3$ | —CH$_3$C(CH$_3$)$_2$ | —CH$_3$O | —I | —F | —CH$_3$C(CH$_3$)$_2$ | —C$_3$H$_5$ | —CH$_3$C(CH$_3$)$_2$ | —COOH |
| 22 | —H | —C$_6$H$_5$CC— | —OCH$_3$ | —C$_6$H$_5$CC— | —F | —OH | —NO$_2$ | —C$_3$H$_5$ | —CH$_2$ | —CH$_2$NH$_2$ |
| 23 | —C$_8$H$_{17}$SO$_3$ | —NO$_2$ | —C$_6$H$_5$CC— | —NO$_2$ | —F | —OH | —C$_5$H$_{10}$Cl | —CH$_2$ | —C$_4$H$_8$N— | —NH$_2$CO |
| 24 | —C$_8$H$_{17}$S— | —SCN | —NH$_2$CO | —H | —C$_4$H$_7$S | —C$_5$H$_{10}$Cl | —NH$_2$CO | —H | —CCH | —C$_5$H$_{11}$NH$_2$CO |
| 25 | —C$_{15}$H$_{31}$S— | —NH$_2$CO | —I | —NH$_2$CO | —C$_6$H$_5$ | —C$_6$H$_5$ | —NO$_2$ | —C$_3$H$_5$ | —CCH | —CH$_3$OCOO |
| 26 | —C$_6$H$_5$ | —C$_4$H$_7$S | —H | —I | —FC$_6$H$_4$CH$_2$— | —FC$_6$H$_4$CH$_2$— | —C$_6$H$_5$CC— | —C$_4$H$_7$S | —C$_4$H$_7$S | —C$_{15}$H$_{31}$OCOO |
| 27 | —H | —CN | —C$_4$H$_7$S | —CH$_3$C(CH$_3$)$_2$ | —NO$_2$C$_2$H$_5$S | —NO$_2$C$_2$H$_5$S | —C$_7$H$_{15}$ | —C$_3$H$_5$ | —H | —CN |
| 28 | —C$_{10}$H$_{21}$CH$_2$O | —H | —H | —H | —H | —F | —CH$_3$C(CH$_3$)$_2$ | —F | —CH$_3$C(CH$_3$)$_2$ | —CN |
| 29 | —C$_{10}$H$_{21}$COO | —OH | —H | —NO$_2$ | —CH$_3$C(CH$_3$)$_2$ | —C$_5$H$_{10}$Cl | —C$_5$H$_{10}$Cl | —CN | —CH$_3$SO$_2$ | —C$_6$H$_{10}$Cl |
| 30 | —C$_5$H$_{11}$CO | —NH$_2$CO | —H | —C$_6$H$_5$CC— | —FC$_6$H$_4$CH$_2$— | —NO$_2$ | —NO$_2$ | —C$_5$H$_{10}$Cl | —C$_4$H$_9$SO$_2$ | —CH$_2$—NH$_2$CO |
| 31 | —H | —C$_6$H$_5$CC— | —C$_6$H$_5$CC— | —NH$_2$CO | —C$_{15}$H$_{31}$S— | —NH$_2$CO | —NH$_2$CO | —H | —NH$_2$CO | —NH$_2$NH$_2$CO |
| 32 | —C$_8$H$_{17}$S— | —SCN | —NH$_2$CO | —H | —CH$_3$C(CH$_3$)$_2$ | —C$_5$H$_{10}$Cl | —NH$_2$CO | —C$_3$H$_5$ | —H | —C$_5$H$_{11}$NH$_2$CO |
| 33 | —C$_8$H$_{17}$S— | —C$_5$H$_{10}$Cl | —C$_6$H$_5$CC— | —H | —FC$_6$H$_4$CH$_2$— | —C$_5$H$_{10}$Cl | —NH$_2$CO | —OH | —SCN | —CH$_3$OCOO |
| 34 | —C$_{15}$H$_{31}$S— | —C$_6$H$_5$CC— | —NH$_2$CO | —H | —C$_{15}$H$_{31}$S— | —C$_3$H$_5$ | —NO$_2$ | —C$_4$H$_7$S | —C$_4$H$_7$S | —C$_{15}$H$_{31}$OCOO |
| 35 | —C$_6$H$_5$ | —NH$_2$CO | —NH$_2$CO | —H | —CH$_3$C(CH$_3$)$_2$ | —CH$_3$C(CH$_3$)$_2$ | —C$_6$H$_{13}$S— | —C$_3$H$_5$ | —NO$_2$ | —NO$_2$ |
| 36 | —C$_6$H$_5$ | —OH | —I | —H | —CH$_3$C(CH$_3$)$_2$ | —CH$_3$C(CH$_3$)$_2$ | —CH$_3$C(CH$_3$)$_2$ | —C$_3$H$_5$ | —I | —C$_4$H$_7$S |
| 37 | —C$_2$H$_5$ | —C$_4$H$_7$S | —H | —H | —H | —C$_4$H$_7$S | —C$_{15}$H$_{31}$S— | —C$_4$H$_7$S | —C$_4$H$_7$S | —C$_3$H$_5$ |
| 38 | —C$_5$H$_{10}$Cl | —C$_3$H$_5$ | —SCN | —H | —H | —OH | —C$_{15}$H$_{31}$S— | —C$_{11}$H$_{21}$SO$_3$ | —I | —CH$_2$CH— |
| 39 | —C$_2$H$_5$O | —CH$_3$ | —OH | —H | —SCN | —NH$_2$CO | —C$_5$H$_{10}$Cl | —C$_4$H$_7$S | —CH$_3$C(CH$_3$) | —SCN |
| 40 | —H | —OH | —NH$_2$CO | —H | —OH | —OH | —CH$_3$OCOO | —FC$_6$H$_4$CH$_2$— | —NH$_2$CO | —H |
| 41 | —C$_5$H$_9$ | —C$_4$H$_7$S | —C$_6$H$_5$CC— | —CH$_3$C(CH$_3$)$_2$ | —CH$_3$C(CH$_3$)$_2$ | —CH$_3$C(CH$_3$)$_2$ | —CH$_3$C(CH$_3$)$_2$ | —NO$_2$ | —I | —C$_6$H$_5$CC— |
| 42 | —CH$_3$CH— | —CH$_3$OCOO | —C$_2$H$_5$SO$_3$ | —C$_2$H$_5$ | —FC$_6$H$_4$CH$_2$— | —NH$_2$CO | —NH$_2$CO | —C$_6$H$_5$CC— | —CH$_3$C(CH$_3$) | —C$_{17}$H$_{35}$— |
| 43 | —C$_6$H$_5$CC— | —C$_{11}$H$_{21}$SO$_3$ | —OH | —NH$_2$CO | —H | —NH$_2$CO | —C$_{15}$H$_{31}$S— | —C$_{15}$H$_{31}$S— | —NH$_2$CO | —C$_{15}$H$_{31}$S— |
| 44 | —CHC— | —C$_4$H$_7$S— | —SCN | —C$_5$H$_{10}$Cl | —H | —NH$_2$CO | —C$_4$H$_7$S— | —SCN | —CH$_3$C(CH$_3$) | —H |
| 45 | —C$_6$H$_5$CC— | —CN | —NH$_2$CO | —C$_{11}$H$_{21}$SO$_2$ | —H | —C$_{15}$H$_{31}$S— | —C$_9$H$_{19}$SO$_3$ | —C$_{11}$H$_{21}$SO$_2$ | —H | —C$_7$H$_{15}$ |
| 46 | —OCH$_3$ | —CHC— | —CH$_3$OCOO | —SCN | —H | —H | —C$_4$H$_7$S— | —SCN | —NH$_2$CO | —C$_7$H$_{15}$S— |
| 47 | —NO$_2$ | —C$_6$H$_5$CC— | —F | —CH$_2$Cl | —CN | —H | —H | —FC$_6$H$_4$CH$_2$— | —NH$_2$CO | —C$_{15}$H$_{31}$S— |

TABLE 1-continued

Specific examples of the flavone derivatives and flavanone derivatives provided in embodiments of the present invention.

| No. | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 48 | —SCN | —$NH_2CO$ | —I | $FC_6H_4CH_2$— | —$C_9H_{19}SO_3$ | —H | $CH_3COO$— | $C_6H_5CC$— | —H | $BrNO_2C_{15}H_{29}S$— |
| 49 | —$C_5H_{10}Cl$ | —$NO_2$ | $C_6H_5CC$— | —F | —$CH_2Cl$ | —H | —OH | —$C_{20}H_{40}Cl$ | —$C_3H_5$ | —H |
| 50 | —OH | $C_6H_5CC$— | —$C_6H_5$ | —$CH_2Cl$ | —CN | —H | —H | —CHC | $CH_3OCOO$— | —$NH_2CO$ |
| 51 | —$C_4H_7S$ | —$NO_2$ | —F | —F | —$CH_2Cl$ | —$C_9H_{19}SO_3$ | —H | —H | —H | —$C_5H_8Cl$ |
| 52 | —CN | —OH | —$C_6H_5$ | —H | —H | —$C_5H_{10}Cl$ | —$C_7H_{15}$ | —H | —H | —H |
| 53 | —SCN | —$NH_2CO$ | $NH_2CO$— | $FC_6H_4CH_2$— | $BrNO_2C_{15}H_{29}S$— | —$C_5H_{10}Cl$ | —H | —H | —H | $BrNO_2C_{15}H_{29}S$— |
| 54 | —$C_5H_{10}Cl$ | —$NO_2$ | $C_6H_5CC$— | $FC_6H_4CH_2$— | —$C_4H_7S$ | —$C_5H_{10}Cl$ | —$C_7H_{15}$ | —H | —H | —H |
| 55 | —SCN | —$NH_2CO$ | —I | —$C_3H_6Cl$ | —$NH_2CO$ | —CN | —F | —$CCH$ | —$C_4H_7S$ | —OH |
| 56 | —H | —H | —$C_4H_8Cl$ | —H | —$NO_2$ | $C_6H_5CC$— | —F | —$CH_2Cl$ | —CN | —OH |
| 57 | —H | —H | —$NO_2$ | —H | —H | $C_6H_5CC$— | —F | —$CH_2Cl$ | —CN | —OH |
| 58 | —H | —H | —$C_6H_5CC$ | —$C_5H_6Cl$ | —$NO_2$ | $C_6H_5CC$— | —F | —$CH_2Cl$ | —CN | —$C_9H_{19}SO_3$ |
| 59 | —H | —H | —H | $CH_3OCOO$— | —H | $C_6H_5CC$— | —I | —$CH_2Cl$ | —CN | $CH_3OCOO$— |
| 60 | —H | —H | —COOH | $FC_6H_4CH_2$— | —$NO_2$ | —H | —I | —$CH_2Cl$ | —CN | —$C_4H_7S$ |
| 61 | —H | —H | —CN | —$C_5H_{10}Cl$ | —H | $C_6H_5CC$— | —I | —$CH_2Cl$ | —CN | —OH |
| 62 | —H | —H | —COOH | $CH_3OCOO$— | —$NO_2$ | $C_6H_5CC$— | —I | —$CH_2Cl$ | —CN | —OH |
| 63 | —H | —H | —$C_9H_{19}SO_3$ | $CH_3OCOO$— | —SCN | —H | —H | —H | —$C_4H_7S$ | —$C_5H_{10}Cl$ |
| 64 | —$C_{10}H_{21}COO$ | —H | —H | —H | —H | —$NH_2CO$ | $C_6H_5CC$— | $FC_6H_4CH_2$— | $CH_3C(CH_3)_2$— | $CH_3OCOO$— |
| 65 | $C_8H_{11}CO$— | —H | —H | —$C_4H_7S$ | —H | —SCN | —H | —$NH_2CO$ | —$OC_2H_5$ | —$C_6H_5CC$ |
| 66 | —$C_8H_{17}S$ | —$C_2H_5O$ | —H | $CH_3OCOO$— | —$C_6H_4H_7S$ | —SCN | —H | —$C_5H_{10}SO_3$ | —H | —H |
| 67 | —$C_{11}H_{21}SO_3$ | —$NH_2CO$ | —H | $CH_3C(CH_3)_2$ | —$NH_2CO$ | —H | $C_6H_4H_7S$— | —H | —H | —$C_{11}H_{21}SO_3$ |
| 68 | —$C_8H_{17}S$ | —F | —H | —SCN | —$C_9H_{19}SO_3$ | —CN | $FC_6H_4CH_2$— | —$C_6H_5$ | —H | $BrNO_2C_{15}H_{29}S$— |
| 69 | —$C_5H_{10}Cl$ | —CN | —H | —F | —I | $CH_3OCOO$— | —OH | —$C_6H_5$ | —H | —$NH_2CO$ |
| 70 | —$NH_2CO$ | —$NH_2$ | —H | —$C_6H_5$ | —$C_{15}H_{31}S$ | —H | —$NH_2CO$ | —$C_6H_5CC$ | —H | —$C_5H_{10}Cl$ |
| 71 | $CH_3OCOO$— | —$C_6H_5CH_2$ | —$CH_2Cl$ | —H | —I | —SCN | —$NH_2CO$ | —CN | $FC_6H_4CH_2$— | —$C_6H_5CC$ |
| 72 | —$C_4H_7S$ | —Br | —$C_6H_5CC$ | —H | —$CH_2Cl$ | —H | —OH | —$CCH$ | —$C_9H_{19}SO_3$ | —OH |
| 73 | —SCN | —$NH_2$ | —$C_3H_5$ | —H | —$C_3H_5$ | —$C_6H_{10}Cl$ | —OH | —$CH_2Cl$ | $C_7H_{15}O$— | —$C_4H_7S$ |
| 74 | —$NH_2CO$ | —F | —H | —H | —$CH_2Cl$ | —$C_5H_{10}Cl$ | —F | —$CH_2Cl$ | —$C_3H_5$ | —$C_6H_5$ |
| 75 | —COOH | —CN | —$NO_2$ | —H | —H | —OH | —H | —$C_4H_8N$ | —H | —H |
| 76 | —$NH_2$ | —H | —$C_5H_{11}$ | —$CH_2Cl$ | —H | —$CH_2Cl$ | —F | —$C_3H_5$ | —F | —COOH |
| 77 | —SCN | —CHC | —SCN | $C_6H_5CH_2$— | —$CH_2Cl$ | —$CH_2Cl$ | —H | —CN | —H | —$CH_2Cl$ |
| 78 | —$NO_2$ | —$NH_2$ | $C_6H_5CC$— | —$NH_2CO$ | —H | —H | —H | —CN | —COOH | —$C_4H_7S$ |
| 79 | —$C_9H_{19}SO_3$ | —$NO_2$ | —$C_3H_5$ | —$C_5H_{10}Cl$ | —H | —OH | —OH | —H | —$C_2H_5$ | —$C_6H_5CC$ |
| 80 | —$NH_2CO$ | —$NO_2$ | —$NO_2$ | —H | —H | —$CH_2Cl$ | —F | —$C_3H_5$ | —H | —H |
| 81 | —$C_9H_{19}SO_3$ | —F | —$C_5H_{11}$ | —$CH_2Cl$ | —$CH_2Cl$ | —H | —H | —CN | —OH | —OH |
| 82 | —$C_9H_{19}SO_3$ | —H | —SCN | $NH_2CO$— | —H | —$C_5H_{10}Cl$ | —H | —CN | —OH | —$C_5H_{10}Cl$ |
| 83 | —$C_{15}H_{31}S$ | —$NO_2$ | —$CH_3$ | —$C_5H_8Cl$ | —H | —$C_5H_{10}Cl$ | —H | —CN | —F | —$C_6H_5CC$ |
| 84 | —$NH_2CO$ | —F | —$C_6H_5CH_2$ | —$C_5H_8Cl$ | —$NO_2$ | —$C_5H_{10}Cl$ | —H | —H | —$C_3H_5$ | —OH |
| 85 | —$C_6H_5CC$ | —CHC | —$NO_2$ | —$C_5H_8Cl$ | —H | —OH | —H | —H | —H | —$C_4H_7S$ |
| 86 | —$C_6H_5CC$ | —$NO_2$ | —$C_3H_5$ | $NH_2CO$— | —H | —$CH_2Cl$ | —H | —H | —$C_3H_5$ | —$C_4H_8N$ |
| 87 | —F | —$NH_2$ | —$CH_3$ | —H | —$NO_2$ | —H | —F | —H | —H | —H |
| 88 | —CN | —OH | —$C_3H_5$ | —H | —CN | —OH | —H | —F | —F | —$C_6H_5CC$ |
| 89 | —H | —F | —H | —$CH_3$ | —H | —OH | —H | —H | —$C_9H_{19}SO_3$ | —$NO_2$ |
| 90 | —$C_4H_7S$ | —F | —H | —$C_9H_{19}SO_3$ | —H | —$C_9H_{19}SO_3$ | —OH | —CHC | —$NO_2$ | —$C_3H_5$ |
| 91 | —H | —$NO_2$ | —H | —$C_4H_7S$ | —$C_5H_9$ | —OH | —H | —OH | —$C_3H_5$ | —$C_4H_8N$ |
| 92 | —CHC | —$NH_2$ | —H | —$CH_3$ | —OH | —CHC | —$CH_2CH$ | —F | —H | —$C_3H_5$ |
| 93 | —H | —COOH | —H | —H | —OH | —$C_2H_5O$ | —$CH_2CH$ | —OH | —H | —H |
| 94 | —H | —$NO_2$ | —H | —H | —H | —H | —H | —H | —H | —H |
| 95 | —H | —$NH_2$ | —H | —H | —H | —H | $NH_2CO$— | —$NH_2$ | —H | —$NO_2$ |
| 96 | —H | —CHC | —H | —H | —H | —OH | $CH_2CH$— | $NH_2CO$— | —$CH_3$ | —$C_9H_{19}SO_3$ |

TABLE 1-continued

Specific examples of the flavone derivatives and flavanone derivatives provided in embodiments of the present invention.

| No. | R$_1$ | R$_2$ | R$_3$ | R$_4$ | R$_5$ | R$_6$ | R$_7$ | R$_8$ | R$_9$ | R$_{10}$ |
|---|---|---|---|---|---|---|---|---|---|---|
| 97 | —H | —NO$_2$ | —H | —C$_9$H$_{19}$SO$_3$ | —C$_6$H$_5$CC— | —OH | —C$_3$H$_5$ | —H | —NH$_2$CO— | —C$_4$H$_7$S— |
| 98 | —H | —C$_9$H$_{19}$CC— | —H | —NO$_2$ | —C$_6$H$_5$CC— | —C$_3$H$_5$ | —OH | —C$_4$H$_7$S— | —H | —NH$_2$CO— |
| 99 | —H | —C$_6$H$_5$CC— | —H | —C$_9$H$_{19}$SO$_3$ | —H | —OH | —C$_3$H$_5$ | —NH$_2$CO— | —C$_4$H$_7$S— | —H |
| 100 | —H | —C$_9$H$_{19}$SO$_3$ | —H | —C$_9$H$_{19}$SO$_3$ | —H | —NO$_2$ | —C$_6$H$_5$CC— | —NH$_2$CO— | —NO$_2$ | —OH |
| 101 | —H | —C$_4$H$_7$S— | —H | —C$_9$H$_{19}$SO$_3$ | —NH$_2$CO— | —H | —C$_3$H$_5$ | —NO$_2$ | —CHC— | —OH |
| 102 | —H | —C$_3$H$_5$ | —H | —NH$_2$CO— | —NH$_2$CO— | —C$_4$H$_7$S— | —C$_3$H$_5$ | —C$_6$H$_5$CC— | —H | —OH |
| 103 | —H | —NO$_2$ | —H | —CHC— | —C$_6$H$_5$CC— | —OH | —C$_3$H$_5$ | —NO$_2$ | —CHC— | —C$_5$H$_8$Cl |
| 104 | —H | —NH$_2$CO— | —H | —C$_3$H$_5$ | —NH$_2$CO— | —C$_4$H$_7$S— | —C$_3$H$_5$ | —C$_2$H$_5$ | —H | —OH |
| 105 | —H | —NO$_2$ | —H | —C$_9$H$_{19}$SO$_3$ | —C$_6$H$_5$CC— | —C$_4$H$_7$S— | —C$_3$H$_5$ | —NH$_2$CO— | —C$_4$H$_7$S— | —H |
| 106 | —H | —CN | —H | —C$_3$H$_5$ | —OH | —C$_4$H$_7$S— | —C$_3$H$_5$ | —NH$_2$CO— | —C$_9$H$_{19}$SO$_3$ | —NO$_2$ |
| 107 | —H | —NO$_2$ | —CHC— | —C$_{15}$H$_{31}$S— | —H | —C$_4$H$_7$S— | —NH$_2$CO— | —C$_3$H$_5$ | —C$_4$H$_7$S— | —OH |
| 108 | —H | —NH$_2$ | —C$_6$H$_5$CC— | —CH$_2$CH$_2$SO$_3$H | —H | —C$_4$H$_7$S— | —H | —H | —C$_3$H$_5$ | —OH |
| 109 | —H | —C$_5$H$_{11}$ | —C$_3$H$_5$ | —C$_9$H$_{19}$SO$_3$ | —C$_9$H$_{19}$SO$_3$ | —OH | —OH | —NH$_2$CO— | —C$_4$H$_7$S— | —NO$_2$ |
| 110 | —H | —NO$_2$ | —NO$_2$ | —OH | —CH$_2$CH— | —H | —H | —NH$_2$CO— | —C$_4$H$_7$S— | —OH |
| 111 | —H | —C$_6$H$_5$ | —C$_6$H$_5$CC— | —NO$_2$ | —C$_9$H$_{19}$SO$_3$ | —C$_3$H$_5$ | —NH$_2$CO— | —NH$_2$CO— | —NH$_2$CO— | —C$_4$H$_7$S— |
| 112 | —H | —OH | —CHC— | —OH | —NH$_2$CO— | —C$_3$H$_5$ | —H | —H | —C$_4$H$_7$S— | —C$_4$H$_7$S— |
| 113 | —H | —C$_9$H$_{19}$SO$_3$ | —C$_6$H$_5$CC— | —C$_9$H$_{19}$SO$_3$ | —C$_6$H$_5$CC— | —C$_3$H$_5$ | —C$_3$H$_5$ | —NH$_2$CO— | —C$_4$H$_7$S— | —H |
| 114 | —H | —C$_6$H$_5$CC— | —NO$_2$ | —C$_9$H$_{19}$SO$_3$ | —H | —C$_3$H$_5$ | —OH | —NH$_2$CO— | —C$_4$H$_7$S— | —C$_4$H$_7$S— |
| 115 | —H | —NH$_2$ | —OH | —C$_9$H$_{19}$SO$_3$ | —C$_6$H$_5$CC— | —C$_3$H$_5$ | —C$_4$H$_7$S— | —NH$_2$CO— | —C$_4$H$_7$S— | —NO$_2$ |
| 116 | —H | —NH$_2$ | —C$_6$H$_5$CC— | —C$_9$H$_{19}$SO$_3$ | —NH$_2$CO— | —OH | —OH | —H | —C$_4$H$_7$S— | —OH |
| 117 | —H | —NO$_2$ | —H | —C$_9$H$_{19}$SO$_3$ | —C$_6$H$_5$CC— | —H | —H | —NH$_2$CO— | —H | —C$_4$H$_7$S— |
| 118 | —H | —NO$_2$ | —C$_6$H$_5$CC— | —C$_9$H$_{19}$SO$_3$ | —OH | —OH | —C$_6$H$_5$CC— | —CH$_3$ | —NH$_2$CO— | —CH$_2$CH— |
| 119 | —C$_9$H$_{19}$SO$_3$ | —H | —H | —H | —NO$_2$ | —H | —CHC— | —NH$_2$CO— | —CHC— | —F |
| 120 | —COOH | —H | —C$_6$H$_5$ | —C$_4$H$_7$S— | —C$_6$H$_5$ | —OH | —C$_6$H$_5$CC— | —OH | —C$_4$H$_7$S— | —C$_6$H$_5$ |
| 121 | —F | —C$_4$H$_8$N— | —C$_5$H$_{10}$Cl | —C$_4$H$_7$S— | —CH$_2$Cl | —F | —H | —C$_3$H$_5$ | —C$_4$H$_7$S— | —C$_3$H$_5$ |
| 122 | —C$_6$H$_5$CC— | —CN | —H | —NH$_2$CO— | —NH$_2$ | —CN | —OH | —CH$_3$ | —CH$_3$ | —OH |
| 123 | —OH | —NO$_2$ | —H | —C$_6$H$_5$ | —OH | —CH$_2$OCOO— | —OH | —CHC— | —NH$_2$CO— | —NO$_2$ |
| 124 | —CH$_3$ | —C$_9$H$_{19}$SO$_3$ | —CH$_3$ | —F | —CH$_2$Cl | —CH$_3$OCOO— | —OH | —OH | —H | —OH |
| 125 | —H | —SCN | —H | —C$_9$H$_{19}$SO$_3$ | —CHC— | —CH$_2$Cl | —OH | —CH$_3$ | —H | —C$_4$H$_7$S— |
| 126 | —H | —H | —H | —H | —C$_6$H$_5$ | —CH$_2$Cl | —H | —H | —F | —CH$_2$CH— |
| 127 | —H | —H | —H | —NH$_2$CO— | —CH$_2$Cl | —C$_4$H$_7$S— | —OH | —NH$_2$CO— | —H | —F |
| 128 | —H | —H | —NH$_2$ | —C$_6$H$_5$ | —F | —CN | —OH | —CN | —C$_6$H$_5$ | —C$_6$H$_5$ |
| 129 | —H | —H | —NO$_2$ | —F | —CN | —CH$_3$C(CH$_3$)$_2$— | —C$_6$H$_5$OCOO— | —OCH$_3$ | —OH | —C$_3$H$_5$ |
| 130 | —H | —H | —NH$_2$CO— | —H | —CH$_2$Cl | —H | —CH$_3$OCOO— | —CH$_3$ | —CH$_3$ | —C$_3$H$_5$ |
| 131 | —H | —H | —SCN | —H | —CN | —CH$_2$OCOO— | —CH$_3$OCOO— | —CHC— | —CH$_2$Cl | —H |
| 132 | —H | —H | —C$_5$H$_{10}$Cl | —CH$_2$Cl | —C$_9$H$_{19}$SO$_3$ | —C$_4$H$_7$S— | —C$_6$H$_5$CC— | —OCH$_3$ | —C$_6$H$_5$ | —CH$_3$ |
| 133 | —H | —H | —NH$_2$ | —H | —SCN | —CN | —OH | —C$_{10}$H$_{21}$COO— | —F | —C$_6$H$_5$ |
| 134 | —H | —H | —NH$_2$CO— | —NH$_2$CO— | —H | —CH$_3$C(CH$_3$)$_2$— | —CH$_3$OCOO— | —COOH | —SCN | —OH |
| 135 | —H | —H | —SCN | —CH$_2$Cl | —H | —C$_4$H$_7$S— | —CH$_3$OCOO— | —OCH$_3$ | —C$_4$H$_7$S— | —C$_9$H$_{19}$SO$_3$ |
| 136 | —H | —H | —C$_5$H$_{10}$Cl | —H | —SCN | —CN | —C$_4$H$_7$S— | —C$_6$H$_5$CC— | —CH$_3$ | —I |
| 137 | —H | —H | —NH$_2$ | —F | —H | —CH$_3$C(CH$_3$)$_2$— | —OH | —C$_6$H$_5$ | —C$_6$H$_5$ | —H |
| 138 | —H | —H | —NH$_2$ | —FC$_6$H$_4$CH$_2$— | —H | —H | —C$_{10}$H$_{21}$COO— | —COOH | —F | —C$_9$H$_{19}$SO$_3$ |
| 139 | —H | —H | —NH$_2$CO— | —NH$_2$CO— | —NH$_2$ | —C$_4$H$_7$S— | —CH$_3$OCOO— | —OCH$_3$ | —H | —OCH$_3$ |
| 140 | —H | —H | —SCN | —CH$_2$Cl | —OH | —CN | —C$_6$H$_5$CC— | —CH$_3$ | —CH$_3$ | —H |
| 141 | —H | —H | —C$_5$H$_{10}$Cl | —H | —SCN | —CH$_3$C(CH$_3$)$_2$— | —OH | —C$_6$H$_5$ | —C$_6$H$_5$ | —CN |
| 142 | —H | —H | —NH$_2$ | —SCN | —H | —H | —C$_{10}$H$_{21}$COO— | —C$_4$H$_7$S— | —F | —C$_9$H$_{19}$SO$_3$ |
| 143 | —H | —H | —NO$_2$ | —CH$_2$Cl | —OH | —H | —CH$_3$OCOO— | —COOH | —SCN | —OCH$_3$ |
| 144 | —H | —H | —NO$_2$ | —C$_6$H$_5$CC— | —CN | —H | —CH$_3$OCOO— | —OCH$_3$ | —C$_6$H$_5$ | —H |
| 145 | —H | —H | —NH$_2$CO— | —C$_4$H$_7$S— | —FC$_6$H$_4$CH$_2$— | —H | —C$_{10}$H$_{21}$COO— | —H | —SCN | —C$_9$H$_{19}$SO$_3$ |

TABLE 1-continued

Specific examples of the flavone derivatives and flavanone derivatives provided in embodiments of the present invention.

| No. | R$_1$ | R$_2$ | R$_3$ | R$_4$ | R$_5$ | R$_6$ | R$_7$ | R$_8$ | R$_9$ | R$_{10}$ |
|---|---|---|---|---|---|---|---|---|---|---|
| 146 | —H | —H | —SCN | —CN | NH$_2$CO— | —H | CH$_3$OCOO— | —C$_4$H$_7$S | —H | —OCH$_3$ |
| 147 | —H | —H | —C$_5$H$_{10}$Cl | —CH$_3$C(CH$_3$)$_2$ | —SCN | —H | C$_6$H$_5$CC— | —COOH | —CH$_3$ | —H |
| 148 | —H | —H | —NH$_2$ | —OH | —OCH$_3$ | —CH$_2$Cl | —H | —H | —C$_6$H$_5$ | —CN |
| 149 | —H | —H | —NO$_2$ | —F | —CN | CH$_3$OCOO— | —H | C$_6$H$_5$CC— | —H | —C$_9$H$_{19}$SO$_3$ |
| 150 | —H | —H | NH$_2$CO— | —I | FC$_6$H$_4$CH$_2$— | —C$_4$H$_7$S | C$_{10}$H$_{21}$COO— | —H | —SCN | —OCH$_3$ |
| 151 | —H | —H | —SCN | —C$_4$H$_7$S | NH$_2$CO— | —CN | —H | —COOH | —H | —CH$_3$ |
| 152 | —H | —H | —C$_5$H$_{10}$Cl | —CH$_3$ | —H | —CH$_3$C(CH$_3$)$_2$ | C$_6$H$_5$CC— | NH$_2$CO— | —C$_4$H$_7$S | —C$_6$H$_5$ |
| 153 | —C$_6$H$_5$ | —OH | —H | —H | —H | —OH | —H | —CN | —CH$_3$ | —OH |
| 154 | —F | —CH$_2$Cl | —H | —H | —CH$_2$Cl | —OH | C$_6$H$_5$CC— | —F | —NO$_2$ | —H |
| 155 | —CN | —C$_9$H$_{19}$SO$_3$ | —H | —H | —C$_9$H$_{19}$SO$_3$ | —F | —OH | —C$_3$H$_5$ | —H | —CH$_3$ |
| 156 | —CH$_2$Cl | —NO$_2$ | —H | —H | —NO$_2$ | —CN | —C$_3$H$_5$ | NH$_2$CO— | C$_6$H$_5$CC— | CHC— |
| 157 | —C$_6$H$_5$ | —SCN | —H | —H | —SCN | —CH$_2$Cl | C$_6$H$_5$CC— | —CN | —C$_4$H$_7$S | —H |
| 158 | —F | —OH | —C$_3$H$_5$ | —H | —H | —OH | —H | —H | —CH$_3$ | —CH$_3$ |
| 159 | —CN | —CH$_2$Cl | —OH | —H | —H | —OH | C$_6$H$_5$CC— | —F | —NO$_2$ | —C$_6$H$_5$ |
| 160 | —CH$_2$Cl | —C$_9$H$_{19}$SO$_3$ | —H | —H | —C$_4$H$_7$S | —F | —OH | —CH$_3$ | —H | —OH |
| 161 | —C$_6$H$_5$ | —NO$_2$ | —F | —H | —H | —CN | —C$_9$H$_{19}$SO$_3$ | —NO$_2$ | CHC— | CHC— |
| 162 | —F | —SCN | —CN | —H | —H | —CH$_2$Cl | —CN | —CH$_3$ | —OH | —H |
| 163 | —CN | —OH | —C$_3$H$_5$ | —H | —H | —H | —OH | —OCH$_3$ | —C$_6$H$_5$ | —CH$_3$ |
| 164 | —CH$_2$Cl | —CH$_2$Cl | —OH | —H | —H | —H | —H | C$_6$H$_5$CC— | —F | —C$_6$H$_5$ |
| 165 | —C$_6$H$_5$ | —C$_9$H$_{19}$SO$_3$ | —H | NH$_2$CO— | —H | —H | C$_{10}$H$_{21}$COO— | —C$_4$H$_7$S | —H | —OH |
| 166 | —F | —NO$_2$ | —H | —CN | —H | CH$_3$OCOO— | CH$_3$OCOO— | —COOH | —C$_6$H$_5$ | —C$_9$H$_{19}$SO$_3$ |
| 167 | —CN | —SCN | —H | —C$_6$H$_4$CH$_2$— | C$_6$H$_5$CC— | —C$_4$H$_7$S | C$_6$H$_5$CC— | —H | —SCN | —OCH$_3$ |
| 168 | —CH$_2$Cl | —OH | —H | NH$_2$CO— | —C$_4$H$_7$S | —CN | C$_{10}$H$_{21}$COO— | —SCN | —H | —CN |
| 169 | —C$_6$H$_5$ | —CH$_2$Cl | —H | —CN | —COOH | —CH$_3$C(CH$_3$)$_2$ | CH$_3$OCOO— | —OCH$_3$ | —CH$_3$ | —I |
| 170 | —F | —C$_9$H$_{19}$SO$_3$ | —H | —CH$_2$Cl | —CN | —C$_6$H$_5$ | CH$_3$OCOO— | —COOH | —OCH$_3$ | —CH$_3$ |
| 171 | —CN | —NO$_2$ | —C$_3$H$_5$ | —CN | —OH | —CH$_3$C(CH$_3$)$_2$ | —H | —SCN | C$_6$H$_5$CC— | —CN |
| 172 | —NH$_2$ | —H | —H | —CH$_2$Cl | —SCN | —H | —H | —H | —F | —H |
| 173 | —NO$_2$ | —H | —H | —CN | —COOH | —H | —H | —H | —SCN | —C$_9$H$_{19}$SO$_3$ |
| 174 | NH$_2$CO— | —H | —H | FC$_6$H$_4$CH$_2$— | —C$_9$H$_{19}$SO$_3$ | CH$_3$OCOO— | C$_{10}$H$_{21}$COO— | —H | —H | —OCH$_3$ |
| 175 | —SCN | —H | —H | NH$_2$CO— | —SCN | —C$_4$H$_7$S | CH$_3$OCOO— | —C$_4$H$_7$S | —CH$_3$ | —CN |
| 176 | —C$_5$H$_{10}$Cl | —H | —H | —SCN | —COOH | —CN | C$_6$H$_5$CC— | —COOH | —C$_6$H$_5$ | —I |
| 177 | —NH$_2$ | —H | —H | —CH$_2$Cl | —OH | —CH$_3$C(CH$_3$)$_2$ | C$_{10}$H$_{21}$COO— | —OCH$_3$ | —F | —CH$_3$ |
| 178 | —NO$_2$ | —H | —H | —CN | —SCN | —C$_6$H$_5$ | CH$_3$OCOO— | —SCN | —OCH$_3$ | —CN |
| 179 | NH$_2$CO— | —H | —H | FC$_6$H$_4$CH$_2$— | —COOH | —CH$_3$C(CH$_3$)$_2$ | CH$_3$OCOO— | —H | C$_6$H$_5$CC— | —H |
| 180 | —SCN | —H | —H | NH$_2$CO— | —OH | CH$_3$OCOO— | C$_6$H$_5$CC— | —SCN | —OCH$_3$ | —C$_9$H$_{19}$SO$_3$ |
| 181 | —C$_5$H$_{10}$Cl | —H | —H | —SCN | CH$_3$OCOO— | —C$_4$H$_7$S | C$_{10}$H$_{21}$COO— | —H | —H | —OCH$_3$ |
| 182 | —NH$_2$ | —H | —H | —CH$_2$Cl | —C$_5$H$_9$S | —CN | CH$_3$OCOO— | —CH$_3$ | —CH$_3$ | —CN |
| 183 | —NO$_2$ | —H | —H | —CN | —C$_5$H$_{10}$Cl | —CH$_3$C(CH$_3$)$_2$ | C$_6$H$_5$CC— | —OCH$_3$ | —C$_6$H$_5$ | —I |
| 184 | NH$_2$CO— | —H | —H | FC$_6$H$_4$CH$_2$— | —OH | —CH$_3$C(CH$_3$)$_2$ | C$_{10}$H$_{21}$COO— | —H | —F | —CH$_3$ |
| 185 | —C$_4$H$_7$S | —H | —H | NH$_2$CO— | —CN | —CH$_2$Cl | CH$_3$OCOO— | —CH$_3$ | —OCH$_3$ | —H |
| 186 | —C$_5$H$_{10}$Cl | —H | —H | —SCN | —SCN | —H | C$_6$H$_5$CC— | —H | —C$_6$H$_5$ | —CN |
| 187 | —NH$_2$ | —H | —H | —CH$_2$Cl | —COOH | —H | C$_{10}$H$_{21}$COO— | —OCH$_3$ | —F | —C$_9$H$_{19}$SO$_3$ |
| 188 | —NO$_2$ | —H | —H | —CN | —OH | —CH$_3$C(CH$_3$)$_2$ | CH$_3$OCOO— | —H | —OCH$_3$ | —OCH$_3$ |
| 189 | NH$_2$CO— | —H | —H | FC$_6$H$_4$CH$_2$— | —SCN | —CH$_3$C(CH$_3$)$_2$ | C$_6$H$_5$CC— | —SCN | —C$_6$H$_5$ | —CN |
| 190 | —SCN | —H | —H | NH$_2$CO— | CH$_3$OCOO— | —CH$_3$C(CH$_3$)$_2$ | C$_{10}$H$_{21}$COO— | —CH$_3$ | —CH$_3$ | —I |
| 191 | —C$_5$H$_{10}$Cl | —H | —H | —SCN | —C$_5$H$_9$S | —CH$_3$C(CH$_3$)$_2$ | CH$_3$OCOO— | —SCN | —OCH$_3$ | —CH$_3$ |
| 192 | —C$_6$H$_5$CC— | —H | —H | —SCN | —C$_5$H$_{10}$Cl | —CH$_3$C(CH$_3$)$_2$ | —OCH$_3$ | —H | —CH$_3$ | —COOH |
| 193 | —NH$_2$ | —H | —H | —SCN | —OH | —CH$_3$C(CH$_3$)$_2$ | CH$_3$OCOO— | —H | —H | —CH$_3$ |
| 194 | —NO$_2$ | —H | —H | —C$_6$H$_5$CC— | —CN | —C$_9$H$_{19}$SO$_3$ | —H | —H | —F | —C$_6$H$_5$ |

TABLE 1-continued

Specific examples of the flavone derivatives and flavanone derivatives provided in embodiments of the present invention.

| No. | R$_1$ | R$_2$ | R$_3$ | R$_4$ | R$_5$ | R$_6$ | R$_7$ | R$_8$ | R$_9$ | R$_{10}$ |
|---|---|---|---|---|---|---|---|---|---|---|
| 195 | NH$_2$CO— | C$_4$H$_7$S— | —H | —H | FC$_6$H$_4$CH$_2$— | —H | —H | C$_{10}$H$_{21}$COO— | —SCN | —I |
| 196 | —SCN | —CN | —H | —H | NH$_2$C O— | —H | CH$_3$OCOO— | —COOH | —C$_4$H$_7$S— | —OCH$_3$ |
| 197 | —C$_5$H$_{10}$Cl | CH$_3$C(CH$_3$)$_2$— | —H | —H | —SCN | —H | C$_6$H$_5$CC— | —CN | —C$_6$H$_5$ | —CH$_3$ |
| 198 | —NH$_2$ | —OH | —H | —H | —OCH$_3$ | CH$_3$OCOO— | —CH$_2$Cl | —CN | —H | —H |
| 199 | —NO$_2$ | —F | —H | —H | —CN | —C$_4$H$_7$S— | —H | —H | —H | —C$_9$H$_{19}$SO$_3$ |
| 200 | NH$_2$CO— | —I | —H | —H | FC$_6$H$_4$CH$_2$— | —CN | CH$_3$OCOO— | C$_{10}$H$_{21}$COO— | C$_6$H$_5$CC— | —SCN |
| 201 | —SCN | —CH$_3$ | —H | —H | NH$_2$C O— | CH$_3$C(CH$_3$)$_2$— | C$_6$H$_5$CC— | —OCH$_3$ | —H | —COOH |
| 202 | —C$_5$H$_{10}$Cl | —C$_4$H$_7$S— | —H | —H | —SCN | —OCH$_3$ | CH$_3$OCOO— | —H | —C$_4$H$_7$S— | —I |
| 203 | —SCN | —CN | —H | —H | —H | C$_{10}$H$_{21}$COO— | —H | —H | —SCN | —OCH$_3$ |
| 204 | NH$_2$CO— | —C$_4$H$_7$S— | —H | —OCH$_3$ | —H | CH$_3$OCOO— | —CH$_2$Cl | —COOH | —CH$_3$ | —H |
| 205 | —SCN | —CN | FC$_6$H$_4$CH$_2$— | CH$_3$OCOO— | —H | C$_6$H$_5$CC— | CH$_3$OCOO— | —H | —H | —C$_6$H$_5$ |
| 206 | —C$_5$H$_{10}$Cl | CH$_3$C(CH$_3$)$_2$— | NH$_2$C O— | —H | FC$_6$H$_4$CH$_2$— | —H | C$_6$H$_5$CC— | C$_{10}$H$_{21}$COO— | —H | —SCN |
| 207 | —NH$_2$ | —OH | —SCN | —H | NH$_2$C O— | —C$_4$H$_7$S— | CH$_3$OCOO— | —OCH$_3$ | —C$_9$H$_{19}$SO$_3$ | —COOH |
| 208 | —NO$_2$ | —I | —CN | —H | —SCN | —H | —H | —H | —H | —C$_6$H$_5$ |
| 209 | NH$_2$CO— | —CH$_3$ | —CN | —H | NH$_2$C O— | CH$_3$C(CH$_3$)$_2$— | —H | —CN | —C$_4$H$_7$S— | —OH |
| 210 | —C$_5$H$_{10}$Cl | —C$_4$H$_7$S— | —H | —H | —CH$_2$Cl | —OCH$_3$ | —OH | —C$_3$H$_5$ | —CH$_3$ | CHC— |
| 211 | —SCN | —CH$_3$ | —H | —H | —C$_9$H$_{19}$SO$_3$ | —F | —OH | —CH$_3$ | —NO$_2$ | C$_6$H$_5$CC— |
| 212 | —H | —CN | —H | —H | —NO$_2$ | —CN | —OH | —CN | —F | —C$_6$H$_5$ |
| 213 | —H | —F | —H | —H | —SCN | —CH$_2$Cl | —OH | —C$_3$H$_5$ | —F | —C$_6$H$_5$ |
| 214 | —H | —CH$_2$Cl | —H | —H | —NH$_2$ | CH$_3$OCOO— | C$_6$H$_5$CC— | —CH$_3$ | —CH$_3$ | —OH |
| 215 | —H | —NO$_2$ | —H | —H | —H | CH$_3$OCOO— | —H | —CH$_3$ | —CH$_3$ | CHC— |
| 216 | —CN | —F | —CH$_2$Cl | —H | —H | —CH$_2$Cl | —H | —OH | —NO$_2$ | —C$_6$H$_5$ |
| 217 | —CH$_2$Cl | —H | —C$_9$H$_{19}$SO$_3$ | —H | —H | —F | —H | —H | —H | —C$_6$H$_5$ |
| 218 | —F | —H | —NO$_2$ | —H | —H | —CN | —CN | —F | —F | —OH |
| 219 | —NO$_2$ | —H | —SCN | —H | —H | CH$_3$OCOO— | —H | —C$_3$H$_5$ | CHC— | CHC— |
| 220 | —F | —H | —NH$_2$ | —H | —H | CH$_3$OCOO— | —OH | —CH$_3$ | —C$_3$H$_5$ | C$_6$H$_5$CC— |
| 221 | —CH$_2$Cl | —H | —OH | —H | —H | —H | —OH | —H | —CH$_3$ | —C$_6$H$_5$ |
| 222 | —CN | —H | —CH$_2$Cl | CH$_2$Cl | —H | —H | —OH | C$_6$H$_5$CC— | —NO$_2$ | —C$_6$H$_5$ |
| 223 | —CH$_2$Cl | —H | —C$_9$H$_{19}$SO$_3$ | CH$_3$OCOO— | —H | —H | —OH | —C$_3$H$_5$ | —F | —C$_6$H$_5$ |
| 224 | —F | —H | —NO$_2$ | —CN | —H | CH$_3$OCOO— | —H | —CH$_3$ | —F | —OH |
| 225 | —NO$_2$ | —H | —SCN | —CH$_2$Cl | —OH | CH$_3$OCOO— | —CH$_3$ | —H | CHC— | CHC— |
| 226 | —F | —H | —NH$_2$ | —H | —C$_4$H$_7$S— | —H | —OH | —H | —C$_3$H$_5$ | C$_6$H$_5$CC— |
| 227 | —H | —H | —OH | —OH | —H | —H | —OH | —H | —CH$_3$ | —C$_6$H$_5$ |
| 228 | —H | —H | —F | —OH | —H | —F | —OH | —F | —NO$_2$ | —C$_6$H$_5$ |
| 229 | —H | —H | —SCN | —F | —H | —CN | —OH | —CN | —F | —OH |
| 230 | —H | —H | —SCN | —CN | —H | CH$_3$OCOO— | —OH | —H | CHC— | CHC— |
| 231 | —H | —H | —H | —H | —H | CH$_3$OCOO— | —OH | —OH | —CH$_3$ | C$_6$H$_5$CC— |
| 232 | —H | —H | —H | —CH$_2$Cl | —H | —H | —OH | —H | —CH$_3$ | —C$_6$H$_5$ |
| 233 | —H | —H | —H | CH$_3$OCOO— | —H | —H | —OH | —H | —CH$_3$ | —C$_6$H$_5$ |
| 234 | —H | —H | —H | —CN | —C$_4$H$_7$S— | —H | —OH | —H | —NO$_2$ | —OH |
| 235 | —H | —H | —H | —H | —C$_9$H$_{19}$SO$_3$ | CH$_3$OCOO— | —C$_9$H$_{19}$SO$_3$ | C$_6$H$_5$CC— | —H | CHC— |
| 236 | —H | —H | —NH$_2$ | —OH | —OH | —H | —OH | —H | —H | C$_6$H$_5$CC— |
| 237 | —H | —H | —OH | —F | —H | —H | —OH | —H | —F | —C$_6$H$_5$ |
| 238 | —F | —H | —F | —CN | —C$_4$H$_7$S— | —H | —H | —F | —CH$_3$ | —C$_6$H$_5$ |
| 239 | —CH$_2$Cl | —H | —SCN | —CH$_3$ | —C$_9$H$_{19}$SO$_3$ | CHC— | —C$_9$H$_{19}$SO$_3$ | —H | —CH$_3$ | —C$_6$H$_5$ |
| 240 | —F | CH$_2$Cl | —SCN | —CH$_2$Cl | —C$_3$H$_5$ | C$_6$H$_5$CC— | —OH | —H | —CH$_2$Cl | CHC— |
| 241 | —F | —H | —H | C$_6$H$_5$CC— | —OH | —CH$_2$Cl | —C$_9$H$_{19}$SO$_3$ | —CN | —CH$_3$ | —C$_6$H$_5$ |
| 242 | —F | —H | —SCN | —OH | —OH | —H | —OH | —H | —CH$_3$ | —H |
| 243 | —CN | —C$_9$H$_{19}$SO$_3$ | —H | —C$_6$H$_5$CC— | —H | —H | —F | —H | —NO$_2$ | —OH |

TABLE 1-continued

Specific examples of the flavone derivatives and flavanone derivatives provided in embodiments of the present invention.

| No. | R$_1$ | R$_2$ | R$_3$ | R$_4$ | R$_5$ | R$_6$ | R$_7$ | R$_8$ | R$_9$ | R$_{10}$ |
|---|---|---|---|---|---|---|---|---|---|---|
| 244 | —CH$_2$Cl | —NO$_2$ | —H | —CN | —H | —H | —OH | —F | —H | —CHC |
| 245 | —F | —SCN | —H | —CH$_2$Cl | —H | —H | —C$_9$H$_{19}$SO$_3$ | —C$_3$H$_5$ | —C$_6$H$_5$CC | —CH$_3$OCOO |
| 246 | —NO$_2$ | —NH$_2$ | —H | —OH | —CH$_3$ | —H | —H | —CN | —F | —C$_6$H$_5$ |
| 247 | —F | —CH$_2$Cl | —H | —OH | —CH$_3$ | —F | —H | —CN | —CH$_3$ | —H |
| 248 | —CH$_2$Cl | —F | —H | —F | —C$_6$H$_5$ | —C$_3$H$_5$ | —H | —OH | —NO$_2$ | —CHC |
| 249 | —CN | —C$_9$H$_{19}$SO$_3$ | —H | —CN | —C$_6$H$_5$CC | —F | —OH | —H | —C$_6$H$_5$CC | —H |
| 250 | —CH$_2$Cl | —NO$_2$ | —H | —CH$_2$Cl | —OH | —H | —H | —H | —H | —CHC |
| 251 | —F | —SCN | —CN | —CH$_3$OCOO | —C$_9$H$_{19}$SO$_3$ | —H | —H | —H | —CH$_2$Cl | —H |
| 252 | —NO$_2$ | —NH$_2$ | —CH$_3$ | —H | —CH$_3$ | —CHC | —H | —H | —C$_3$H$_5$ | —CHC |
| 253 | —F | —OH | —CH$_2$Cl | —H | —C$_4$H$_7$S | —C$_6$H$_5$CC | —H | —H | —H | —H |
| 254 | —CH$_2$Cl | —SCN | —C$_3$H$_5$ | —H | —OH | —CH$_2$Cl | —CH$_2$Cl | —H | —CH$_2$Cl | —C$_6$H$_5$ |
| 255 | —H | —CN | —CN | —H | —C$_9$H$_{19}$SO$_3$ | —H | —CH$_3$O | —H | —H | —H |
| 256 | —F | —OH | —H | —H | —H | —H | —CH$_3$O | —CH$_3$O | —CH$_3$O | —C$_9$H$_{19}$SO$_3$ |
| 257 | —OH | —H | —H | —H | —H | —H | —CH$_3$O | —NH$_2$CO | —NO$_2$ | —CH$_3$O |
| 258 | —C$_3$H$_5$ | —C$_4$H$_7$S | —H | —H | —H | —H | —C$_4$H$_7$S | —NH$_2$CO | —NO$_2$ | —CH$_2$Cl |
| 259 | —CH$_2$Cl | —F | —CN | —H | —H | —H | —C$_4$H$_7$S | —H | —C$_6$H$_5$CC | —CH$_2$Cl |
| 260 | —C$_9$H$_{21}$ | —OH | —CH$_2$Cl | —F | —C$_3$H$_5$ | —F | —H | —C$_9$H$_{19}$SO$_3$ | —H | —NO$_2$ |
| 261 | —C$_6$H$_5$CC | —NO$_2$ | —CH$_2$Cl | —H | —C$_3$H$_5$ | —H | —H | —NH$_2$CO | —NO$_2$ | —NO$_2$ |
| 262 | —H | —H | —H | —H | —CN | —CN | —H | —H | —H | —H |
| 263 | —H | —H | —H | —OH | —CN | —CN | —OH | —H | —NO$_2$ | —NO$_2$ |
| 264 | —H | —NO$_2$ | —H | —OH | —H | —H | —C$_4$H$_7$S | —H | —NO$_2$ | —CH$_2$Cl |
| 265 | —C$_6$H$_5$CC | —H | —H | —OH | —H | —C$_3$H$_5$ | —C$_4$H$_7$S | —H | —NO$_2$ | —H |
| 266 | —H | —H | —H | —H | —H | —C$_3$H$_5$ | —C$_4$H$_7$S | —H | —NO$_2$ | —C$_5$H$_8$Cl |
| 267 | —C$_5$H$_8$Cl | —H | —H | —H | —C$_3$H$_5$ | —C$_3$H$_5$ | —C$_4$H$_7$S | —H | —F | —CH$_2$Cl |
| 268 | —H | —H | —CH$_2$Cl | —H | —H | —H | —C$_4$H$_7$S | —H | —H | —H |
| 269 | —H | —NO$_2$ | —CH$_2$Cl | —H | —CN | —F | —C$_4$H$_7$S | —H | —NO$_2$ | —CH$_2$Cl |
| 270 | —H | —NO$_2$ | —H | —OH | —CN | —H | —C$_4$H$_7$S | —H | —NO$_2$ | —CH$_2$Cl |
| 271 | —H | —NO$_2$ | —H | —OH | —C$_3$H$_5$ | —H | —C$_4$H$_7$S | —C$_6$H$_5$CC | —F | —CH$_2$Cl |
| 272 | —H | —NO$_2$ | —H | —OH | —OH | —H | —C$_4$H$_7$S | —CHC | —H | —CH$_2$Cl |
| 273 | —C$_6$H$_5$CC | —H | —C$_9$H$_{19}$SO$_3$ | —CN | —H | —H | —H | —H | —NO$_2$ | —H |
| 274 | —H | —C$_6$H$_5$CC | —C$_9$H$_{19}$SO$_3$ | —OH | —H | —F | —H | —H | —NO$_2$ | —OH |
| 275 | —C$_6$H$_5$CC | —H | —H | —OH | —H | —H | —FC$_6$H$_4$ | —COOH | —OCH$_2$CH$_3$ | —OH |
| 276 | —C$_9$H$_{19}$SO$_3$ | —H | —H | —H | —NH$_2$CO | —H | —CH$_3$CH$_2$SO$_2$ | —NO$_2$ | —NH$_2$CO | —H |
| 277 | —H | —NO$_2$ | —H | —H | —COOH | —COOH | —C$_6$H$_4$ | —NH$_2$ | —CH═CH$_2$ | —OH |
| 278 | —H | —C$_6$H$_4$Cl | —CH$_3$CO | —NH$_2$CO | —C$_6$H$_5$ | —C$_6$H$_5$ | —CH$_3$CH$_2$SO$_2$ | —C$_6$H$_5$ | —C$_6$H$_4$Cl | —C$_6$H$_5$ |
| 279 | —H | —CN | —FC$_6$H$_4$O | —C$_3$H$_5$ | —CH$_3$CH$_2$CH$_2$SO$_2$ | —CN | —F | —NO$_2$ | —CH$_3$COCH$_2$ | —NH$_2$COCH$_2$ |
| 280 | —H | —NO$_2$ | —F | —NO$_2$ | —CN | —COOH | —FC$_6$H$_4$ | —COOH | —CH═CH$_2$ | —OH |
| 281 | —H | —OH | —CH═CH$_2$ | —H | —C$_6$H$_5$O | —C$_6$H$_5$O | —CH$_3$CH$_2$SO$_2$ | —NH$_2$ | —CH$_3$OCOO | —CH$_3$CH$_2$CO |
| 282 | —H | —SCN | —CH═CH$_2$ | —C$_6$H$_5$O | —COOH | —NH$_2$COCH$_2$ | —F | —C$_6$H$_5$ | —CH$_3$CO | —OH |
| 283 | —H | —COOH | —CH$_2$CH$_2$SO$_3$H | —OCH$_3$ | —OCH$_3$ | —CH$_3$COCH$_2$ | —NH$_2$COCH$_2$ | —SCN | —CH$_3$ | —C$_6$H$_5$ |
| 284 | —H | —NH$_2$ | —CCCH$_3$ | —I | —CH$_3$CH$_3$ | —NH$_2$COCH$_2$ | —NH$_2$ | —C$_6$H$_5$O | —C$_6$H$_5$O | —OH |
| 285 | —H | —OCH$_2$CH$_3$ | —CH$_3$CO | —NH$_2$CO | —CCCH$_3$ | —CH$_3$COCH$_2$ | —C$_6$H$_4$Cl | —SCN | —H | —OH |
| 286 | —H | —CH$_3$ | —NH$_2$COCH$_2$ | —Cl | —Br | —H | —CH$_3$CH$_3$ | —CH$_3$O | —CCCO | —OH |
| 287 | —H | —CCCH$_3$ | —FC$_6$H$_4$O | —CH$_2$CH$_2$SO$_3$H | —OCH$_3$ | —OCH$_3$ | —CH$_3$CO | —OH | —CH$_3$CO | —FC$_6$H$_4$O |
| 288 | —H | —CH═CHCH$_3$ | —I | —CCCH$_3$ | —CCCH$_3$ | —H | —CCCH$_3$ | —H | —H | —C$_6$H$_5$ |
| 289 | —H | —CH$_3$ | —CH$_2$CH$_2$SO$_3$H | —COOH | —OCH$_3$ | —NH$_2$ | —CN | —CCCH$_3$ | —CCCO | —C$_4$H$_7$S |
| 290 | —H | —CH═CHCH$_3$ | —CH$_3$ | —OH | —F | —C$_6$H$_5$ | —C$_4$H$_7$S | —F | —SCN | —C$_6$H$_5$ |
| 291 | —H | —NH$_2$CO | —CH$_2$CH$_2$SO$_3$H | —COOH | —C$_6$H$_4$Cl | —SCN | —CH$_3$CH$_3$ | —CCCH$_3$ | —CH$_3$CO | —C$_4$H$_7$S |
| 292 | —H | —C$_6$H$_5$ | —OCH$_2$CH$_3$ | —F | —C$_4$H$_7$S | —CH$_3$ | —OH | —CCCH$_3$ | —SCN | —NH$_2$CO |

TABLE 1-continued

Specific examples of the flavone derivatives and flavanone derivatives provided in embodiments of the present invention.

| No. | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 293 | —H | $CH_3OCOO$— | —Cl | —$C_4H_7S$ | —$CH_3$ | $CH_3OCOO$— | —OH | $CH_2CH_2SO_3H$ | —COOH | —$OCH_2CH_3$ |
| 294 | —H | $CH_3CH_2COO$— | —$NO_2$ | —$C_6H_5$ | —OH | —$C_6H_5$ | —$C_4H_7S$ | —$CH_3$ | —Cl | —$OCH_2CH_3$ |
| 295 | —H | $CH_3CO$— | —OH | —$CH_3$ | —$NO_2$ | —$CH_3$ | —$NO_2$ | —$C_6H_5O$ | —$OCH_2CH_3$ | —OH |
| 296 | —H | $CH_3CH_2S$— | —OH | —$C_4H_7S$ | —$CH_2CH_2SO_3H$ | —$C_4H_7S$ | —Cl | —$OCH_2CH_3$ | —Cl | —$C_6H_5O$ |
| 297 | —H | —$CH_2CH_2SO_3H$ | —$C_2H_5$ | —$OCH_2CH_3$ | —$NO_2$ | —$CH_3$ | —$NO_2$ | $CH_3OCOO$— | —Cl | —CH=$CH_2$ |
| 298 | —H | —$C_6H_5O$ | —OH | —$OCH_2CH_3$ | —H | —$C_4H_7S$ | —$OCH_2CH_3$ | —$C_4H_7S$ | —CH=$CH_2$ | —H |
| 299 | $CH_3CO$— | —$C_6H_5O$ | —H | $FC_6H_4$— | —H | —COOH | $NH_2CO$— | $CH_3CH_2O$— | —CN | —$C_6H_5$ |
| 300 | $FC_6H_4O$— | —$CH_3O$ | —$C_6H_5O$ | —$C_6H_4Cl$ | —$C_6H_5O$ | —$NO_2$ | —CH=$CH_2$ | $CH_3CH_2O$— | —$CH_2CH_2SO_3H$ | —$CH_2CH_2SO_3H$ |
| 301 | —F | —$CH_3O$ | $NH_2COCH_2$— | —$CH_2CH_2SO_3H$ | $CH_3O$— | —COOH | $CH_3OCOO$— | $CH_3CH_2O$— | —COOH | —CN |
| 302 | —CH=$CH_2$ | —$CH_3O$ | —OH | —F | $CH_3O$— | —$NH_2$ | —$C_6H_4Cl$ | —CH=$CH_2$ | —$C_6H_5O$ | —$C_6H_5O$ |
| 303 | —CH=$CH_2$ | —$CH_3O$ | $CH_3CH_2CO$— | $NH_2COCH_2CH_2$— | —$OCH_3$ | $NH_2CO$— | $CH_3OCOO$— | —CH=$CH_2$ | —$NH_2$ | —COOH |
| 304 | —$CH_2CH_2SO_3H$ | —$CH_3O$ | —$C_4H_7S$ | $FC_6H_4O$— | —$C_6H_5$ | —$C_6H_5$ | $CH_3CO$— | —$CH_2CH_2SO_3H$ | —$C_4H_7S$ | —$OCH_3$ |
| 305 | —CCCH$_3$ | —$CH_3O$ | —OH | —$NH_2$ | $NH_2CO$— | —SCN | —$CH_3$ | —CCCH$_3$ | $CH_3OCOO$— | $NH_2COCH_2$— |
| 306 | $CH_3CO$— | —$CH_3O$ | —OH | —$C_6H_4Cl$ | $CH_3O$— | —SCN | $CH_3CO$— | $CH_3CO$— | $CH_3CH_2O$— | —CCCH$_3$ |
| 307 | $NH_2COCH_2$— | —$CH_3O$ | —OH | —$CH_2CH_3$ | —F | $CH_3O$— | —CH=$CH_2$ | $NH_2CO$— | —F | —$OCH_3$ |
| 308 | $FC_6H_4O$— | —$CH_3O$ | —H | $CH_3CO$— | —I | —OH | —CCCH$_3$ | $FC_6H_4O$— | —H | —Br |
| 309 | —I | —$CH_3O$ | —$C_6H_5$ | —CCCH$_3$ | $CH_2CH_2SO_3H$ | —H | $CH_2CH_2SO_3H$ | —I | —$OCH_3$ | —$OCH_3$ |
| 310 | —$CH_2CH_2SO_3H$ | —$CH_3O$ | —$C_4H_7S$ | —CN | —OH | —H | —SCN | —$CH_3$ | —$NH_2$ | —F |
| 311 | $CH_3O$— | —$NO_2$ | —H | —OH | —COOH | —H | —SCN | —$C_6H_5O$ | —$C_6H_5$ | —$C_6H_4Cl$ |
| 312 | —$OCH_2CH_3$ | —$C_6H_4Cl$ | —$OCH_2CH_3$ | —OH | —F | —H | —COOH | —$OCH_2CH_3$ | —SCN | —$C_4H_7S$ |
| 313 | —Cl | —CN | —$OCH_2CH_3$ | —$C_6H_5$ | —I | —H | —Cl | —$NO_2$ | —$CH_3$ | —$CH_3$ |
| 314 | —$NO_2$ | —OH | —$C_6H_5O$ | —$C_4H_7S$ | —$C_6H_5$ | —H | —Cl | —OH | $CH_3CH_2O$— | —OH |
| 315 | —OH | —SCN | —OH | —$CH_3$ | —$OCH_2CH_3$ | —H | —$OCH_3$ | —COOH | —$C_6H_5$ | —$NO_2$ |
| 316 | —$C_6H_5$ | —COOH | —$C_6H_5O$ | —$NO_2$ | —$OCH_2CH_3$ | —H | —$C_6H_5O$ | —OH | —$C_4H_7S$ | $CH_2CH_2O$— |
| 317 | —OH | —$NH_2$ | —CH=$CH_2$ | —$CH_3$ | —$OCH_2CH_3$ | —H | —CH=$CH_2$ | —$C_6H_5$ | —$CH_2CH_2SO_3H$ | —$NO_2$ |
| 318 | $NH_2COCH_2$— | —$OCH_2CH_3$ | $FC_6H_4O$— | —$NO_2$ | $NH_2CO$— | —H | —$CH_2CH_2SO_3H$ | $CH3CO$— | —CN | —Cl |
| 319 | $FC_6H_4O$— | —$CH_3$ | —$C_6H_4Cl$ | —H | —CH=$CH_2$ | —H | —$C_6H_5O$ | —COOH | —F | —$C_2H_5$ |
| 320 | $CH_3O$— | —H | $FC_6H_4O$— | —$C_6H_5O$ | —$C_6H_4Cl$ | —H | —CN | —$NO_2$ | —COOH | $FC_6H_4O$— |
| 321 | $FC_6H_4O$— | —$NO_2$ | $NH_2COCH_2CH_2$— | $CH_3CO$— | $NH_2CO$— | —H | $C_6H_5O$— | —$NH_2$ | —COOH | —$C_6H_5$ |
| 322 | —CH=$CH_2$ | —$C_6H_4Cl$ | —F | $C_6H_5O$— | —CH=$CH_2$ | —H | —CN | $NH_2CO$— | —$NH_2$ | —$C_4H_7S$ |
| 323 | —CH=$CH_2$ | —CN | $NH_2COCH_2$— | $CH_3CO$— | —$C_6H_4Cl$ | —H | —COOH | —$C_6H_5$ | —SCN | —H |
| 324 | —$CH_2CH_2SO_3H$ | —OH | $FC_6H_4O$— | —$OCH_3$ | $CH_3OCOO$— | —H | —$OCH_3$ | —SCN | —$CH_3$ | —$OCH_2CH_3$ |
| 325 | —CCCH$_3$ | —SCN | —$C_6H_5$ | —F | $CH_3O$— | —H | —$CH_3$ | $CH_3CO$— | $CH_3OCOO$— | —OH |
| 326 | $CH_3CO$— | —COOH | —$NH_2$ | —$C_4H_7S$ | $CH_3O$— | —H | —$NO_2$ | $CH_3OCOO$— | —$C_6H_5$ | $NH_2CO$— |
| 327 | $NH_2COCH_2$— | —$NH_2$ | —$C_6H_4Cl$ | —$C_6H_5$ | —H | —H | —OH | —$C_4H_7S$ | $NH_2CO$— | —$OCH_2CH_3$ |
| 328 | $FC_6H_4O$— | —$OCH_2CH_3$ | —$CH_2CH_3$ | —Cl | —CCCH$_3$ | —H | —OH | $CH_3OCOO$— | $CH_3CH_2CO$— | —$OCH_2CH_3$ |
| 329 | —I | —$CH_3$ | $CH_3CO$— | —$C_4H_7S$ | $CH_3CO$— | —H | —$CH_3$ | —$C_6H_5O$ | —$CH_3$ | —OH |
| 330 | —$CH_2CH_2SO_3H$ | —CCCH$_3$ | —CCCH$_3$ | —$OCH_2CH_3$ | —CCCH$_3$ | $CH_2CH_2SO_3H$ | —$CH_2CH_2SO_3H$ | —$CH_2CH_2SO_3H$ | —$CH_2CH_2SO_3H$ | —$C_6H_5$ |
| 331 | —$CH_3$ | —CH=CHCH$_3$ | —F | —$CCCH_3$ | —OH | —H | —F | —$CH_3$ | —F | —H |
| 332 | —$OCH_2CH_3$ | $NH_2CO$— | —OH | —COOH | —COOH | —H | —$C_6H_4Cl$ | —COOH | —COOH | —$C_6H_5$ |
| 333 | —Cl | $CH_3OCOO$— | —OH | —F | $CH_3CO$— | —H | —$C_4H_7S$ | —CCCH$_3$ | —COOH | —$C_4H_7S$ |
| 334 | —$NO_2$ | $CH_3CH_2COO$— | —$C_4H_7S$ | —$C_4H_7S$ | $CH_3CO$— | —H | —$CH_3$ | —$CH_2CH_2SO_3H$ | $CH_3OCOO$— | —H |
| 335 | —OH | $CH_3CO$— | —Cl | —$C_6H_5$ | —Cl | —H | —OH | —$C_6H_5O$ | —$C_6H_5$ | —$OCH_2CH_3$ |
| 336 | —OH | $CH_3CH_2S$— | —$NO_2$ | —Cl | —COOH | —H | —$NO_2$ | —$OCH_2CH_3$ | —$CH_3$ | —$OCH_2CH_3$ |
| 337 | —$C_6H_5$ | —$CH_2CH_2SO_3H$ | —$CH_3$ | —$OCH_2CH_3$ | —Cl | —H | —Cl | $CH_3OCOO$— | —$C_4H_7S$ | —OH |
| 338 | —OH | —$C_6H_5O$ | —$NO_2$ | —$OCH_2CH_3$ | —Cl | —H | —$OCH_2CH_3$ | —$C_4H_7S$ | —$CH_2CH_2SO_3H$ | —CH=$CH_2$ |
| 339 | —$CH_2CH_2SO_3H$ | —$C_6H_5O$ | —OH | —$CH_3O$ | —CH=$CH_2$ | —SCN | —$NO_2$ | —$CH_2CH_2SO_3H$ | $FC_6H_4O$— | —$OCH_3$ |
| 340 | —CCCH$_3$ | —$CH_3$ | —OH | —$CH_3O$ | —I | —$C_6H_5$ | $NH_2CO$— | —$CH_3$ | —$NH_2$ | —H |
| 341 | $CH_3CO$— | —$C_6H_5O$ | —OH | —$CH_3O$ | $NH_2CO$— | —SCN | $CH_3CH_2CO$— | $CH_3CO$— | —$C_6H_4Cl$ | —CCCH$_3$ |

TABLE 1-continued

Specific examples of the flavone derivatives and flavanone derivatives provided in embodiments of the present invention.

| No. | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 342 | NH$_2$COCH$_2$— | H | FC$_6$H$_4$O— | CH$_3$O— | —Cl | CH$_3$CO— | H | NH$_2$COCH$_2$— | —CH$_2$CH$_3$ | —CCCH$_3$ |
| 343 | FC$_6$H$_4$O— | —CCCH$_3$ | —H | CH$_3$O— | —CH$_2$CH$_2$SO$_3$H | —OH | —OCH$_3$ | FC$_6$H$_4$O— | CH$_3$CO— | —Br |
| 344 | —I | CH$_3$CO— | —C$_6$H$_5$ | CH$_3$O— | —CCCH$_3$ | H | —NH$_2$ | —I | —CCCH$_3$ | —OCH$_3$ |
| 345 | —CH$_2$CH$_2$SO$_3$H | —SCN | —C$_4$H$_7$S | CH$_3$O— | —OH | —CCCH$_3$ | —C$_6$H$_5$ | —CH$_2$CH$_2$SO$_3$H | —CN | —F |
| 346 | —CH$_3$ | CH$_3$CO— | —H | CH$_3$O— | —COOH | —F | —SCN | —CH$_3$ | —C$_4$H$_7$S | —C$_6$H$_4$Cl |
| 347 | —OCH$_2$CH$_3$ | —SCN | NH$_2$CO— | CH$_3$O— | —F | —CCCH$_3$ | —CH$_3$ | —OCH$_2$CH$_3$ | —OH | —C$_4$H$_7$S |
| 348 | —H | —H | —H | —H | —NO$_2$ | —H | CHC— | —H | —H | —H |
| 349 | —C$_4$H$_7$S | —NH$_2$ | —H | NH$_2$CO— | —H | —H | —OH | —H | —H | —H |
| 350 | —H | —COOH | —H | —H | CHC— | C$_2$H$_5$O— | —H | —H | —NO$_2$ | —H |
| 351 | —H | —H | —H | —H | —H | —H | —OH | NH$_2$CO— | —C$_3$H$_5$ | —H |
| 352 | —H | —H | —H | —H | —H | —H | CH$_2$CH— | NH$_2$CO— | —CH$_3$ | —H |
| 353 | —H | —H | —H | —H | —H | —H | —H | —H | —H | —OH |

In Table 1, the structural formula of —$C_5H_{10}Cl$ is —$CH_2CH_2CH_2CH_2CH_2Cl$; —$C_{20}H_{41}$ is linear eicosyl group; the structural formula of —$C_3H_5$ is —$CH=CHCH_3$; the structural formula of —$C_4H_7S$ is

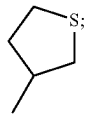

the structural formula of —$C_4H_9SO_3$ is —$CH_2CH_2CH_2CH_2SO_3H$; the structural formula of $C_7H_{15}CHCH$— is $CH_3(CH_2)_6CH=CH$—; —$C_7H_{15}$ is n-heptane; the structural formula of —$C_4H_8N$ is

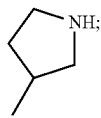

$C_5H_{11}O$— is pentyloxy group; —$C_{20}H_{40}Cl$ is chloro-linear eicosyl group; —$C_8H_{15}Cl_2$ is 2-chloro-straight-chain-octane group; in $C_5H_{11}NH_2CO$—, $C_5H_{11}$ is a linear alkyl group; the structural formula of —$NO_2C_2H_2S$ is

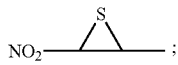

in $C_{10}H_{21}CH_2O$—, $C_{10}H_{21}$ is a linear alkyl group; in $C_{10}H_{21}COO$—, $C_{10}H_{21}$ is a branched alkyl group; in $C_5H_{11}CO$—, $C_5H_{11}$ is a linear alkyl group; in $C_4H_9SO_2$—, $C_4H_9$ is isobutyl; in $C_8H_{17}S$—, $C_8H_{17}$ is branched alkyl group; in —$C_8H_{17}SO_3$, $C_8H_{17}$ is a linear alkyl group; in $C_{15}H_{31}S$—, $C_{15}H_{31}$ is a linear alkyl group; —$C_4H_8Cl$ is chloro-n-butyl; in $C_6H_{13}CC$—, $C_6H_{13}$ is n-hexyl; the structural formula of —$C_5H_5N$ is

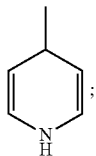

the structural formula of —$C_5H_9$ is —$CH=CHCH_2CH_2CH_3$; —$C_{17}H_{35}$ is linear alkyl group; in —$C_{11}H_{21}SO_3$, $C_{11}H_{21}$ is a branched alkyl group; in $C_{11}H_{21}SO_2$—, $C_{11}H_{21}$ is a linear alkyl group; in $BrNO_2C_{15}H_{29}S$—, $BrNO_2C_{15}H_{29}$ is a linear alkyl group; the structural formula of —$C_5H_9S$ is

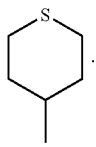

In Table 1, the groups may be combined with the skeletal structural shown in Formula (I) to provide flavone deriva-tives having specific structure; the groups may be combined with the skeletal structural shown in Formula (II) to provide flavanone derivatives having specific structure. Embodiments of the present invention will not make particular restrictions on the above.

In embodiments of the present invention, the pro-drugs of the flavone derivatives shown by the structure of Formula (I) or the flavanone derivatives shown by the structure of Formula (II) may both be pro-drugs well known to a person skilled in the art. Such pro-drug is, for example, one that is formed from the flavone derivatives shown in Formula (I) or the flavanone derivatives shown in Formula (II) and a carrier, or a phosphate ester compound formed by flavone derivatives shown in Formula (I) or the flavanone derivatives shown in Formula (II), or other compounds which may be converted in vivo to the flavone derivatives shown by the structure of Formula (I) or the flavanone derivatives shown by the structure of Formula (II). In embodiments of the present invention, the metabolites of the flavone derivatives shown by the structure of Formula (I) or the flavanone derivatives shown by the structure of Formula (II) include metabolites that are well known to a person skilled in the art, such as the metabolites produced from the flavone derivatives shown by the structure of Formula (I) or the flavanone derivatives shown by the structure of Formula (II) via metabolism in animal bodies.

In embodiments of the present invention, the pharmaceutically acceptable salts of the flavone derivatives shown by the structure of Formula (I) or the flavanone derivatives shown by the structure of Formula (II) may include sodium salts, potassium salts, calcium salts and the like of the flavone derivatives shown by the structure of Formula (I) or the flavanone derivatives shown by the structure of Formula (II).

Furthermore, embodiments of the present invention preferably discloses the flavone derivatives shown by the structure of Formula (III), the flavanone derivatives shown by the structure of Formula (V), or pharmaceutically acceptable salts thereof

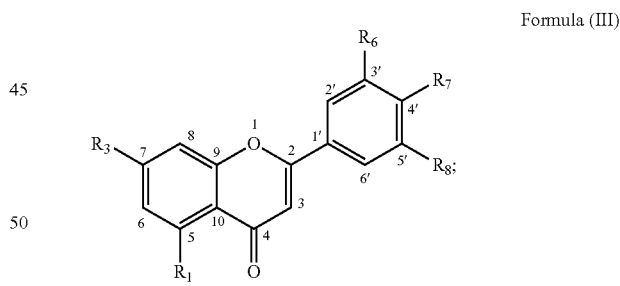

Formula (III)

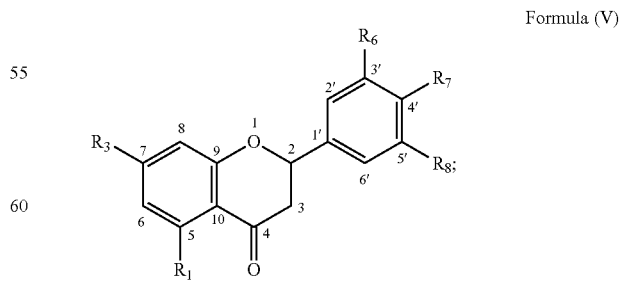

Formula (V)

Wherein $R_1$, $R_3$, $R_6$, $R_7$ and $R_8$ may be the same or different, and are independently selected from hydrogen (—H), nitro group (—$NO_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group, wherein the hydrogen (—H), nitro group (—NO$_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group have the same meanings with the groups described above, and embodiments of the present invention does not repeat them here.

In embodiments of the present invention, the flavone derivative shown by the structure of Formula (III) or the flavanone derivatives shown by the structure of Formula (V) include, but are not limited within the compounds listed in Table 2:

TABLE 2 the compounds of the flavone derivatives or flavanone derivatives in particular preparing embodiments as provided by embodiments of the present invention.

| Serial | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 354 | —OCH$_3$ | —H | —OCH$_3$ | —H | —H | —OCH$_3$ | —OCH$_3$ | —OCH$_3$ | —H | —H |
| 355 | —CN | —H | —F | —H | —H | —OH | —SCN | —NH$_2$ | —H | —H |
| 356 | —NO$_2$ | —H | C$_6$H$_5$CC— | —H | —H | —OH | C$_6$H$_5$O— | —C$_{20}$H$_{40}$Cl | —H | —H |
| 357 | —C$_4$H$_7$S | —H | NH$_2$CO— | —H | —H | —NH$_2$ | CH$_3$CH$_2$— | —CHCH$_2$ | —H | —H |
| 358 | —C$_6$H$_{11}$ | —H | —C$_6$H$_5$ | —H | —H | CH$_3$CH$_2$— | —C$_5$H$_{10}$Cl | —C$_3$H$_5$ | —H | —H |
| 359 | CH$_3$CH$_2$— | —H | —C$_5$H$_{10}$Cl | —H | —H | —C$_5$H$_{11}$ | C$_6$H$_5$CH$_2$— | —OH | —H | —H |
| 360 | —C$_3$H$_5$ | —H | C$_6$H$_5$CH$_2$— | —H | —H | —NO$_2$ | —CHCH$_2$ | —CN | —H | —H |
| 361 | —OH | —H | —COOH | —H | —H | —C$_{20}$H$_{41}$ | —CCH | —F | —H | —H |
| 362 | —C$_3$H$_6$ | —H | CH$_3$CH$_2$— | —H | —H | —C$_{20}$H$_{40}$Cl | —C$_5$H$_{11}$ | —C$_6$H$_5$ | —H | —H |
| 363 | —COOH | —H | —C$_3$H$_5$ | —H | —H | —CN | —F | —COOH | —H | —H |
| 364 | —I | —H | —CH$_2$CH$_2$SO$_3$H | —H | —H | —CONH$_2$ | —COOH | —C$_3$H$_7$ | —H | —H |
| 365 | —SCN | —H | —OH | —H | —H | —OH | —OH | —C$_{20}$H$_{40}$Cl | —H | —H |
| 366 | —OH | —H | —OH | —H | —H | —COOH | —OCH$_3$ | —OH | —H | —H |
| 367 | —NO$_2$ | —H | —OH | —H | —H | —C$_6$H$_5$ | —C$_4$H$_7$S | —C$_3$H$_7$ | —H | —H |
| 368 | —C$_4$H$_8$N | —H | —SCN | —H | —H | CH$_3$CH$_2$— | C$_6$H$_5$CO— | —NO$_2$ | —H | —H |
| 369 | —NH$_2$ | —H | —C$_4$H$_8$N | —H | —H | —SCN | —OCH$_3$ | —CH$_2$CH$_2$SO$_3$H | —H | —H |
| 370 | —CCH | —H | —NO$_2$ | —H | —H | —C$_4$H$_7$S | —CH$_2$CH$_2$SO$_3$H | —CCH | —H | —H |
| 371 | —CH$_2$CH$_2$SO$_3$H | —H | —I | —H | —H | —C$_3$H$_5$ | C$_{10}$H$_{21}$CH$_2$O— | —C$_{20}$H$_{40}$Cl | —H | —H |
| 372 | C$_6$H$_5$CH$_2$— | —H | —C$_3$H$_5$ | —H | —H | —CH$_2$CH$_2$SO$_3$H | —CH$_3$ | —OCH$_3$ | —H | —H |
| 373 | —OCH$_3$ | —H | —CN | —H | —H | —NH$_2$ | —OH | —F | —H | —H |
| 374 | —SCN | —H | —NO$_2$ | —H | —H | —C$_{20}$H$_{40}$Cl | —OH | C$_6$H$_5$CC— | —H | —H |
| 375 | C$_6$H$_5$O— | —H | —C$_4$H$_7$S | —H | —H | —CHCH$_2$ | —NH$_2$ | NH$_2$CO— | —H | —H |
| 376 | CH$_3$CH$_2$— | —H | —C$_6$H$_{11}$ | —H | —H | —C$_3$H$_5$ | CH$_3$CH$_2$— | —C$_6$H$_5$ | —H | —H |
| 377 | —C$_5$H$_{10}$Cl | —H | CH$_3$CH$_2$— | —H | —H | —OH | —C$_5$H$_{11}$ | —C$_5$H$_{10}$Cl | —H | —H |
| 378 | C$_6$H$_5$CH$_2$— | —H | —C$_3$H$_5$ | —H | —H | —CN | —NO$_2$ | C$_6$H$_5$CH$_2$— | —H | —H |
| 379 | —CHCH$_2$ | —H | —OH | —H | —H | —F | —C$_{20}$H$_{41}$ | —COOH | —H | —H |
| 380 | —CCH | —H | —C$_3$H$_6$ | —H | —H | —C$_6$H$_5$ | —C$_{20}$H$_{40}$Cl | CH$_3$CH$_2$— | —H | —H |
| 381 | —C$_5$H$_{11}$ | —H | —COOH | —H | —H | —COOH | —CN | —C$_3$H$_5$ | —H | —H |
| 382 | —F | —H | —I | —H | —H | —C$_3$H$_7$ | —CONH$_2$ | —CH$_2$CH$_2$SO$_3$H | —H | —H |
| 383 | —COOH | —H | —SCN | —H | —H | —C$_{20}$H$_{40}$Cl | —OH | —OH | —H | —H |
| 384 | —OH | —H | —OH | —H | —H | —OH | —COOH | —OH | —H | —H |
| 385 | —OCH$_3$ | —H | —NO$_2$ | —H | —H | —C$_3$H$_7$ | —C$_6$H$_5$ | —OH | —H | —H |
| 386 | —C$_4$H$_7$S | —H | —C$_4$H$_8$N | —H | —H | —NO$_2$ | CH$_3$CH$_2$— | —SCN | —H | —H |
| 387 | C$_6$H$_5$CO— | —H | —NH$_2$ | —H | —H | —CH$_2$CH$_2$SO$_3$H | —SCN | —C$_4$H$_8$N | —H | —H |
| 388 | —OCH$_3$ | —H | —CCH | —H | —H | —CCH | —C$_4$H$_7$S | —NO$_2$ | —H | —H |
| 389 | —CH$_2$CH$_2$SO$_3$H | —H | —CH$_2$CH$_2$SO$_3$H | —H | —H | —C$_{20}$H$_{40}$Cl | —C$_3$H$_5$ | —I | —H | —H |
| 390 | C$_{10}$H$_{21}$CH$_2$O— | —H | C$_6$H$_5$CH$_2$— | —H | —H | —OCH$_3$ | —CH$_2$CH$_2$SO$_3$H | —C$_3$H$_5$ | —H | —H |
| 391 | —CH$_3$ | —H | —H | —H | —H | C$_6$H$_5$O— | —H | —NO$_2$ | —H | —H |
| 392 | C$_6$H$_5$CC— | —H | —H | —H | —H | CH$_3$CH$_2$— | —H | —C$_4$H$_7$S | —H | —H |
| 393 | NH$_2$CO— | —H | —H | —H | —H | —C$_5$H$_{10}$Cl | —H | —C$_6$H$_{11}$ | —H | —H |
| 394 | —C$_6$H$_5$ | —H | —H | —H | —H | C$_6$H$_5$CH$_2$— | —H | CH$_3$CH$_2$— | —H | —H |
| 395 | —C$_5$H$_{10}$Cl | —H | —H | —H | —H | —CHCH$_2$ | —H | —C$_3$H$_5$ | —H | —H |
| 396 | C$_6$H$_5$CH$_2$— | —H | —H | —H | —H | —CCH | —H | —OH | —H | —H |
| 397 | —COOH | —H | —H | —H | —H | —C$_5$H$_{11}$ | —H | —C$_3$H$_6$ | —H | —H |
| 398 | CH$_3$CH$_2$— | —H | —H | —H | —H | —F | —H | —COOH | —H | —H |
| 399 | —C$_3$H$_5$ | —H | —H | —H | —H | —COOH | —H | —I | —H | —H |
| 400 | —CH$_2$CH$_2$SO$_3$H | —H | —H | —H | —H | —OH | —H | —SCN | —H | —H |
| 401 | —OH | —H | —H | —H | —H | —OCH$_3$ | —H | —OH | —H | —H |
| 402 | —OH | —H | —H | —H | —H | —C$_4$H$_7$S | —H | —NO$_2$ | —H | —H |
| 403 | —OH | —H | —H | —H | —H | —SCN | —H | —C$_4$H$_8$N | —H | —H |

In Table 2, —C$_{20}$H$_{41}$ is a linear eicosyl group; the structural formula of —C$_3$H$_5$ is —CH═CHCH$_3$; the structural formula of —C$_4$H$_7$S is

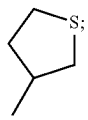

—C$_5$H$_{11}$ is n-pentyl; the structural formula of —C$_4$H$_8$N is

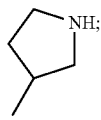

—C$_{20}$H$_{40}$Cl is a chloro-linear-eicosyl group; —C$_6$H$_{11}$ is n-octenyl group.

In embodiments of the present invention, when R$_2$, R$_4$, R$_5$, R$_9$ and R$_{10}$ are —H respectively in the compound shown by the structure of Formula (I), said compound represents the structure of Formula (III); when R$_2$, R$_4$, R$_5$, R$_9$ and R$_{10}$ are —H respectively in the compound shown by the structure of Formula (II), said compound represents the structure of Formula (V). In Table 2, flavone derivatives with particular structures are obtained when combining R$_1$, R$_3$, R$_6$, R$_7$ and R$_8$ groups with the skeletal structure shown by the structure of Formula (III), and flavanone derivatives with particular structures are obtained when combining R$_1$, R$_3$, R$_6$, R$_7$ and R$_8$ groups with the skeletal structure shown by the structure of Formula (V). Embodiments of the present invention does not make particular restrictions on the above.

Furthermore, embodiments of the present invention preferably discloses flavanone derivatives shown by the structure of general formula (IV), flavone derivatives shown by the structure of general formula (VI), or pharmaceutically acceptable salts thereof.

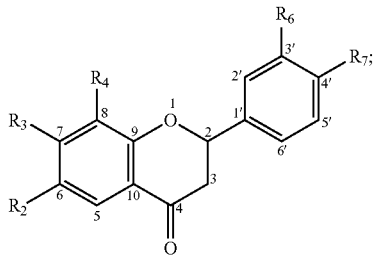

Formula (IV)

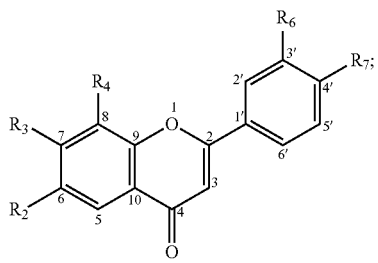

Formula (VI)

wherein R$_2$, R$_3$, R$_4$, R$_6$ and R$_7$ may be the same or different, and are independently selected from hydrogen (—H), nitro group (—NO$_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group, wherein the hydrogen (—H), nitro group (—NO$_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group have the same meanings with the groups described above, and embodiments of the present invention does not repeat them here.

In embodiments of the present invention, the flavanone derivatives shown by the structure of formula (IV) or the flavone derivatives shown by the structure of (VI) include, but are not limited within the compounds listed in Table 3.

TABLE 3 the compounds of the flavone derivatives or flavanone derivatives in particular preparing embodiments as provided by embodiments of the present invention.

| Serial | R$_1$ | R$_2$ | R$_3$ | R$_4$ | R$_5$ | R$_6$ | R$_7$ | R$_8$ | R$_9$ | R$_{10}$ |
|---|---|---|---|---|---|---|---|---|---|---|
| 404 | —H | —OCH$_3$ | —OCH$_3$ | —OCH$_3$ | —H | —OCH$_3$ | —OCH$_3$ | —H | —H | —H |
| 405 | —H | —NH$_2$ | —F | —CN | —H | —OH | —SCN | —H | —H | —H |
| 406 | —H | —C$_{20}$H$_{40}$Cl | C$_6$H$_5$CC— | —NO$_2$ | —H | —OH | C$_6$H$_5$O— | —H | —H | —H |
| 407 | —H | —CHCH$_2$ | NH$_2$CO— | —C$_4$H$_7$S | —H | —NH$_2$ | CH$_3$CH$_2$— | —H | —H | —H |
| 408 | —H | —C$_3$H$_5$ | —C$_6$H$_5$ | —C$_6$H$_{11}$ | —H | CH$_3$CH$_2$— | —C$_5$H$_{10}$Cl | —H | —H | —H |
| 409 | —H | —OH | —C$_5$H$_{10}$Cl | CH$_3$CH$_2$— | —H | —C$_5$H$_{11}$ | C$_6$H$_5$CH$_2$— | —H | —H | —H |
| 410 | —H | —CN | C$_6$H$_5$CH$_2$— | —C$_3$H$_5$ | —H | —NO$_2$ | —CHCH$_2$ | —H | —H | —H |

TABLE 3-continued the compounds of the flavone derivatives or flavanone derivatives in particular preparing embodiments as provided by embodiments of the present invention.

| Serial | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 411 | —H | —F | —COOH | —OH | —H | —$C_{20}H_{41}$ | —CCH | —H | —H | —H |
| 412 | —H | —$C_6H_5$ | $CH_3CH_2$— | —$C_3H_6$ | —H | —$C_{20}H_{40}Cl$ | —$C_5H_{11}$ | —H | —H | —H |
| 413 | —H | —COOH | —$C_3H_5$ | —COOH | —H | —CN | —F | —H | —H | —H |
| 414 | —H | —$C_3H_7$ | —$CH_2CH_2SO_3H$ | —I | —H | —$CONH_2$ | —COOH | —H | —H | —H |
| 415 | —H | —$C_{20}H_{40}Cl$ | —OH | —SCN | —H | —OH | —OH | —H | —H | —H |
| 416 | —H | —OH | —OH | —OH | —H | —COOH | —$OCH_3$ | —H | —H | —H |
| 417 | —H | —$C_3H_7$ | —OH | —$NO_2$ | —H | —$C_6H_5$ | —$C_4H_7S$ | —H | —H | —H |
| 418 | —H | —$NO_2$ | —SCN | —$C_4H_8N$ | —H | $CH_3CH_2$— | $C_6H_5CO$— | —H | —H | —H |
| 419 | —H | —$CH_2CH_2SO_3H$ | —$C_4H_8N$ | —$NH_2$ | —H | —SCN | —$OCH_3$ | —H | —H | —H |
| 420 | —H | —CCH | —$NO_2$ | —CCH | —H | —$C_4H_7S$ | —$CH_2CH_2SO_3H$ | —H | —H | —H |
| 421 | —H | —$C_{20}H_{40}Cl$ | —I | —$CH_2CH_2SO_3H$ | —H | —$C_3H_5$ | $C_{10}H_{21}CH_2O$— | —H | —H | —H |
| 422 | —H | —$OCH_3$ | —$C_3H_5$ | $C_6H_5CH_2$— | —H | —$CH_2CH_2SO_3H$ | —$CH_3$ | —H | —H | —H |
| 423 | —H | —F | —CN | —$OCH_3$ | —H | —$NH_2$ | —OH | —H | —H | —H |
| 424 | —H | $C_6H_5CC$— | —$NO_2$ | —SCN | —H | —$C_{20}H_{40}Cl$ | —OH | —H | —H | —H |
| 425 | —H | $NH_2CO$— | —$C_4H_7S$ | $C_6H_5O$— | —H | —$CHCH_2$ | —$NH_2$ | —H | —H | —H |
| 426 | —H | —$C_6H_5$ | —$C_6H_{11}$ | $CH_3CH_2$— | —H | —$C_3H_5$ | $CH_3CH_2$— | —H | —H | —H |
| 427 | —H | —$C_5H_{10}Cl$ | $CH_3CH_2$— | —$C_5H_{10}Cl$ | —H | —OH | —$C_5H_{11}$ | —H | —H | —H |
| 428 | —H | $C_6H_5CH_2$— | —$C_3H_5$ | $C_6H_5CH_2$— | —H | —CN | —$NO_2$ | —H | —H | —H |
| 429 | —H | —COOH | —OH | —$CHCH_2$ | —H | —F | —$C_{20}H_{41}$ | —H | —H | —H |
| 430 | —H | $CH_3CH_2$— | —$C_3H_6$ | —CCH | —H | —$C_6H_5$ | —$C_{20}H_{40}Cl$ | —H | —H | —H |
| 431 | —H | —$C_3H_5$ | —COOH | —$C_5H_{11}$ | —H | —COOH | —CN | —H | —H | —H |
| 432 | —H | —$CH_2CH_2SO_3H$ | —I | —F | —H | —$C_3H_7$ | —$CONH_2$ | —H | —H | —H |
| 433 | —H | —OH | —SCN | —COOH | —H | —$C_{20}H_{40}Cl$ | —OH | —H | —H | —H |
| 434 | —H | —OH | —OH | —OH | —H | —OH | —COOH | —H | —H | —H |
| 435 | —H | —OH | —$NO_2$ | —$OCH_3$ | —H | —$C_3H_7$ | —$C_6H_5$ | —H | —H | —H |
| 436 | —H | —SCN | —$C_4H_8N$ | —$C_4H_7S$ | —H | —$NO_2$ | $CH_3CH_2$— | —H | —H | —H |
| 437 | —H | —$C_4H_8N$ | —$NH_2$ | $C_6H_5CO$— | —H | —$CH_2CH_2SO_3H$ | —SCN | —H | —H | —H |
| 438 | —H | —$NO_2$ | —CCH | —$OCH_3$ | —H | —CCH | —$C_4H_7S$ | —H | —H | —H |
| 439 | —H | —I | —$CH_2CH_2SO_3H$ | —$CH_2CH_2SO_3H$ | —H | —$C_{20}H_{40}Cl$ | —$C_3H_5$ | —H | —H | —H |
| 440 | —H | —$C_3H_5$ | $C_6H_5CH_2$— | $C_{10}H_{21}CH_2O$— | —H | —$OCH_3$ | —$CH_2CH_2SO_3H$ | —H | —H | —H |
| 441 | —H | —$NO_2$ | —H | —$CH_3$ | —H | $C_6H_5O$— | —H | —H | —H | —H |
| 442 | —H | —$C_4H_7S$ | —H | $C_6H_5CC$— | —H | $CH_3CH_2$— | —H | —H | —H | —H |
| 443 | —H | —$C_6H_{11}$ | —H | $NH_2CO$— | —H | —$C_5H_{10}Cl$ | —H | —H | —H | —H |
| 444 | —H | $CH_3CH_2$— | —H | —$C_6H_5$ | —H | $C_6H_5CH_2$— | —H | —H | —H | —H |
| 445 | —H | —$C_3H_5$ | —H | —$C_5H_{10}Cl$ | —H | —$CHCH_2$ | —H | —H | —H | —H |
| 446 | —H | —OH | —H | $C_6H_5CH_2$— | —H | —CCH | —H | —H | —H | —H |
| 447 | —H | —$C_3H_6$ | —H | —COOH | —H | —$C_5H_{11}$ | —H | —H | —H | —H |
| 448 | —H | —COOH | —H | $CH_3CH_2$— | —H | —F | —H | —H | —H | —H |
| 449 | —H | —I | —H | —$C_3H_5$ | —H | —COOH | —H | —H | —H | —H |
| 450 | —H | —SCN | —H | —$CH_2CH_2SO_3H$ | —H | —OH | —H | —H | —H | —H |
| 451 | —H | —OH | —H | —OH | —H | —$OCH_3$ | —H | —H | —H | —H |
| 452 | —H | —$NO_2$ | —H | —OH | —H | —$C_4H_7S$ | —H | —H | —H | —H |
| 453 | —H | —$C_4H_8N$ | —H | —OH | —H | —SCN | —H | —H | —H | —H |

In Table 3, —$C_{20}H_{41}$ is a linear eicosyl group; the structural formula of —$C_3H_5$ is —CH=$CHCH_3$; the structural formula of —$C_4H_7S$ is

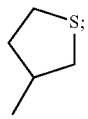

—$C_5H_{11}$ is n-pentyl; the structural formula of —$C_4H_8N$ is

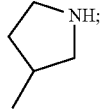

—$C_{20}H_{40}Cl$ is a chloro-linear eicosyl group; —$C_6H_{11}$ is n-octenyl group.

In embodiments of the present invention, when $R_1$, $R_5$, $R_8$, $R_9$ and $R_{10}$ are —H respectively in the compound shown by the structure of Formula (II), said compound represents the structure of Formula (IV); when $R_1$, $R_5$, $R_8$, $R_9$ and $R_{10}$ are —H respectively in the compound shown by the structure of Formula (I), said compound represents the structure of Formula (V). In Table 3, flavanone derivatives with particular structures are obtained when combining $R_2$, $R_3$, $R_4$, $R_6$ and $R_7$ groups with the skeletal structure shown by the structure of Formula (IV), and flavone derivatives with particular structures are obtained when combining $R_2$, $R_3$, $R_4$, $R_6$ and $R_7$ groups with the skeletal structure shown by the structure of Formula (VI). Embodiments of the present invention does not make particular restrictions on the above.

Furthermore, embodiments of the present invention preferably discloses flavone derivatives shown by the structure of general formula (VII), or pharmaceutically acceptable salts thereof

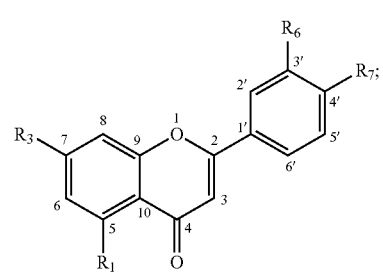

Formula (VII)

Wherein $R_1$, $R_3$, $R_6$ and $R_7$ may be the same or different, and are independently selected from hydrogen (—H), nitro group (—NO$_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group, wherein the hydrogen (—H), nitro group (—NO$_2$), halogen (—X), cyano group (—CN), hydroxyl group (—OH), thiocyanate group (—SCN), carboxyl group (—COOH), amino group (—NH$_2$), alkoxy group or substituted alkoxy group, alkyl group or substituted alkyl group, alkynyl group or substituted alkynyl group, alkenyl group or substituted alkenyl group, amide group, aryl group or substituted aryl group, carbonic ester group, ester group, acyl group, thioether group, sulfonyl group, a group including a carbon-nitrogen double bond, aryloxy group or substituted aryloxy group have the same meanings with the groups described above, and embodiments of the present invention does not repeat them here.

In embodiments of the present invention, the flavone derivatives shown by the structure of formula (VII) include, but are not limited within the compounds listed in Table 4.

TABLE 4 the compounds of the flavone derivatives in particular preparing embodiments as provided by embodiments of the present invention.

| Serial | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| 454 | —OCH$_3$ | —H | —OCH$_3$ | —H | —H | —OCH$_3$ | —OCH$_3$ | —H | —H | —H |
| 455 | —NH$_2$ | —H | —F | —H | —H | —CN | —OH | —H | —H | —H |
| 456 | —C$_{20}$H$_{40}$Cl | —H | C$_6$H$_5$CC— | —H | —H | —NO$_2$ | —OH | —H | —H | —H |
| 457 | —CHCH$_2$ | —H | NH$_2$CO— | —H | —H | —C$_4$H$_7$S | —NH$_2$ | —H | —H | —H |
| 458 | —C$_3$H$_5$ | —H | —C$_6$H$_5$ | —H | —H | —C$_6$H$_{11}$ | CH$_3$CH$_2$— | —H | —H | —H |
| 459 | —OH | —H | —C$_5$H$_{10}$Cl | —H | —H | CH$_3$CH$_2$— | —C$_5$H$_{11}$ | —H | —H | —H |
| 460 | —CN | —H | C$_6$H$_5$CH$_2$— | —H | —H | —C$_3$H$_5$ | —NO$_2$ | —H | —H | —H |
| 461 | —F | —H | —COOH | —H | —H | —OH | —C$_{20}$H$_{41}$ | —H | —H | —H |
| 462 | —C$_6$H$_5$ | —H | CH$_3$CH$_2$— | —H | —H | —C$_3$H$_6$ | —C$_{20}$H$_{40}$Cl | —H | —H | —H |
| 463 | —COOH | —H | —C$_3$H$_5$ | —H | —H | —COOH | —CN | —H | —H | —H |
| 464 | —C$_3$H$_7$ | —H | —CH$_2$CH$_2$SO$_3$H | —H | —H | —I | —CONH$_2$ | —H | —H | —H |
| 465 | —C$_{20}$H$_{40}$Cl | —H | —OH | —H | —H | —SCN | —OH | —H | —H | —H |
| 466 | —OH | —H | —OH | —H | —H | —OH | —COOH | —H | —H | —H |
| 467 | —C$_3$H$_7$ | —H | —OH | —H | —H | —NO$_2$ | —C$_6$H$_5$ | —H | —H | —H |
| 468 | —NO$_2$ | —H | —SCN | —H | —H | —C$_4$H$_8$N | CH$_3$CH$_2$— | —H | —H | —H |
| 469 | —CH$_2$CH$_2$SO$_3$H | —H | —C$_4$H$_8$N | —H | —H | —NH$_2$ | —SCN | —H | —H | —H |
| 470 | —CCH | —H | —NO$_2$ | —H | —H | —CCH | —C$_4$H$_7$S | —H | —H | —H |
| 471 | —C$_{20}$H$_{40}$Cl | —H | —I | —H | —H | —CH$_2$CH$_2$SO$_3$H | —C$_3$H$_5$ | —H | —H | —H |
| 472 | —OCH$_3$ | —H | —C$_3$H$_5$ | —H | —H | C$_6$H$_5$CH$_2$— | —CH$_2$CH$_2$SO$_3$H | —H | —H | —H |
| 473 | —F | —H | —CN | —H | —H | —OCH$_3$ | —NH$_2$ | —H | —H | —H |
| 474 | C$_6$H$_5$CC— | —H | —NO$_2$ | —H | —H | —SCN | —C$_{20}$H$_{40}$Cl | —H | —H | —H |
| 475 | NH$_2$CO— | —H | —C$_4$H$_7$S | —H | —H | C$_6$H$_5$O— | —CHCH$_2$ | —H | —H | —H |
| 476 | —C$_6$H$_5$ | —H | —C$_6$H$_{11}$ | —H | —H | CH$_3$CH$_2$— | —C$_3$H$_5$ | —H | —H | —H |
| 477 | —C$_5$H$_{10}$Cl | —H | CH$_3$CH$_2$— | —H | —H | —C$_5$H$_{10}$Cl | —OH | —H | —H | —H |
| 478 | C$_6$H$_5$CH$_2$— | —H | —C$_3$H$_5$ | —H | —H | C$_6$H$_5$CH$_2$— | —CN | —H | —H | —H |
| 479 | —COOH | —H | —OH | —H | —H | —CHCH$_2$ | —F | —H | —H | —H |
| 480 | CH$_3$CH$_2$— | —H | —C$_3$H$_6$ | —H | —H | —CCH | —C$_6$H$_5$ | —H | —H | —H |
| 481 | —C$_3$H$_5$ | —H | —COOH | —H | —H | —C$_5$H$_{11}$ | —COOH | —H | —H | —H |
| 482 | —CH$_2$CH$_2$SO$_3$H | —H | —I | —H | —H | —F | —C$_3$H$_7$ | —H | —H | —H |
| 483 | —OH | —H | —SCN | —H | —H | —COOH | —C$_{20}$H$_{40}$Cl | —H | —H | —H |
| 484 | —OH | —H | —OH | —H | —H | —OH | —OH | —H | —H | —H |
| 485 | —OH | —H | —NO$_2$ | —H | —H | —OCH$_3$ | —C$_3$H$_7$ | —H | —H | —H |
| 486 | —SCN | —H | —C$_4$H$_8$N | —H | —H | —C$_4$H$_8$S | —NO$_2$ | —H | —H | —H |
| 487 | —C$_4$H$_8$N | —H | —NH$_2$ | —H | —H | C$_6$H$_5$CO— | —CH$_2$CH$_2$SO$_3$H | —H | —H | —H |
| 488 | —NO$_2$ | —H | —CCH | —H | —H | —OCH$_3$ | —CCH | —H | —H | —H |
| 489 | —I | —H | —CH$_2$CH$_2$SO$_3$H | —H | —H | —CH$_2$CH$_2$SO$_3$H | —C$_{20}$H$_{40}$Cl | —H | —H | —H |
| 490 | —C$_3$H$_5$ | —H | C$_6$H$_5$CH$_2$— | —H | —H | C$_{10}$H$_{21}$CH$_2$O— | —OCH$_3$ | —H | —H | —H |
| 491 | —NO$_2$ | —H | —H | —H | —H | —CH$_3$ | C$_6$H$_5$O— | —H | —H | —H |
| 492 | —C$_4$H$_7$S | —H | —H | —H | —H | C$_6$H$_5$CC— | CH$_3$CH$_2$— | —H | —H | —H |
| 493 | —C$_6$H$_{11}$ | —H | —H | —H | —H | NH$_2$CO— | —C$_5$H$_{10}$Cl | —H | —H | —H |
| 494 | CH$_3$CH$_2$— | —H | —H | —H | —H | —C$_6$H$_5$ | C$_6$H$_5$CH$_2$— | —H | —H | —H |
| 495 | —C$_3$H$_5$ | —H | —H | —H | —H | —C$_5$H$_{10}$Cl | —CHCH$_2$ | —H | —H | —H |
| 496 | —OH | —H | —H | —H | —H | C$_6$H$_5$CH$_2$— | —CCH | —H | —H | —H |
| 497 | —C$_3$H$_6$ | —H | —H | —H | —H | —COOH | —C$_5$H$_{11}$ | —H | —H | —H |
| 498 | —COOH | —H | —H | —H | —H | CH$_3$CH$_2$— | —F | —H | —H | —H |
| 499 | —I | —H | —H | —H | —H | —C$_3$H$_5$ | —COOH | —H | —H | —H |
| 500 | —SCN | —H | —H | —H | —H | —CH$_2$CH$_2$SO$_3$H | —OH | —H | —H | —H |
| 501 | —OH | —H | —H | —H | —H | —OH | —OCH$_3$ | —H | —H | —H |
| 502 | —NO$_2$ | —H | —H | —H | —H | —OH | —C$_4$H$_7$S | —H | —H | —H |
| 503 | —C$_4$H$_8$N | —H | —H | —H | —H | —OH | —SCN | —H | —H | —H |

In Table 4, —C$_{20}$H$_{41}$ is a linear eicosyl group; the structural formula of —C$_3$H$_5$ is —CH═CHCH$_3$; the structural formula of —C$_4$H$_7$S is

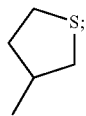

—C$_5$H$_{11}$ is n-pentyl; the structural formula of —C$_4$H$_8$N is

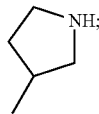

—C$_{20}$H$_{40}$Cl is a chloro-linear eicosyl group; —C$_6$H$_{11}$ is n-octenyl group.

In embodiments of the present invention, when R$_2$, R$_4$, R$_5$, R$_8$, R$_9$ and R$_{10}$ are —H respectively in the compound shown by the structure of Formula (I), said compound represents the structure of Formula (VII). In Table 4, flavone derivatives with particular structures are obtained when combining R$_1$, R$_3$, R$_6$ and R$_7$ groups with the skeletal structure shown by the structure of Formula (VII). Embodiments of the present invention does not make particular restrictions on the above.

The inventors of embodiments of the present invention surprisingly discover that, when the R$_1$-R$_{10}$ groups in the flavone derivatives of Formula (I) or the flavanone derivatives of Formula (II) comprise two or more alkoxy groups, preferably three or more alkoxy groups, more preferably five or more alkoxy groups, said flavone derivatives or flavanone derivatives have excellent sedative and hypnotic bioactivities, wherein, said alkoxy groups are more preferably methoxy groups or ethoxy groups, and most preferably, methoxy groups. Said compounds are, further more preferably, the following compounds:

Compound 504: 5,7,3',4',5'-penta methoxyl-flavone;
Compound 505: 6,7,8,3',4'-penta methoxyl-flavanone;
Compound 506: 5-hydroxyl-6,7,8,3',4'-penta methoxyl-flavone;
Compound 507: 5,7,3',4'-tetra methoxyl-flavone;
Compound 508: 5,7,3',4',5'-penta methoxyl-flavanone;
Compound 510: 3,5,7,8,3',4',5',6'-octa methoxyl-flavone;
Compound 511: 3,5,6,7,8,3',4',5'-octa methoxyl-flavone;
Compound 512: 3,5,6,7,8,3',4'-hepta methoxyl-flavone;
Compound 513: 3,5,6,7,3',4',5'-hepta methoxyl-flavone;
Compound 514: 3,5,7,8,3',4',5'-hepta methoxyl-flavone;
Compound 515: 5,6,7,8,3',4'-hexa methoxyl-flavone;
Compound 516: 1,5,6,7,3',4'-hexa methoxyl-flavone;
Compound 517: 1,5,7,8,3',4'-hexa methoxyl-flavone;
Compound 518: 3,5,6,7,3',4'-hexa methoxyl-flavone;
Compound 519: 5,7,8,3',4',5'-hexa methoxyl-flavone;
Compound 520: 6,7,8,3',4',5'-hexa methoxyl-flavone;
Compound 521: 5-hydroxyl-3,6,7,8,3',4'-hexa methoxyl-flavone;
Compound 522: 3-hydroxyl-5,6,7,8,3',4'-hexa methoxyl-flavone;
Compound 523: 7-hydroxyl-3,5,6,8,3',4'-hexa methoxyl-flavone;
Compound 524: 4'-hydroxyl-3,5,6,7,3',5'-hexa methoxyl-flavone;
Compound 525: 5-hydroxyl-6,7,8,3',4',5'-hexa methoxyl-flavone;
Compound 526: 2'-hydroxyl-3,4,3',4',5',6'-hexa methoxyl-flavone;
Compound 527: 5,6,7,3',4'-penta methoxyl-flavone;
Compound 528: 5,7,8,3',4'-penta methoxyl-flavone;
Compound 529: 5,6,7,8,4'-penta methoxyl-flavone;
Compound 530: 6,7,8,3',4'-penta methoxyl-flavone;
Compound 531: 7-hydroxyl-3,5,6,3',4'-penta methoxyl-flavone;
Compound 532: 5-hydroxyl-3,7,8,3',4'-penta methoxyl-flavone;
Compound 533: 5-hydroxyl-6,7,3',4',5'-penta methoxyl-flavone;
Compound 534: 3-hydroxyl-5,7,3',4',5'-penta methoxyl-flavone;
Compound 535: 2'-hydroxyl-4',5',6',3,4-penta methoxyl-flavone;
Compound 536: 5,3'-dihydroxyl-6,7,8,4',5'-penta methoxyl-flavone;
Compound 537: 5,6,7,4'-tetra methoxyl-flavone;
Compound 538: 5,7,8,4'-tetra methoxyl-flavone;
Compound 539: 5-hydroxyl-3,7,3',4'-tetra methoxyl-flavone;
Compound 540: 5-hydroxyl-6,7,8,4'-tetra methoxyl-flavone;
Compound 541: 3-hydroxyl-5,6,7,4'-tetra methoxyl-flavone;
Compound 542: 3-hydroxyl-5,7,8,4'-tetra methoxyl-flavone;
Compound 543: 5,3',5'-trihydroxyl-6,7,8,4'-tetra methoxyl-flavone;
Compound 544: 5,3'-dihydroxyl-6,7,4',5'-tetra methoxyl-flavone;
Compound 545: 5,7,4'-trimethoxyl-flavone,
Compound 546: 5-hydroxyl-6,7,4'-trimethoxyl-flavone;
Compound 547: 7-hydroxyl-5,3',4'-trimethoxyl-flavone;
Compound 548: 3'-hydroxyl-5,7,4'-trimethoxyl-flavone;
Compound 549: 5,7,4'-trihydroxyl-6,8,3'-trimethoxyl-flavone;
Compound 550: 5,3',5'-trihydroxyl-6,7,4'-trimethoxyl-flavone;
Compound 551: 5,7,8,3',4'-penta methoxyl-flavanone;
Compound 552: 5-hydroxyl-6,7,8,3',4'-penta methoxyl-flavanone;
Compound 553: 5,6,7,4'-tetra methoxyl-flavanone;
Compound 554: 5,7,2',3',4',5'-hexa methoxyl-flavanone;
Compound 555: 5,7,3',4',5',6'-hexa methoxyl-flavone;
Compound 556: 3,5,7,3',4',5',6'-hepta methoxyl-flavone;
Compound 557: 3-hydroxyl-5,7,2',3',4',5',6'-hepta methoxyl-flavone;
Compound 558: 4'-hydroxyl-5,7,3',5'-tetra methoxyl-flavone;
Compound 559: 5'-hydroxyl-5,7,3',4'-tetra methoxyl-flavone;
Compound 560: 5-hydroxyl-7,3',4',5'-tetra methoxyl-flavone;
Compound 561: 7-hydroxyl-5,3',4',5'-tetra methoxyl-flavone;
Compound 562: 7-ethoxyl-5,3',4',5'-tetra methoxyl-flavone;
Compound 563: 6,7,8,3',4',5'-hexa methoxyl-flavanone;
Compound 564: 6,7,8,3',4',5',6'-hepta methoxyl-flavanone;
Compound 565: 3,6,7,8,3',4',5',6'-octa methoxyl-flavanone;
Compound 566: 3,6,7,8,3',5',6'-hepta methoxyl-flavanone;
Compound 567: 3,6,7,8,4',5',6'-hepta methoxyl-flavanone;
Compound 568: 3,6,7,8,3',4',6'-hepta methoxyl-flavanone;
Compound 569: 3,6,7,8,3',4',5'-hepta methoxyl-flavanone;
Compound 570: 5-hydroxyl-3,6,7,8,3',4',5',6'-octa methoxyl-flavanone;

Compound 571: 6-hydroxyl-3,7,8,3',4',5',6'-hepta methoxyl-flavanone;
Compound 572: 7-hydroxyl-3,6,8,3',4',5',6'-hepta methoxyl-flavanone;
Compound 573: 8-hydroxyl-3,6,7,3',4',5',6'-hepta methoxyl-flavanone;
Compound 574: 3'-hydroxyl-3,6,7,8,4',5',6'-hepta methoxyl-flavanone;
Compound 575: 4'-hydroxyl-3,6,7,8,3',5',6'-hepta methoxyl-flavanone;
Compound 576: 5'-hydroxyl-3,6,7,8,3',4',6'-hepta methoxyl-flavanone;
Compound 577: 6'-hydroxyl-3,6,7,8,3',4',5'-hepta methoxyl-flavanone;
Compound 578: 3-hydroxyl-6,7,8,3',4',5',6'-hepta methoxyl-flavanone;
Compound 579: 5,6,4',5',6'-penta methoxyl-flavone;
Compound 580: 5,6,4',5'-tetra methoxyl-flavone;
Compound 581: 6-amino-7,4',5'-trimethoxyl-flavone,
Compound 582: 6-cyano-7-ethoxyl-2'-ethylnenoxy-3,6'-dimethoxyl flavone;
Compound 583: 6-benzyl-5,2',5'-trihydroxyl flavone;
Compound 584: 6-nitro-7-hydroxyl-3'-benzyl-6'-cyano flavone;
Compound 585: 3'-hydroxyl-5,7,4',5'-tetramethoxyl-flavone,
Compound 586: 5,5'-dihydroxyl-7,8,2'-trimethoxyl-flavone;
Compound 587: 5,3'-dihydroxyl-7,8,4'-trimethoxyl-flavone;
Compound 588: 2'-hydroxyl-5,7,8-trimethoxyl-flavone,
Compound 589: 6,7,8,4'-tetramethoxyl-flavone,
Compound 590: 5,6,7,8,4'-penta methoxyl-flavone;
Compound 591: 5-hydroxyl-7,8,2',3',4'-penta methoxyl-flavone;
Compound 592: 5,6,7,3',4',5'-hexamethoxyl-flavone,
Compound 593: 5,6,7,8,3',4',5'-heptamethoxyl-flavone,
Compound 594: 5-hydroxyl-6,7,8,4'-tetramethoxyl-flavanone;
Compound 595: 5-hydroxyl-6,7,8,3',4'-penta methoxyl-flavanone;
Compound 596: 5,6,7,8,4'-penta methoxyl-flavanone;
Compound 597: 5,6,7,8,3',4'-hexamethoxyl-flavanone.

Embodiments of the present invention does not particularly restrict the origins of the flavone derivatives shown by the structure of Formula (I) or the flavanone derivatives shown by the structure of Formula (II). Said flavone derivatives or flavanone derivatives may be purchased commercially, like Compound 504~Compound 553 listed above, which are all flavone derivatives or flavanone derivatives that has been disclosed in the prior arts, and may also be purchased commercially. The flavone derivatives shown by the structure of Formula (I) or the flavanone derivatives shown by the structure of Formula (II) may also be prepared according to methods well known to people skilled in the art, and said methods are such as:

Preparation Method 1:

The preparation method for flavone derivatives disclosed in Chinese Patent literature 200610116105.9 is used to prepare substituted flavone derivatives.

Furthermore, said substituted flavone derivatives are further substituted according to the methods in U.S. Pat. No. 5,861,462 or methods well known to those skilled in the art, to give flavone derivatives with target structures.

Carrying out hydrogenation reactions on the flavone derivatives having the structure of Formula (I), one obtains the flavanone derivatives having the structure of Formula (II).

Regarding the above, those skilled in the art may refer to the patent literatures listed above, and embodiments of the present invention does not further discuss in detail. Furthermore, those skilled in the art would appreciate that, when the flavone derivatives with target structures can be prepared according to the Chinese Patent literature, they do not need to further employ the methods in U.S. Pat. No. 5,861,462 or other methods to further substitute the flavone derivatives.

Preparation Method 2:

The preparation method for flavone derivatives disclosed in Chinese Patent literature 200710156906.2 is used to prepare substituted flavone derivatives.

Furthermore, said substituted flavone derivatives are further substituted according to the methods in U.S. Pat. No. 5,861,462 or methods well known to those skilled in the art, to give flavone derivatives with target structures.

Carrying out hydrogenation reactions on the flavone derivatives having the structure of Formula (I), one obtains the target flavanone derivatives having the structure of Formula (II).

Regarding the above, those skilled in the art may refer to the patent literatures listed above, and embodiments of the present invention does not further discuss in detail. Furthermore, those skilled in the art would appreciate that, when the flavone derivatives with target structures can be prepared according to the Chinese Patent literature, they do not need to further employ the methods in U.S. Pat. No. 5,861,462 or other methods to further substitute the flavone derivatives.

Preparation Method 3:

The preparation method for flavone derivatives disclosed in Chinese Patent literature 200810060946.1 is used to prepare substituted flavone derivatives.

Furthermore, said substituted flavone derivatives are further substituted according to the methods in U.S. Pat. No. 5,861,462 or methods well known to those skilled in the art, to give flavone derivatives with target structures.

Carrying out hydrogenation reactions on the flavone derivatives having the structure of Formula (I), one obtains the target flavanone derivatives having the structure of Formula (II).

Regarding the above, those skilled in the art may refer to the patent literatures listed above, and embodiments of the present invention does not further discuss in detail. Furthermore, those skilled in the art would appreciate that, when the flavone derivatives with target structures can be prepared according to the Chinese Patent literature, they do not need to further employ the methods in U.S. Pat. No. 5,861,462 or other methods to further substitute the flavone derivatives.

Preparation Method 4:

The preparation method for flavone derivatives disclosed in Chinese Patent literature 200910024940.3 is used to prepare substituted flavone derivatives.

Furthermore, said substituted flavone derivatives are further substituted according to the methods in U.S. Pat. No. 5,861,462 or methods well known to those skilled in the art, to give flavone derivatives with target structures.

Carrying out hydrogenation reactions on the flavone derivatives having the structure of Formula (I), one obtains the target flavanone derivatives having the structure of Formula (II).

Regarding the above, those skilled in the art may refer to the patent literatures listed above, and embodiments of the present invention does not further discuss in detail. Furthermore, those skilled in the art would appreciate that, when the flavone derivatives with target structures can be prepared according to the Chinese Patent literature, they do not need to further employ the methods in U.S. Pat. No. 5,861,462 or other methods to further substitute the flavone derivatives.

Preparation Method 5:

Step 11): reacting p-substituted phenol with acetic anhydride in pyridine to give first intermediate;

Step 12): said first intermediate undergoes rearrangement reactions under the action of aluminum chloride to give second intermediate;

Step 13): said second intermediate reacts with benzoyl chloride or substituted benzoyl chloride in pyridine to give third intermediate;

Step 14): said third intermediate undergoes reactions under the action of potassium hydroxide in pyridine to give fourth intermediate;

Step 15): said fourth intermediate undergoes reactions under the action of concentrated sulfonic acid to give a flavone derivative having a structure of Formula (I-a);

Step 16): After obtaining the flavone derivative having a structure of Formula (I-a), said substituted flavone derivative is further substituted to obtain the flavone derivative having the target structure, by the method in U.S. Pat. No. 5,861,462 or by methods well known to those skilled in the art;

Step 17): Carrying out hydrogenation reaction on the flavone derivative having a structure of Formula (I) to give a flavanone derivative having a structure of Formula (II).

The reaction process of preparation method 5 is as follows:

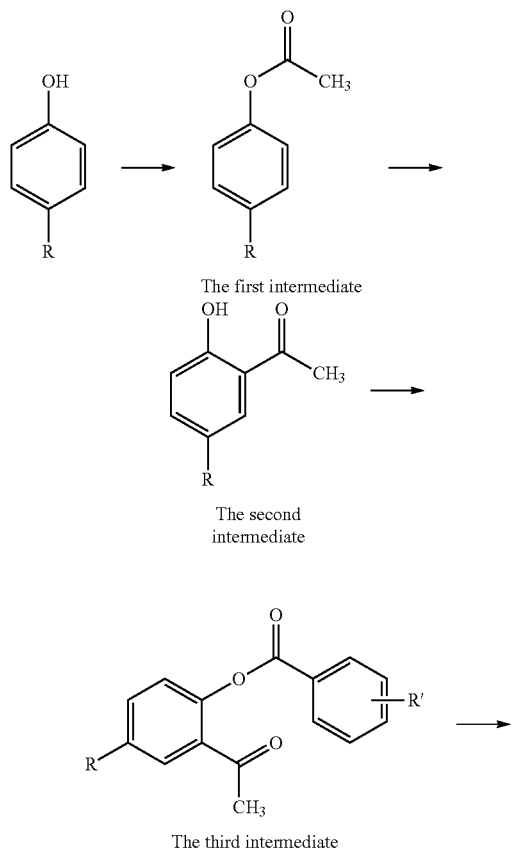

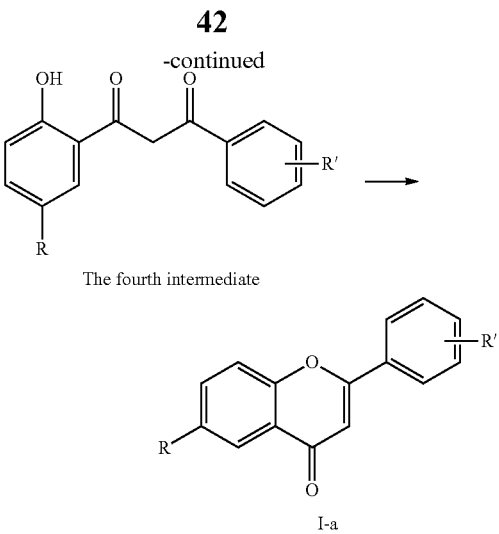

Particularly, when the p-substituted phenol is p-methyl phenol, and the substituted benzoyl chloride is o-nitro benzoyl chloride, m-nitro benzoyl chloride and p-nitro benzoyl chloride, respectively, one may obtain 6-methyl-2'-nitro flavone, 6-methyl-3'-nitro flavone or 6-methyl-4'-nitro flavone; or when p-substituted phenol is p-methyl phenol, and the substituted benzoyl chloride is o-methoxyl benzoyl chloride, m-methoxyl benzoyl chloride and p-methoxyl benzoyl chloride, respectively, one may obtain 6,2'-dimethoxyl flavone, 6,3'-dimethoxyl flavone or 6,4'-dimethoxyl flavone; or when p-substituted phenol is p-methyl phenol, and the substituted benzoyl chloride is trimethoxyl-benzoyl chloride, one may obtain 6,1',2',3'-tetramethoxyl-flavone. Regarding the above, those skilled in the art may choose particular raw materials on the basis of the structure of target products, and embodiments of the present invention does not make particular restrictions.

Preparation 6:

Flavanone derivatives having a structure of Formula (II) is prepared according to the method recorded in Shi Lei, Ban Shurong, Feng Xiu'e et. al, Researches on synthesis of flavanone derivatives and anti-tumor activities of the same, Chin J Med Chem, volume 20, issue 2, June 2010 (Summed up, Issue 95), pp 176-180, Chinese Journal of Medicinal Chemistry.

Furthermore, said substituted flavanone derivatives are further substituted according to the methods in U.S. Pat. No. 5,861,462 or methods well known to those skilled in the art, to give flavanone derivatives with target structures.

Regarding the above, those skilled in the art may refer to the patent literatures listed above, and embodiments of the present invention does not further discuss in detail. Furthermore, those skilled in the art would appreciate that, when the flavanone derivatives with target structures can be prepared according to the Chinese Patent literature, they do not need to further employ the methods in U.S. Pat. No. 5,861,462 or other methods to further substitute the flavanone derivatives.

Preparation Method 7:

Substituted flavanone derivatives may be prepared according to the method disclosed in Chinese Patent literature 200910074951.2.

Furthermore, said substituted flavanone derivatives are further substituted according to the methods in U.S. Pat. No. 5,861,462 or methods well known to those skilled in the art, to give flavanone derivatives with target structures.

Regarding the above, those skilled in the art may refer to the patent literatures listed above, and embodiments of the present invention does not further discuss in detail. Furthermore, those skilled in the art would appreciate that, when the flavanone derivatives with target structures can be prepared according to the Chinese Patent literature, they do not need to further employ the methods in U.S. Pat. No. 5,861,462 or other methods to further substitute the flavanone derivatives.

In another aspect of embodiments of the present invention, a pharmaceutical composition is provided, which comprises a compound represented by general formula (I-VII) or a pharmaceutically accepted salt thereof as an active ingredient, which is mixed with one or more conventional carriers or additives. The pharmaceutical composition according to embodiments of the present invention generally comprises 0.2-96 wt. %, preferably 1-50 wt. %, particularly 5-20 wt. % active ingredient.

The pharmaceutical composition of embodiments of the present invention may be adopted for oral administration (such as powder, tablets, coated tablets, capsules, microcapsules, pills, solutions, suspensions, or emulsions), parenteral administration (such as injection solutions for use in intravenous, intramuscular, subcutaneous and intraperitoneal purpose), rectal administration (such as suppository), transdermal (such as plaster) or local administration (such as cream or plaster), or it may be used in the form of implants. The solid, soft or liquid drugs according to embodiments of the present invention may be produced with the help of methods commonly used in pharmaceutical industry.

Solid pharmaceutical compositions for use in oral administration containing compounds represented by any of Formula (I-VII) or pharmaceutically accepted salts thereof may comprise fillers or carriers (such as lactose, glucose, starch, potassium phosphate, microcrystalline cellulose), binders (such as gelatin, sorbitol, polyvinylpyrrolidone), disintegrant (such as croscarmelose, sodium carboxymethyl cellulose, povidone), pelleting agent (such as magnesium stearate, talc, polyethylene glycol, silicate, silica) and surfactant (such as sodium lauryl sulfate).

The liquid composition suitable for oral administration may be a solution, suspension or emulsion. This type of composition may comprise suspending agents (such as gelatin, carboxymethyl cellulose), emulsifier (such as dehydrated sorbitan oleate), solvent (such as water, oil, glycerin, propylene glycol, ethanol), buffer (such as acetates, phosphates, citrate buffer) and preservatives (such as methyl-4-hydroxyl benzoic acid ester).

Liquid pharmaceutical composition suitable for parenteral administration is generally a sterile isotonic solution, and it may optionally comprise buffers and preservatives besides the solvents.

Soft pharmaceutical compositions (such as suppositories) containing compounds represented by any of Formula (I-VII) or pharmaceutically accepted salts thereof as active ingredients may comprise active ingredients evenly dispersed in the suppositories substrate (like PEG or cocoa butter).

The pharmaceutical compositions according to embodiments of the present invention may be prepared by known methods in the pharmacy industry. The active ingredients are mixed with a pharmaceutically accepted solid or liquid carrier and/or an adjuvant, and then the mixture is prepared as Galenical dose formulations. The carriers, adjuvants and methods suitable in the pharmacy industry are disclosed in literatures (Remington's Pharmaceutical Sciences, Edition 18, Mack Publishing Co., Easton, USA, 1990).

The pharmaceutical compositions according to embodiments of the present invention generally comprise unit dosages. The daily dosage for an adult is generally 0.1-1000 mg/kg wt. compounds represented by general formulas (I-VII) or pharmaceutically accepted salts thereof. Said daily dosage may be administered in one or more doses. The actual daily dosage depends on several factors and is determined by the physician.

According to another aspect of embodiments of the present invention, uses of the compounds represented by general formulas (I-VII) or pharmaceutically accepted salts thereof are provided. The compounds represented by general formulas (I-VII) or pharmaceutically accepted salts thereof have significant sedative and hypnotic effects, and may be used to prepare sedative and hypnotic drugs.

Embodiments of the present invention are conducted on the basis of the following surprising knowledge: the compounds represented by general formulas (I-VII) or pharmaceutically accepted salts thereof show significant sedative and hypnotic effects. This particular effect has not been recorded in any existing art, particularly, in any literatures on flavone compounds and derivatives thereof.

TERMINOLOGY

As described in embodiments of the present invention, the compounds in embodiments of the present invention may be optionally substituted by one or more substituting groups, like the compounds represented by the general formulas, the examples and sub-types in the embodiments, and the compounds included in embodiments of the present invention. It should be appreciated that, the term "optionally substituted" may be used interchangeably with the term "substituted or unsubstituted". Generally speaking, whether the term "optionally" is placed before or after the term "substituted", the term means that one or more hydrogen atoms in the given structure may be substituted by particular substituting groups. Unless otherwise indicated, an optional substituting group may have one substituting in the available sites of the group. If the given structural formula comprises more than one site which may be substituted by one or more said substituting groups, said substituting group may exist in each of the sites in a same or different way. Said substituting group may be, without limiting, hydroxyl group, amino group, halogen, cyano group, aromatic group, miscellaneous aryl group, alkoxy group, alkyl group, alkenyl group, alkynyl group, heterocyclic group, thio group, nitro group, aryloxy group and the like.

The term "alkyl" or "alkyl group" used in embodiments of the present invention stands for a saturated linear or branched monovalence carbon-hydrogen atomic group, which comprises 1-20 carbon atoms, wherein said alkyl group may be optionally substituted by one or more substituting groups. The alkyl group comprises 1-20 carbon atoms unless otherwise indicated.

Examples of alkyl groups include, but are not limited to methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), iso-butyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl(—$CH(CH_2CH_3)_2$), 2-methyl-2-butyl(—$C(CH_3)_2CH_2CH_3$), 3-methyl-2-butyl(—$CH(CH_3)CH(CH_3)_2$), 3-methyl-1-butyl (—$CH_2CH_2CH(CH_3)_2$), 2-methyl-1-butyl(—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ (CH₂CH₂CH₃)), 2-methyl-2-pentyl(—C(CH₃)₂CH₂CH₂CH₃), 3-methyl-2-pentyl(—CH(CH₃)CH(CH₃)CH₂CH₃), 4-methyl-2-pentyl(CH(CH₃)CH₂CH(CH₃)₂), 3-methyl-3-pentyl(—C(CH₃)(CH₂CH₃)₂), 2-methyl-3-pentyl(—CH(CH₂CH₃)CH(CH₃)₂), 2,3-dimethyl-2-butyl(—C(CH₃)₂CH(CH₃)₂), 3,3-dimethyl-2-butyl(—CH(CH₃)C(CH₃)₃), n-heptyl, n-octyl and the like.

As used in embodiments of the present invention, terms "alkyl" and the prefix "alk" both include linear and branched saturated carbon chains.

Term "alkoxy group" means that an alkyl group is connected with the other part of the molecule via an oxygen atom, wherein said alkyl group has the meaning described in embodiments of the present invention. Unless otherwise indicated particularly, the alkoxy group comprises 1-20 carbon atoms, in some examples said alkoxy group comprises 1-10 carbon atoms, in some other examples said alkoxy group comprises 1-8 carbon atoms, in some other examples said alkoxy group comprises 1-6 carbon atoms, in other some examples said alkoxy group comprises 1-4 carbon atoms, and in some other examples said alkoxy group comprises 1-3 carbon atoms.

Examples of alkoxy groups include, but are not limited to, methoxy group (MeO, —OCH₃), ethoxyl group (EtO, —OCH₂CH₃), 1-propoxy group (n-PrO, n-propoxy group, —OCH₂CH₂CH₃), 2-propoxy group (i-PrO, i-propoxy group, —OCH(CH₃)₂), 1-butoxy group (n-BuO, n-butoxy group, —OCH₂CH₂CH₂CH₃), 2-methyl-1-propoxy group (i-BuO, i-butoxy group, —OCH₂CH(CH₃)₂), 2-butoxy group (s-BuO, s-butoxy group, —OCH(CH₃)CH₂CH₃), 2-methyl-2-propoxy group (t-BuO, t-butoxy group, —OC(CH₃)₃), 1-pentoxy group (n-pentoxy group, —OCH₂CH₂CH₂CH₂CH₃), 2-pentoxy group (—OCH(CH₃)CH₂CH₂CH₃), 3-pentoxy group (—OCH(CH₂CH₃)₂), 2-methyl-2-butoxy group (—OC(CH₃)₂CH₂CH₃), 3-methyl-2-butoxy group (—OCH(CH₃)CH(CH₃)₂), 3-methyl-1-butoxy group (—OCH₂CH₂CH(CH₃)₂), 2-methyl-1-butoxy group (—OCH₂CH(CH₃)CH₂CH₃), and the like.

Term "hydroxyl alkoxy" means that a linear or branched alkoxy group is substituted by one or more hydroxyl group, wherein said alkoxy group has the meaning described in embodiments of the present invention. Unless otherwise indicated particularly, the hydroxyl alkoxy group comprises 1-20 carbon atoms, in some examples said hydroxyl alkoxy group comprises 1-10 carbon atoms, in some other examples said hydroxyl alkoxy group comprises 1-8 carbon atoms, in some other examples said hydroxyl alkoxy group comprises 1-6 carbon atoms, in other some examples said hydroxyl alkoxy group comprises 1-4 carbon atoms, and in some other examples said hydroxyl alkoxy group comprises 1-3 carbon atoms. In some embodiments, hydroxyl alkoxy group comprises 4 hydroxyl groups. In other embodiments, hydroxyl alkoxy group comprises 3 hydroxyl groups. In other embodiments, hydroxyl alkoxy group comprises 2 hydroxyl groups. In other embodiments, hydroxyl alkoxy comprises 1 hydroxyl group.

Examples of hydroxyl alkoxy include, but are not limited to, hydroxyl ethoxyl group (—OCH₂CH₂OH), 2-hydroxyl propoxy group (—OCH₂CH₂(OH)CH₃), 3-hydroxyl propoxy group (—OCH₂CH₂CH₂OH), 2-hydroxyl-2-methyl propoxy group (—OCH₂C(OH)(CH₃)₂), (R)-2-hydroxyl propoxy group (—(R)—OCH₂CH(OH)CH₃), or (S)-2-hydroxyl propoxy group (—(S)—OCH₂CH(OH)CH₃), —OCH₂CH(OH)CH₂OH, —OCH(CH₃)(CH₂OH), —OCH₂CH(OH)CH₂CH₃, —OCH₂CH₂CH(OH)CH₃, —OCH₂CH₂CH₂CH₂OH, —OCH₂C(OH)(CH₃)₂, —OCH₂CH(CH₂OH)₂, —OCH₂CH(CH₃)(CH₂OH), —OCH₂C(OH)(CH₃)(CH₂OH), —OCH(CH₃)CH(OH)CH₃, —OCH(CH₂OH)CH₂CH₃, —OC(CH₃)₂(CH₂OH), —OC(CH₃)(CH₂OH)₂, and the like.

Terms "halogenated alkyl group" or "halogenated alkoxy group" means that a alkyl group or alkoxy group is substituted by one or more halogen atoms. Examples of terms "halogenated alkyl group" or "halogenated alkoxy group" include, but are not limited to trifluoromethyl group, trifluoromethoxy group and the like.

Term "halogen" stands for F, Cl, Br or I.

Term "H" stands for a single hydrogen atom. Such atom group may be connected with other groups, i.e., an oxygen atom, to form a hydroxyl group.

Term "aryl group" may be used alone or it may be a major part of "alkyl aryl group", "alkoxy aryl group" or "alkyl aryloxy group", which means a carbon ring system consisting of one, two or three rings and comprising 6-14 ring members. Among the above, at least one ring system is aromatic, and each of the ring systems comprise a ring of 3-7 ring members and said ring system only has one attaching point to connect with other parts of the remaining part of the molecule. The term "aryl group" may be used interchangeably with term "aromatic ring", for example, said aromatic ring may include phenyl group, naphthyl group and anthracene. Meanwhile, said aryl group may be substituted or unsubstituted, and wherein the substituting groups may be, but are not limited within hydroxy group, amino group, halogen, cyano group, aryl group, heteroaryl group, alkoxy group, alkyl group, alkenyl group, alknyl group, heterocyclic alkyl group, thio group, nitro group, aryoxy group, and the like.

Term "carboxylic group", like "carboxyl alkyl group", when used alone or in combination with other terms, is intended to stand for —CO₂H; term "carbonyl group", like "amino carbonyl group" or "acyloxy group", when used alone or in combination with other terms, is intended to stand for —(C═O)—.

The term "unsaturated" used in embodiments of the present invention are intended to mean that the degree of unsaturation of the described part is one or more.

The term "comprising" is intended to describe open ended concepts. In other words, the context illustrated in embodiments of the present invention are intended to be incorporated, and the context in other aspects is not excluded.

Unless otherwise indicated, the structural formulas described in embodiments of the present invention include all isomeric forms (such as enantiomers, diastereomers and geometrical isomers (or conformational isomers)), such as: R/S configurations containing asymmetric centers, (Z)/(E) isomers containing double bonds, and (Z)/(E) conformation isomers. Therefore, mixtures of a single stereochemistry isomer or the enantiomer thereof, diastereomers or geometrical isomers (or conformational isomers) of the compounds of embodiments of the present invention belongs to the scope of embodiments of the present invention.

As used in embodiments of the present invention, terms "tautomer" or "tautomer form" means that isomers with different structures on different energy levels may go over a low energy barrier to convert to each other. For example, in proton tautomer isomers (i.e., prototropic change), the conversion occurs via proton transfer, and such conversions include keto-enol tautomerizing and imine-enamine atutomerism. In valence tautomers, conversion occurs via restructuring of some of the bonding electrons.

Unless indicated otherwise, all the tautomer isomer forms of the compounds of embodiments of the present invention belong to the scope of embodiments of the present invention. Furthermore, unless indicated otherwise, the structural formula of the compound described in embodiments of the present invention has one atom or more than one different atoms replaced with enriched isotope atoms.

As used in embodiments of the present invention, the term "pro-drug" is intended to stand for a compound which is converted to another compound as represented by Formula (I) or Formula (II). Said conversion is affected by the process in a hydrolysis reaction in blood or a reaction in blood or tissue, in which the pro-drug is converted to a parent structure via enzymatic process.

The term "metabolite" is intended to stand for products that are produced in the in vivo metabolic process of particular compounds or salts thereof. The metabolite of a compound may be determined by technologies well known in the related art, and the activity of the metabolite may be characterized by the experimental methods described in embodiments of the present invention. Such products may be produced by treating the administered compound by methods selected from oxidation, reduction, hydrolysis, amidization, diamidization, esterification, defatting, enzymatic lysis and the like. Accordingly, embodiment of the present invention includes metabolites of compounds, including metabolites generated from the compound of embodiment of this invention contacting with a mammal for a sufficient time.

The compounds of embodiment of the invention may contain asymmetric or chiral centers, and therefore there are different stereoisomers. All stereoisomeric forms of the compounds of embodiment of the invention include but is not limited to diastereomers, enantiomers, atropisomers, and mixtures thereof, as racemic mixtures, which constitute part of embodiment of the invention. Many organic compounds exist in optically active forms, i.e., they have the ability to rotate the plane of plane-polarized light. In describing an optically active compound, the prefix D, L or R, S is used to denote the absolute configuration of the molecule chiral center. Prefixes d, l or (+), (−) is used to name the sign of rotation of plane polarized light of compound, (−) or l refers to that the compound is levorotatory, prefixes (+) or d refers to that the compound is dextrorotatory. The chemical structure of these stereoisomers are identical, but their three-dimensional structure is different. Specific stereoisomer may be enantiomers, mixture of isomers is often called an enantiomeric mixture. 50:50 mixture of enantiomers is called a racemic mixture or a racemate, which may lead to a chemical reaction process without stereoselectivity or stereospecificity. The term "racemic mixture" and "racemate" refer to a mixture of two enantiomers of equal moles, which lack of optically active.

Term "tautomeric form" or "tautomer" refers to isomers of different energies can be interconverted by a low energy barrier. For example, proton tautomers (i.e., a proton shifted tautomers) include interconversion by proton migration, such as keto-enol and imine-enamine isomerization effect. Valency (valence) tautomers include recomposition or interconversions of the bonding electrons.

Term "pharmaceutically acceptable salts" used in the present invention refers to organic and inorganic salts of the compounds of embodiments of the present invention. A pharmaceutically acceptable salt is known in the art.

Salts formed from pharmaceutically acceptable non-toxic acids include, but are not limited to, the inorganic and hydrochloride salts formed from reaction with the amino group, hydrobromide, phosphate, sulfate, perchlorate, and organic acid salts such as acetate, oxalate, maleate, tartrate, citrate, succinate, malonate, or obtained by other methods described in the literature and books such as ion exchange method. Other pharmaceutically acceptable salts include adipate, alginate, ascorbate, aspartate, benzenesulfonate, benzoate, bisulfate, borate, butyrate, camphorsulfonic acid salt, camphorsulfonate, cyclic pentyl propionate, 2-gluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts obtained by a suitable alkali include the alkali metal, alkaline earth metal, ammonium and N+($C_{1-4}$ alkyl)$_4$ salts. Embodiments of the present invention is also intended contemplates any quaternary ammonium formed from compound which contains N groups. Water-soluble or oil-soluble or dispersible products may be obtained by quaternization. Alkali metal or alkaline earth metal salts include sodium, lithium, potassium, calcium, magnesium, and the like. Pharmaceutically acceptable salts further include appropriate, nontoxic ammonium, quaternary ammonium salts and amine cations formed from anti-counter ion, such as halide, hydroxide, carboxylate, sulfated, phosphorylated compounds, nitrate compounds, $C_{1-8}$ sulfonic acid compounds and aromatic sulfonic acid compounds.

Unless otherwise indicated, all stereoisomers, geometric isomers, tautomers, nitrogen oxides, hydrates, solvates, metabolites, salts and pharmaceutically acceptable prodrugs of the compounds of embodiments of this invention are within the scope of the present invention.

Particularly, said salts are pharmaceutically accepted salts. Term "pharmaceutically accepted" means that the chemical or composition should be suitable for treating mammals chemically or toxicologically along with other ingredients forming the formulation.

EMBODIMENTS

In order to further understand embodiments of the present invention, the preferable embodiments of embodiments of the present invention are described in conjunction with the examples. However, it should be understood that, the descriptions are merely for further illustration of the features and advantages of embodiments of the present invention, and are limitations to the claims of embodiments of the present invention.

Technical effects are described in the particular examples, but the protected scope of embodiments of the present invention are not limited by the following examples.

The following examples provide further details of the inventions, but the protected scope is not limited by the examples.

Examples 1~40 Preparation of Flavone Derivatives 50 mL nitro-methane, 20 mmol β-propanedione derivatives represented by formula (a) and 1 mmol gallium triflate are added into a 100 mL four-open reaction bottle equipped with mechanical stirrer, drying tube, a thermometer and a dropping funnel. The reaction temperature is increased to 80° C. and the reaction is allowed to go on for 2 hours. TLC is employed to monitor the process of the reaction. When the reaction is finished, the reaction mixture is poured into 100 mL water. The resulting mixture is extracted with 20 dichloromethane for three times, and then the organic phases are combined and dehydrated with dehydrated sulfonic sodium. Then the solvent is removed by rotary evaporation, and the product is recrystallized with ethanol. Flavone derivative having a structure of Formula (I) is obtained. Refer to table 5, which shows the β-propanedione derivatives used in each of Examples 1~40.

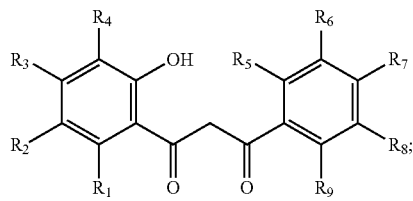

式(a)

Example 1 5,7,3',4',5'-penta methoxyl-flavone

ES-MS m/z: 373.2 (M+1), 1HNMR (CDCl3, 600 MHz) δ: 3.96 (3H, s, OCH3), 3.93 (3H, s, OCH3), 3.95 (3H, s, OCH3), 3.92 (3H, s, OCH3), 3.95 (3H, s, OCH3), 6.62 (1H, s, 3-H), 6.38 (1H, d, J=2.4 Hz, 6-H), 6.57 (1H, d, J=2.4 Hz, 8-H), 7.07 (1H, d, J=1.8 Hz, 2'-H), 7.07 (1H, d, J=1.8 Hz, 6'-H).

Example 2 5,3'-dihydroxyl-7,8,4'-trimethoxyl-flavone

ESI-MS m/z 343.2 [M−H]−, 1H NMR (DMSO-d6, 300 MHz) δ: 12.29 (1H, s, 5-OH), 7.40 (1H, dd, J=2.1, 7.2 Hz, 6'-H), 7.29 (1H, d, J=2.1 Hz, 2'-H), 7.26 (1H, d, J=7.2 Hz, 5'-H), 6.68 (1H, s, 3-H), 6.57 (1H, s, 6-H), 3.89 (3H, s, $OCH_3$), 3.87 (3H, s, $OCH_3$), 3.83 (3H, s, $OCH_3$).

TABLE 5 the β-propanedione derivatives used in each of Examples 1~40.

| Example | $R_1$ | $R_2$ | $R_3$ | $R_4$ | $R_5$ | $R_6$ | $R_7$ | $R_8$ | $R_9$ |
|---|---|---|---|---|---|---|---|---|---|
| 1 | —OCH3 | —H | —OCH3 | —H | —H | —OCH3 | —OCH3 | —OCH3 | —H |
| 2 | —OH | —H | —OCH3 | —OCH3 | —H | —OH | —OCH3 | —H | —H |
| 3 | —OCH3 | —H | —OCH3 | —OCH3 | —OCH3 | —OH | —H | —H | —H |
| 4 | —OCH3 | —H | —OCH3 | —H | —H | —OH | —OCH3 | —H | —H |
| 5 | —OCH3 | —H | —OH | —H | —H | —OCH3 | —OCH3 | —H | —H |
| 6 | —H | —OCH3 | —OCH3 | —OCH3 | —H | —H | —OCH3 | —H | —H |
| 7 | —OCH3 | —H | —OCH3 | —H | —H | —OCH3 | —OCH3 | —H | —H |
| 8 | —OCH3 | —OCH3 | —OCH3 | —OCH3 | —H | —H | —OCH3 | —H | —H |
| 9 | —OH | —H | —OCH3 | —OCH3 | —OCH3 | —OCH3 | —OCH3 | —H | —H |
| 10 | —OCH3 | —OCH3 | —OCH3 | —H | —H | —OCH3 | —OCH3 | —H | —H |
| 11 | —OH | —OCH3 | —OCH3 | —OCH3 | —H | —OCH3 | —OCH3 | —OH | —H |
| 12 | —OH | —H | —OCH3 | —OCH3 | —OCH3 | —H | —H | —OH | —H |
| 13 | —OCH3 | —OCH3 | —OCH3 | —H | —H | —OCH3 | —OCH3 | —OCH3 | —H |
| 14 | —OCH3 | —OCH3 | —OCH3 | —OCH3 | —H | —OCH3 | —OCH3 | —H | —H |
| 15 | —OCH3 | —OCH3 | —OCH3 | —OCH3 | —H | —OCH3 | —OCH3 | —OCH3 | —H |
| 16 | —NO2 | —H | C6H5CC— | —H | —H | —OH | C6H5O— | —C20H40Cl | —H |
| 17 | —C4H7S | —H | NH2CO— | —H | —H | —NH2 | CH3CH2— | —CHCH2 | —H |
| 18 | —C6H11 | —H | —C6H5 | —H | —H | CH3CH2— | —C5H10Cl | —C3H5 | —H |
| 19 | CH3CH2— | —H | —C5H10Cl | —H | —H | —C5H11 | C6H5CH2— | —OH | —H |
| 20 | —C3H5 | —H | C6H5CH2— | —H | —H | —NO2 | —CHCH2 | —CN | —H |
| 21 | —C3H6 | —H | CH3CH2— | —H | —H | —C20H40Cl | —C5H11 | —C6H5 | —H |
| 22 | —COOH | —H | —C3H5 | —H | —H | —CN | —F | —COOH | —H |
| 23 | —I | —H | —CH2CH2SO3H | —H | —H | —CONH2 | —COOH | —C3H7 | —H |
| 24 | —CH2CH2SO3H | —H | —I | —H | —H | —C3H5 | C10H21CH2O— | —C20H40Cl | —H |
| 25 | C6H5CH2— | —H | —C3H5 | —H | —H | —CN | —NO2 | C6H5CH2— | —H |
| 26 | —C5H11 | —H | —COOH | —H | —H | —COOH | —CN | —C3H5 | —H |
| 27 | —H | —OCH3 | —OCH3 | —OCH3 | —H | —OCH3 | —OCH3 | —H | —H |
| 28 | —H | —NH2 | —F | —CN | —H | —OH | —SCN | —H | —H |
| 29 | —H | —C20H40Cl | C6H5CC— | —NO2 | —H | —OH | C6H5O— | —H | —H |
| 30 | —H | —CHCH2 | NH2CO— | —C4H7S | —H | —NH2 | CH3CH2— | —H | —H |
| 31 | —H | —C3H5 | —C6H5 | —C6H11 | —H | CH3CH2— | —C5H10Cl | —H | —H |
| 32 | —H | —CN | C6H5CH2— | —C3H5 | —H | —NO2 | —CHCH2 | —H | —H |
| 33 | —H | —F | —COOH | —OH | —H | —C20H41 | —CCH | —H | —H |
| 34 | —H | —COOH | —C3H5 | —COOH | —H | —CN | —F | —H | —H |
| 35 | —H | —C3H7 | —CH2CH2SO3H | —I | —H | —CONH2 | —COOH | —H | —H |
| 36 | —OCH3 | —H | —OCH3 | —H | —H | —OCH3 | —OCH3 | —H | —H |
| 37 | —NH2 | —H | —F | —H | —H | —CN | —OH | —H | —H |
| 38 | —CHCH2 | —H | NH2CO— | —H | —H | —C4H7S | —NH2 | —H | —H |
| 39 | —C3H5 | —H | —C6H5 | —H | —H | —C6H11 | CH3CH2— | —H | —H |
| 40 | —COOH | —H | —C3H5 | —H | —H | —COOH | —CN | —H | —H |

The flavone derivatives prepared in Examples 1-40 are compounds 504, 587, 588, 548, 547, 589, 507, 590, 591, 527, 506, 586, 592, 515, 593, 356, 357, 358, 359, 360, 362, 363, 364, 371, 378, 381, 404, 405, 406, 407, 408, 410, 411, 413, 414, 454, 455, 457, 458 and 463 described above.

Among the above compounds, the characterizing data of compounds prepared in Examples 1~15 is shown as follows:

Example 3 2'-hydroxyl-5,7,8-trimethoxyl-flavone

ESI-MS m/z 329.2 [M+H]+, 1H NMR (DMSO-d6, 500 MHz) δ: 10.65 (1H, s, 2'-OH), 7.85 (1H, dd, J=1.5, 8.0 Hz, 6'-H), 7.37 (1H, dd, J=1.5, 8.5 Hz, 4'-H), 7.05 (1H, d, J=8.5 Hz, 3'-H), 7.02 (1H, t, J=8.0 Hz, 5'-H), 6.90 (1H, s, 3-H), 6.68 (1H, s, 6-H), 3.98 (3H, s, $OCH_3$), 3.87, (3H, s, $OCH_3$), 3.82 (3H, s, $OCH_3$).

Example 4 3'-hydroxyl-5,7,4'-trimethoxyl-flavone

ES-MS m/z: 329.0 (M+1), 1HNMR (CDCl$_3$, 600 MHz) δ: 3.877 (3H, s, OCH$_3$), 3.838 (3H, s, OCH$_3$), 3.806 (3H, s, OCH$_3$), 6.528 (1H, s, 3-H), 6.470 (1H, d, J=2.4 Hz, 6-H), 6.780 (1H, d, J=2.4 Hz, 8-H), 7.376 (1H, d, J=1.8 Hz, 2'-H), 7.562 (1H, d, J=9.0 Hz, 5'-H), 7.471 (1H, dd, J=9.0 Hz, 1.8 Hz, 6'-H).

Example 5 7-hydroxyl-5,3',4'-trimethoxyl-flavone

ES-MS m/z: 329.0 (M+1), 1HNMR (CDCl$_3$, 600 MHz) δ: 3.79 (3H, s, OCH$_3$), 3.86 (3H, s, OCH$_3$), 3.82 (3H, s, OCH$_3$), 6.672 (1H, s, 3-H), 6.375 (1H, d, J=2.4 Hz, 6-H), 6.578 (1H, d, J=2.4 Hz, 8-H), 7.467 (1H, d, J=1.8 Hz, 2'-H), 7.562 (1H, d, J=9.0 Hz, 5'-H), 7.575 (1H, dd, J=9.0 Hz, 1.8 Hz, 6'-H).

Example 6 6,7,8,4'-tetramethoxyl-flavone

ES-MS m/z: 389.2 [M+1]+, 1H NMR (CDCl$_3$, 400 MHz) δ: 3.90 (s, 3H, OCH$_3$), 3.96 (s, 3H$_2$OCH$_3$), 3.98 (s, 3H, OCH$_3$), 4.11 (s, 3H, OCH$_3$), 6.60 (s, 1H, 3-H), 7.04 (d, J=8.8 Hz, 2H, 3',5'-H), 7.90 (d, J=8.8 Hz, 2H, 2',6'-H).

Example 7 5,7,3',4'-tetramethoxyl-flavone

ES-MS m/z: 343.1 (M+1), 1HNMR (CDCl$_3$, 600 MHz) δ: 3.90 (3H, s, OCH$_3$), 3.94 (3H, s, OCH$_3$), 3.95 (3H, s, OCH$_3$), 3.94 (3H, s, OCH$_3$), 6.58 (1H, s, 3-H), 6.35 (1H, d, J=2.4 HZ, 6-H), 6.53 (1H, d, J=2.4 HZ, 8-H), 7.26 (1H, d, J=1.8 HZ, 2'-H), 6.92 (1H, d, J=9.0 HZ, 5'-H), 7.46 (dd, 1H, J=9.0 Hz, 1.8 Hz, 6'-H).

Example 8 5,6,7,8,4'-penta methoxyl-flavone

ES-MS m/z: 373.3 [M+1]+, 1HNMR (CDCl$_3$, 400 MHz) δ: 3.89 (s, 3H, OCH$_3$), 3.95 (s, 6H, OCH$_3$), 4.02 (s, 3H, OCH$_3$), 4.10 (s, 3H, OCH$_3$), 6.61 (s, 1H, 3-H), 7.03 (d, J=8.8 Hz, 2H, 3',5'-H), 7.88 (d, J=8.8 Hz, 2H, 2',6'-H).

Example 9 5-hydroxyl-7,8,2',3',4'-penta methoxyl-flavone

ESI-MS m/z 389.0 [M+H]+, 1H NMR (CDCl$_3$, 500 MHz) δ: 12.72 (1H, br s, 5-OH), 7.65 (d, J=8.8 Hz, 6'-H), 6.92 (1H, s, 3-H), 6.83 (1H, d, J=8.8 Hz, 5'-H), 6.42 (1H, s, 6-H), 3.98 (3H, s, OCH$_3$), 3.95 (6H, s, OCH$_3$), 3.91 (3H, s, OCH$_3$), 3.90 (3H, s, OCH$_3$).

Example 10 5,6,7,3',4'-penta methoxyl-flavone

1HNMR (CDCl$_3$, 600 MHz) δ: 4.01 (3H, S, OCH$_3$), 3.96 (3H, S, OCH$_3$), 3.99 (3H, S, OCH$_3$), 3.97 (3H, S, OCH$_3$), 3.96 (3H, S, OCH$_3$), 6.62 (1H, S, 3-H), 6.44 (1H, S, 8-H), 7.42 (1H, d, J=1.8 HZ, 2'-H), 6.98 (1H, d, J=8.4 HZ, 5'-H), 7.59 (1H, dd, J=8.4, 1.8 Hz, 6'-H).

Example 11 5-hydroxyl-6,7,8,3',4'-penta methoxyl-flavone

1HNMR (CDCl$_3$, 600 MHz) δ: 12.20 (1H, S, 5-OH), 3.95 (3H, s, OCH$_3$), 4.12 (3H, s, OCH$_3$), 3.96 (3H, S, OCH$_3$), 3.99 (3H, S, OCH$_3$), 3.97 (3H, S, OCH$_3$), 6.61 (1H, S, 3-H), 7.41 (1H, d, J=2.4 Hz, 2'-H), 6.99 (1H, d, J=8.4 Hz, 5'-H), 7.57 (1H, dd, J=2.4, 8.4 Hz, 6'-H).

Example 12 5,5'-dihydroxyl-7,8,2'-trimethoxyl-flavone

ESI-MS m/z: 345.0 [M+H]+, 1H NMR (DMSO-d6, 500 MHz) δ: 12.65 (1H, s, 5-OH), 9.48 (1H, s, 5'-OH), 7.34 (1H, d, J=2.9 Hz, 6'-H), 7.11 (1H, d, J=8.9 Hz, 3'-H), 6.99 (1H, dd, J=2.9, 8.9 Hz, 4'-H), 6.92 (1H, s, 3-H), 6.60 (1H, s, 6-H), 3.92 (3H, s, OCH$_3$), 3.86 (3H, s, OCH$_3$), 3.82 (3H, s, OCH$_3$).

Example 13 5,6,7,3',4',5'-hexamethoxyl-flavone

ES-MS m/z: 403.1 (M+1), 1HNMR (CDCl$_3$, 600 MHz) δ: 3.97 (3H, s, OCH$_3$), 4.00 (3H, s, OCH$_3$), 4.02 (3H, s, OCH$_3$), 3.96 (3H, s, OCH$_3$), 3.92 (3H, s, OCH$_3$), 3.96 (3H, s, OCH$_3$), 6.65 (1H, s, 3-H), 6.45 (1H, s, 8-H), 7.19 (1H, d, J=2.4 Hz, 2'-H), 7.19 (1H, d, J=2.4 Hz, 6'-H).

Example 14 5,6,7,8,3',4'-hexamethoxyl-flavone

ES-MS m/z: 403.0 [M+1]+, 1H NMR (CDCl$_3$, 400 MHz) δ: 3.96 (s, 3H$_2$OCH$_3$), 3.97 (s, 3H, OCH$_3$), 3.98 (s, 3H, OCH$_3$), 4.03 (s, 3H$_2$OCH$_3$), 4.10 (s, 3H, OCH$_3$), 4.11 (s, 3H, OCH$_3$), 6.63 (s, 1H, 3-H), 7.42 (d, J=2.0 Hz, 1H, 2'-H), 7.00 (d, J=8.8 Hz, 1H, 5'-H), 7.58 (dd, J=8.8, 2.4 Hz, 1H, 6'-H).

Example 15 5,6,7,8,3',4',5'-heptamethoxyl-flavone

1H-NMR (CDCl$_3$, 500 MHz) δ: 7.117 (2H, s, 2',6'-H), 6.165 (1H, s, 3-H), 4.111 (6H, s, OCH$_3$), 4.103 (6H, s, OCH$_3$), 3.192 (6H, s, OCH$_3$), 3.198 (3H, s, OCH$_3$).

On the basis of the data disclosed, embodiments of the present invention shows that compounds 586, 587, 588, 548, 547, 589, 507, 590, 591, 527, 506, 504, 592, 515, 593, 356, 357, 358, 359, 360, 362, 363, 364, 371, 378, 381, 404, 405, 406, 407, 408, 410, 411, 413, 414, 454, 455, 457, 458 and 463 may be prepared by the above method.

Example 41

Standard sample 3,5,6,7,8,3',4'-heptamethoxyl-flavone, i.e., compound 512 described above, is purchased from Shanghai Tauto Biotech Co., Ltd.

Examples 42~71 Preparation of Flavanone Derivatives

Substituted acetophenone having a structure of formula (b), substituted benzaldehyde having a structure of formula (c) and boric acid are solved in glycol. The mixture is heated to 100° C. and is allowed to react under stirring for 1 hour. The obtained reaction product is solved in ethanol, and is purified with column chromatography to obtain a flavanone derivative having a structure of Formula (II). Please see table 6, which shows the substituted acetophenone and substituted benzaldehyde used in each of Example 42~71.

Formula (b)

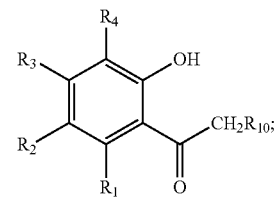

-continued

Formula (c)

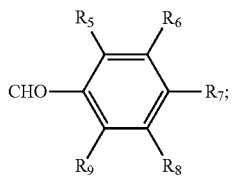

| example | R₁ | R₂ | R₃ | R₄ | R₅ | R₆ | R₇ | R₈ | R₉ | R₁₀ |
|---|---|---|---|---|---|---|---|---|---|---|
| 42 | —OH | —OCH₃ | —OCH₃ | —OCH₃ | —H | —H | —OCH₃ | —H | —H | —H |
| 43 | —OH | —OCH₃ | —OCH₃ | —OCH₃ | —H | —OCH₃ | —OCH₃ | —H | —H | —H |
| 44 | —OCH₃ | —H | —OCH₃ | —OCH₃ | —H | —OCH₃ | —OCH₃ | —H | —H | —H |
| 45 | —H | —OCH₃ | —OCH₃ | —OCH₃ | —H | —OCH₃ | —OCH₃ | —H | —H | —H |
| 46 | —OCH₃ | —H | —OCH₃ | —H | —H | —OCH₃ | —OCH₃ | —OCH₃ | —H | —H |
| 47 | —OCH₃ | —OCH₃ | —OCH₃ | —OCH₃ | —H | —H | —OCH₃ | —H | —H | —H |
| 48 | —OCH₃ | —OCH₃ | —OCH₃ | —OCH₃ | —H | —OCH₃ | —OCH₃ | —H | —H | —H |
| 49 | —OCH₃ | —H | —OCH₃ | —H | —H | —OCH₃ | —H | —OCH₃ | —H | —H |
| 50 | —OH | —H | —OH | —H | —H | —COOH | —OCH₃ | —OH | —H | —H |
| 51 | —NO₂ | —H | —OH | —H | —H | —C₆H₅ | —C₄H₇S | —C₃H₇ | —H | —H |
| 52 | —COOH | —H | —H | —H | —H | —C₅H₁₁ | —H | —C₃H₆ | —H | —H |
| 53 | CH₃CH₂— | —H | —H | —H | —H | —F | —COOH | —H | —H | —H |
| 54 | —H | —NO₂ | —SCN | —C₄H₈N | —H | CH₃CH₂— | C₆H₅CO— | —H | —H | —H |
| 55 | —H | —CH₂CH₂SO₃H | —C₄H₈N | —NH₂ | —H | —SCN | —OCH₃ | —H | —H | —H |
| 56 | —H | C₆H₅CC— | —NO₂ | —SCN | —H | —C₂₀H₄₀Cl | —OH | —H | —H | —H |
| 57 | —H | NH₂CO— | —C₄H₇S | C₆H₅O— | —H | —CHCH₂ | —NH₂ | —H | —H | —H |
| 58 | —H | CH₃CH₂— | —C₃H₆ | —CCH | —H | —C₆H₅ | —C₂₀H₄₀Cl | —H | —H | —H |
| 59 | —H | CH₃CH₂— | —C₃H₆ | —CCH | —H | —C₆H₅ | —C₂₀H₄₀Cl | —H | —H | —H |
| 60 | —H | —I | —H | —C₃H₅ | —H | —COOH | —H | —H | —H | —H |
| 61 | —OH | —H | —NO₂ | —H | —H | —OCH₃ | —C₃H₇ | —H | —H | —H |
| 62 | —OH | —H | —H | —H | —H | —OH | —OCH₃ | —H | —H | —H |
| 63 | —NO₂ | —H | —H | —H | —H | —CH₃ | C₆H₅O— | —H | —H | —H |
| 64 | —OH | —OCH₃ | —OCH₃ | —OCH₃ | —H | —OCH₃ | —OCH₃ | —H | —H | —H |
| 65 | —OCH₃ | —OCH₃ | —OCH₃ | —H | —H | —H | —OCH₃ | —H | —H | —H |
| 66 | —OCH₃ | —H | —OCH₃ | —H | —OCH₃ | —OCH₃ | —OCH₃ | —OCH₃ | —H | —H |
| 67 | —H | —OCH₃ | —OCH₃ | —OCH₃ | —H | —OCH₃ | —OCH₃ | —OCH₃ | —OCH₃ | —H |
| 68 | —OH | —OCH₃ | —OCH₃ | —OCH₃ | —H | —OCH₃ | —OCH₃ | —OCH₃ | —OCH₃ | —OCH₃ |
| 69 | —H | —OCH₃ | —OCH₃ | —OCH₃ | —H | —OCH₃ | —OCH₃ | —OCH₃ | —OH | —OCH₃ |
| 70 | —C₃H₇ | —H | —OH | —H | —H | —NO₂ | —C₆H₅ | —H | —H | —H |
| 71 | —OH | —H | —OH | —H | —H | —OH | —OH | —H | —H | —H |

The flavanone derivatives prepared in Examples 42~71 are compounds 594, 595, 551, 505, 508, 596, 597, 391, 366, 367, 397, 398, 418, 419, 424, 425, 430, 433, 449, 485, 501, 491, 552, 553, 554, 564, 570, 577, 467 and 484 described above.

Among the above compounds, the characterizing data of compounds prepared in Examples 42~48 is shown as follows:

Preparation Example 42
5-hydroxyl-6,7,8,4'-tetramethoxyl-flavanone m/z: 361 [M+1]+, 1H NMR (CDCl₃, 400 MHz) δ: 5.40 (dd, J=12.4, 2.8 Hz, 1H, 2-H), 2.87 (dd, J=17.2, 2.8 Hz, 1H, 3-Ha), 3.11 (dd, J=17.2, 12.4 Hz, 1H, 3-Hb), 3.79 (s, 3H₂OCH₃), 3.84 (s, 3H, OCH₃), 3.86 (s, 3H, OCH₃), 4.09 (s, 3H, OCH₃), 6.95 (d, J=8.8 Hz, 1H, 5'-H), 7.40 (d, J=8.8 Hz, 2H, 2',6'-H).

Preparation Example 43 5-hydroxyl-6,7,8,3',4'-penta methoxyl-flavanone m/z: 391[M+1]+, 1H NMR (CDCl₃, 400 MHz) δ: 5.40 (dd, J=12.4, 2.8 Hz, 1H, 2-H), 2.90 (dd, J=13.2, 3.2 Hz, 1H, 3-Ha), 3.12 (dd, J=16.8, 12.4 Hz, 1H, 3-Hb), 3.80 (s, 3H, OCH₃), 3.86 (s, 3H, OCH₃), 3.91 (s, 6H₂OCH₃), 4.09 (s, 3H, OCH₃), 6.90 (d, J=8.4 Hz, 1H, 5'-H), 7.00 (d, J=8.0 Hz, 2H, 2',6'-H).

Preparation Example 44 5,7,8,3',4'-penta methoxyl-flavanone

1HNMR (CDCl₃) δ: 3.96 (3H, s, OCH₃), 3.93 (3H, s, OCH₃), 3.95 (3H, s, OCH₃), 3.92 (3H, s, OCH₃), 3.95 (3H, s, OCH₃), 5.45 (1H, dd, J=12.0, 2.4 Hz, 2-H), 3.05 (1H, dd, J=12.0, 16.2 Hz, 3-Ha), 2.63 (1H, dd, J=16.2, 2.4 Hz, 3-Hb), 6.34 (1H, S, 6-H), 7.12 (1H, d, J=1.8 Hz, 2'-H), 6.92 (1H, d, J=8.4 Hz, 5'-H), 7.02 (1H, dd, J=8.4, 1.8 Hz, 6'-H).

Preparation Example 45 6,7,8,3',4'-penta methoxyl-flavanone

1HNMR (CDCl₃) δ: 3.802 (3H, S, OCH₃), 3.923 (3H, S, OCH₃), 3.943 (3H, S, OCH₃), 3.904 (3H, S, OCH₃), 3.893 (3H, S, OCH₃), 5.408 (1H, d, J=8.4 Hz, 2-H), 3.005 (1H, dd, J=12.0, 16.2 Hz, 3-Ha), 2.860 (1H, d, J=16.8 Hz, 3-Hb), 6.134 (1H, S, 5-H), 7.025 (1H, d, J=2.4 Hz, 2'-H), 6.880 (1H, d, J=7.8 Hz, 5'-H), 7.57 (1H, dd, J=2.4, 7.8 Hz, 6'-H).

Preparation Example 46 5,7,3',4',5'-penta methoxyl-flavanone

1HNMR (CDCl₃) δ: 3.905 (3H, S, OCH₃), 3.862 (3H, S, OCH₃), 3.896 (3H, S, OCH₃), 3.833 (3H, S, OCH₃), 3.896 (3H, S, OCH₃), 5.326 (1H, dd, J=13.2, 2.4 Hz, 2-H), 3.020 (1H, dd, J=16.2, 13.2 Hz, 3-Ha), 2.803 (1H, dd, J=16.6, 2.4 Hz, 3-Hb), 6.112 (1H, d, J=2.4 Hz, 6-H), 6.178 (1H, d, J=1.8 Hz, 8-H), 6.678 (1H, d, J=1.8 Hz, 2'-H), 6.678 (1H, d, J=1.8 Hz, 6'-H).

Preparation Example 47 5,6,7,8,4'-penta methoxyl-flavanone m/z: 375 [M+1]+, 1H NMR (CDCl₃, 400 MHz) δ: 5.39 (dd, J=12.8, 2.8 Hz, 1H, 2-H), 2.84 (dd, J=16.8, 3.2 Hz, 1H, 3-Ha), 3.04 (dd, J=16.8, 12.8 Hz, 1H, 3-Hb), 3.83 (s, 3H, OCH$_3$), 3.84 (s, 3H, OCH$_3$), 3.85 (s, 3H, OCH$_3$), 3.90 (s, 6H, OCH$_3$), 4.06 (s, 3H, OCH$_3$), 6.95 (d, J=8.8 Hz, 2H, 3',5'-H), 7.40 (d, J=8.4 Hz, 2H, 2',6'-H).

Preparation Example 48
5,6,7,8,3',4'-hexamethoxyl-flavanone m/z: 405[M+1]+, 1H NMR (CDCl$_3$, 400 MHz) δ: 5.40 (dd, J=13.2, 3.2 Hz, 1H, 2-H) 2.88 (dd, J=16.8, 2.8 Hz, 1H, 3-Ha), 3.03 (dd, J=16.8, 13.2 Hz, 1H, 3-Hb), 3.85 (s, 6H, OCH$_3$), 3.90 (s, 3H$_2$OCH$_3$), 3.91 (s, 6H, OCH$_3$), 4.06 (s, 3H, OCH$_3$), 6.90 (d, J=8.8 Hz, 1H, 5'-H), 7.01 (d, J=6.4 Hz, 2H, 2',6'-H).

On the basis of the data disclosed, embodiments of the present invention shows that compounds 594, 595, 551, 505, 508, 596, 597, 391, 366, 367, 397, 398, 418, 419, 424, 425, 430, 433, 449, 485, 501, 491, 552, 553, 554, 564, 570, 577, 467 and 484 may be prepared by the above method.

Experimental Examples

As the first in the technical field, embodiments of the present invention discovers and proves that the compounds having general formulas (I-VII) of embodiments of the present invention show significant inhibition effect on central nervous system, and shows bioactivities in sedation and hypnosis, thereby completing embodiments of the present invention, by use of animal models of sedative and hypnotic drugs, which include: (1) general behavior observation; (2) voluntary action experiment; (3) elongation of the sleep time under pentobarbital sodium; and (4) experimentations with pentobarbital sodium doses below the threshold.

1. MATERIALS AND METHODS 1.1 Animals for experiments: Kunming mice, weighting 18.9~22.2 g for females, and 20.2~23.0 g for males, licensed under SCXK-(Ji) 2007-0003, and provided by The experimental animal centre, Jilin University.

1.2 Chemicals for experiments: The flavone derivatives provided in Examples 1-41 and the flavanone derivatives provided in Examples 42-71 are all formulated with 0.5% sodium carboxymethyl cellulose as solutions with required concentrations.

1.3 Grouping of animals: 6420 animals are employed in the entire experiments and 2140 of the animals are randomly divided into 214 groups by gender, and the 2145 groups include: control group, low dosage group for each experimental drugs (25 mg/kg), medium dosage group for each experimental drugs (50 mg/kg), and high dosage group for each experimental drugs (100 mg/kg). Each group has 10 animals and either female or male constitutes half of the group. The groups are used in behavior observation and voluntary action observation. The other 4280 animals are randomly divided into 214 groups by gender respectively (the grouping way is the same with that described above). Each group has 20 animals and either female or male constitutes half of the group. In each group, 10 animals are used in hypnosis experimentations with pentobarbital sodium doses below the threshold, and the other 10 animals are used hypnosis experimentations with pentobarbital sodium doses at the threshold.

1.4 Experimental instrument and agents: ZIL-2 mice autonomic activity meter, production of Institute of Materia Medica of Chinese Academy of Medical Sciences; pentobarbital sodium, Lot: 100808, 25 g/bottle, Beijing Chemical Reagent Company equipment imported from Germany.

1.5 Experimental Methods
1.5.1 General Behavior Observation

Within 60 min after the drug is intragastric administered in mice for single time, general animal behavior, posture, gait, drooling, muscle trembling, quiet, drowsiness and sleep and other changes are observed directly.

1.5.2 Influence on Autonomic Activity of Normal Mice

After observing the general behavior, in 1 h, 2 h and 24 h after drug administration, respectively, ZIL-2 mice autonomic activity meter is put respectively. Number of autonomic activities of each group of mice is measured within 10 min. Results among groups are compared.

1.5.3 Influence on Hypnosis Effect with Mice Pentobarbital Sodium Doses Below the Threshold The drug is intragastric administered in mice for single time, 2 animals of each group are given drug per round with the dosing interval of 40 min (±5 min). According to the administration round, in 60 min (±5 min) of each round after the drug administration, the animals were intraperitoneally injected 0.3% sodium pentobarbital 25 mg/kg, respectively. Sleep condition of the animals were observed within 30 min (under sleep determination standard of loss of righting reflex more than 1 min). After animals undergo loss of righting reflex, number of the animals is recorded, to calculate sleep percentage.

1.5.4 Influence on Hypnosis Effect with Mice Pentobarbital Sodium Doses at the Threshold The drug is intragastric administered in mice for single time, 2 animals of each group are given drug per round with the dosing interval of 40 min (±5 min). According to the administration round, in 60 min (±5 min) of each round after the drug administration, the animals were intraperitoneally injected 0.3% sodium pentobarbital 50 mg/kg, respectively. Time to fall asleep (sleep latency) and sleep duration of the animals were recorded within under sleep determination standard of loss of righting reflex more than 1 min.

1.5.5 Data Statistic and Processing Method

Number of autonomic activities is detected by leneve Test for homogeneity of variance. If the homogeneity of variance is good (P>0.05), statistical analysis is performed with ANOVA. If ANOVA have statistical significance (P≤0.05), Dunnett's test for multiple comparisons analysis is performed. Number of animals of sleeping mice is applied of ANOVA. Incidence rate of animal asleep is applied of χ2 test. Sleep latency and sleep duration are recorded in min, averaged by group, represented by standard deviation, and undergo statistical analysis using ANOVA.

2. EXPERIMENTAL RESULTS 2.1 Influence on the General Behavior of Mice the animals of control group behave and activate freely, no abnormal posture, gait, salivation, muscle trembling and other phenomena occur; animals of low dose of each test drug began to appear with varying degrees of reducing activity after 30 min from drug administration, no lethargy appears; animals of middle dose of each test drug began to appear quiet, reduced activity in about 20 min after drug administration, and most animals appeared drowsiness symptoms in 25~30 min after drug administration, did not enter sleep; animals of high dose of each test drug began to appear quiet, reduced activity in about 20 min after drug administration, and most animals appeared drowsiness symptoms in 25~30 min after drug administration, some animals went to sleep.

2.2 Influence on the Autonomic Activity of Mice

Compared with the control group, autonomic activities of low dose group, middle dose group and high dose group of drug administration were significantly reduced ($P<0.05$~$P<0.001$) in 1 h and 2 h after drug administration and dose-related. Each group of drug administration were not significantly different ($P>0.05$), see Table 7. Table 7 shows test result of influence on the autonomic activity of mice of compounds of Examples 1 to 71 in embodiments of the present invention.

TABLE 7 influence on the autonomic activities of mice of compounds in embodiments of the present invention ($\bar{x} \pm s$, n = 10)

| Group | Dosage (mg/kg) | Times of activities in 1 h after drug administration/ 10 min | Times of activities in 2 h after drug administration/ 10 min | Times of activities in 24 h after drug administration/ 10 min |
|---|---|---|---|---|
| Control Group | 0 | 367.2 ± 75.1 | 356.8 ± 79.2 | 330.1 ± 77.2 |
| Example 1 | 25 | 215.3 ± 40.1** | 211.2 ± 36.3** | 274.4 ± 81.2 |
|  | 50 | 137.1 ± 52.3*** | 168.5 ± 57.9*** | 275.2 ± 79.3 |
|  | 100 | 98.2 ± 41.9*** | 96.2 ± 55.7*** | 301.2 ± 80.7 |
| Example 2 | 25 | 320.1 ± 54.7 | 293.5 ± 40.8* | 302.7 ± 77.5 |
|  | 50 | 295.3 ± 41.8* | 254.2 ± 41.1** | 306.2 ± 90.6 |
|  | 100 | 281.3 ± 47.6** | 223.5 ± 45.7** | 311.4 ± 80.3 |
| Example 3 | 25 | 283.4 ± 45.8* | 264.7 ± 46.1* | 305.8 ± 80.9 |
|  | 50 | 236.2 ± 41.5** | 246.3 ± 49.1** | 298.8 ± 71.0 |
|  | 100 | 180.5 ± 35.3*** | 174.7 ± 40.5*** | 286.9 ± 90.4 |
| Example 4 | 25 | 258.2 ± 44.2** | 250.3 ± 53.9* | 309.1 ± 76.1 |
|  | 50 | 219.3 ± 42.7** | 223.5 ± 41.3** | 318.4 ± 96.3 |
|  | 100 | 124.2 ± 49.1*** | 127.2 ± 41.9*** | 303.2 ± 90.1 |
| Example 5 | 25 | 265.2 ± 50.1** | 243.2 ± 42.8** | 292.8 ± 82.1 |
|  | 50 | 175.4 ± 50.3*** | 190.2 ± 56.8*** | 295.3 ± 91.3 |
|  | 100 | 120.2 ± 39.0*** | 116.3 ± 49.2*** | 283.5 ± 94.0 |
| Example 6 | 25 | 330.1 ± 51.2 | 314.5 ± 56.7 | 338.1 ± 96.3 |
|  | 50 | 286.7 ± 61.7* | 279.5 ± 48.2* | 311.5 ± 91.5 |
|  | 100 | 238.3 ± 36.3** | 249.8 ± 45.8** | 308.2 ± 82.7 |
| Example 7 | 25 | 248.5 ± 55.1** | 234.1 ± 45.8** | 303.4 ± 75.8 |
|  | 50 | 184.7 ± 52.6*** | 164.4 ± 45.8*** | 318.5 ± 83.6 |
|  | 100 | 125.2 ± 44.5*** | 122.2 ± 48.6*** | 329.8 ± 53.2 |
| Example 8 | 25 | 301.3 ± 43.5* | 290.2 ± 39.6* | 286.4 ± 75.2 |
|  | 50 | 262.1 ± 55.5** | 244.7 ± 53.9** | 299.8 ± 76.4 |
|  | 100 | 185.7 ± 41.6*** | 167.2 ± 48.5*** | 280.4 ± 84.2 |
| Example 9 | 25 | 258.4 ± 60.2** | 241.1 ± 34.1** | 314.2 ± 67.9 |
|  | 50 | 183.5 ± 45.9*** | 194.3 ± 45.1*** | 317.2 ± 80.9 |
|  | 100 | 129.0 ± 40.2*** | 126.3 ± 39.8*** | 323.5 ± 62.4 |
| Example 10 | 25 | 289.3 ± 50.1* | 275.6 ± 44.1* | 315.6 ± 76.3 |
|  | 50 | 257.2 ± 61.3** | 260.1 ± 58.2** | 325.3 ± 80.2 |
|  | 100 | 131.2 ± 30.8*** | 231.6 ± 44.2** | 304.1 ± 82.5 |
| Example 11 | 25 | 243.1 ± 53.5** | 237.3 ± 45.3** | 291.7 ± 72.5 |
|  | 50 | 187.2 ± 41.4*** | 179.7 ± 46.0*** | 287.8 ± 89.1 |
|  | 100 | 115.9 ± 48.5*** | 126.7 ± 48.7*** | 315.2 ± 75.4 |
| Example 12 | 25 | 255.9 ± 39.8* | 284.2 ± 41.7* | 303.1 ± 69.1 |
|  | 50 | 179.5 ± 51.4*** | 168.5 ± 54.3*** | 317.9 ± 55.3 |
|  | 100 | 153.7 ± 48.4*** | 135.9 ± 48.7*** | 302.1 ± 89.0 |
| Example 13 | 25 | 293.2 ± 47.1* | 278.5 ± 42.8* | 302.8 ± 67.2 |
|  | 50 | 280.7 ± 61.3* | 278.6 ± 47.5* | 309.2 ± 81.3 |
|  | 100 | 247.2 ± 35.6** | 225.3 ± 44.2** | 291.5 ± 69.5 |
| Example 14 | 25 | 289.9 ± 42.3* | 281.1 ± 41.6* | 313.2 ± 74.4 |
|  | 50 | 178.6 ± 40.2*** | 183.3 ± 51.3*** | 324.7 ± 79.6 |
|  | 100 | 159.1 ± 48.1*** | 133.9 ± 49.7*** | 322.6 ± 61.2 |
| Example 15 | 25 | 287.1 ± 39.1* | 255.1 ± 42.9* | 308.5 ± 75.2 |
|  | 50 | 254.7 ± 41.2** | 239.9 ± 42.6* | 317.4 ± 95.6 |
|  | 100 | 179.6 ± 44.3*** | 152.5 ± 36.9*** | 287.8 ± 89.1 |
| Example 16 | 25 | 319.2 ± 55.4 | 290.6 ± 41.2* | 313.5 ± 68.2 |
|  | 50 | 295.5 ± 41.3* | 250.4 ± 41.4** | 314.1 ± 82.3 |
|  | 100 | 273.4 ± 48.3** | 224.7 ± 46.3** | 324.7 ± 79.7 |
| Example 17 | 25 | 284.9 ± 49.3* | 280.1 ± 42.7* | 306.2 ± 81.3 |
|  | 50 | 176.6 ± 50.2*** | 189.3 ± 57.3*** | 291.5 ± 70.0 |
|  | 100 | 153.1 ± 38.4*** | 135.9 ± 48.7*** | 302.1 ± 89.0 |
| Example 18 | 25 | 333.7 ± 37.2 | 319.0 ± 46.5 | 314.4 ± 79.6 |
|  | 50 | 289.7 ± 56.0* | 280.1 ± 42.0* | 315.8 ± 75.4 |
|  | 100 | 232.2 ± 35.6** | 259.1 ± 40.1** | 302.1 ± 89.0 |
| Example 19 | 25 | 282.2 ± 46.5* | 265.0 ± 45.3* | 302.8 ± 83.2 |
|  | 50 | 234.7 ± 40.1** | 243.5 ± 48.3** | 306.2 ± 81.3 |
|  | 100 | 229.6 ± 34.8** | 172.5 ± 39.2*** | 287.8 ± 89.1 |
| Example 20 | 25 | 320.3 ± 49.7 | 293.6 ± 45.1* | 317.4 ± 79.6 |
|  | 50 | 283.7 ± 51.3* | 278.6 ± 47.5* | 305.2 ± 75.4 |
|  | 100 | 267.2 ± 55.3** | 250.3 ± 47.1** | 305.7 ± 79.7 |
| Example 21 | 25 | 240.1 ± 40.0** | 235.1 ± 35.7** | 269.1 ± 81.7 |
|  | 50 | 162.4 ± 52.3*** | 150.0 ± 57.8*** | 283.9 ± 76.8 |
|  | 100 | 119.7 ± 42.1*** | 108.4 ± 56.4*** | 314.4 ± 79.6 |
| Example 22 | 25 | 320.3 ± 54.3 | 291.3 ± 42.0* | 301.3 ± 76.6 |
|  | 50 | 299.4 ± 42.7* | 255.3 ± 41.3** | 302.6 ± 91.8 |
|  | 100 | 281.5 ± 48.7** | 225.6 ± 45.3** | 315.4 ± 78.2 |
| Example 23 | 25 | 287.2 ± 45.4* | 263.2 ± 45.2* | 307.2 ± 82.1 |
|  | 50 | 229.9 ± 40.6*** | 244.7 ± 47.6** | 300.7 ± 71.4 |
|  | 100 | 135.5 ± 35.7*** | 181.0 ± 38.2*** | 292.8 ± 90.5 |
| Example 24 | 25 | 319.3 ± 50.2 | 321.7 ± 57.2 | 324.1 ± 96.5 |
|  | 50 | 284.3 ± 64.2* | 279.5 ± 48.3* | 315.5 ± 92.3 |
|  | 100 | 242.2 ± 34.9** | 248.9 ± 45.9** | 308.1 ± 82.8 |
| Example 25 | 25 | 286.3 ± 48.9* | 279.9 ± 41.7* | 295.2 ± 82.3 |
|  | 50 | 185.3 ± 51.1*** | 190.2 ± 56.9*** | 296.3 ± 91.1 |
|  | 100 | 135.6 ± 39.4*** | 136.8 ± 47.9*** | 281.6 ± 93.7 |
| Example 26 | 25 | 310.7 ± 59.5 | 279.0 ± 32.2* | 313.5 ± 68.8 |
|  | 50 | 284.7 ± 46.1* | 267.1 ± 43.5** | 314.1 ± 82.3 |
|  | 100 | 263.6 ± 42.4** | 245.6 ± 40.8** | 322.6 ± 61.2 |
| Example 27 | 25 | 291.3 ± 52.1* | 282.2 ± 41.5* | 293.6 ± 82.9 |
|  | 50 | 169.6 ± 51.3*** | 193.2 ± 56.4** | 295.7 ± 92.3 |
|  | 100 | 124.2 ± 39.4*** | 138.9 ± 48.9*** | 278.6 ± 92.7 |
| Example 28 | 25 | 289.8 ± 50.1* | 278.3 ± 42.9* | 315.2 ± 76.3 |
|  | 50 | 248.9 ± 61.1** | 260.8 ± 58.1** | 327.5 ± 80.7 |
|  | 100 | 144.2 ± 32.5*** | 237.5 ± 44.3** | 308.7 ± 84.7 |
| Example 29 | 25 | 292.6 ± 45.7* | 311.4 ± 54.2 | 309.3 ± 76.5 |
|  | 50 | 251.9 ± 41.9** | 247.8 ± 41.9** | 318.5 ± 93.6 |
|  | 100 | 218.8 ± 45.9** | 263.2 ± 49.4** | 311.2 ± 92.5 |
| Example 30 | 25 | 289.2 ± 45.7* | 264.1 ± 42.2* | 302.2 ± 87.3 |
|  | 50 | 235.8 ± 42.1** | 244.5 ± 48.2** | 294.5 ± 70.6 |
|  | 100 | 134.6 ± 35.7*** | 173.5 ± 39.2*** | 288.8 ± 92.1 |
| Example 31 | 25 | 287.4 ± 41.2* | 302.4 ± 52.7 | 312.5 ± 79.3 |
|  | 50 | 247.2 ± 40.5* | 261.3 ± 41.5* | 323.6 ± 91.2 |
|  | 100 | 232.3 ± 50.2** | 269.4 ± 42.9** | 313.1 ± 89.2 |
| Example 32 | 25 | 332.1 ± 47.8 | 321.3 ± 53.9 | 327.8 ± 93.9 |
|  | 50 | 270.2 ± 59.3* | 269.3 ± 50.3* | 334.7 ± 95.6 |
|  | 100 | 245.9 ± 38.8** | 258.9 ± 49.9** | 322.7 ± 88.5 |
| Example 33 | 25 | 304.9 ± 39.2* | 298.2 ± 35.6* | 273.2 ± 80.8 |
|  | 50 | 266.4 ± 51.6** | 247.1 ± 58.3** | 284.7 ± 78.7 |
|  | 100 | 179.0 ± 49.1*** | 165.8 ± 52.3*** | 318.4 ± 80.5 |
| Example 34 | 25 | 292.2 ± 49.3* | 276.2 ± 43.8* | 313.2 ± 75.4 |
|  | 50 | 249.4 ± 62.4** | 263.3 ± 59.3** | 334.7 ± 72.3 |
|  | 100 | 127.8 ± 28.6** | 243.9 ± 40.5** | 298.7 ± 81.8 |
| Example 35 | 25 | 336.84 ± 57.8 | 278.8 ± 49.0* | 307.4 ± 69.8 |
|  | 50 | 310.3 ± 48.9* | 244.8 ± 39.6* | 308.1 ± 954 |
|  | 100 | 266.8 ± 50.1** | 219.6 ± 47.7** | 321.5 ± 72.9 |
| Example 36 | 25 | 321.4 ± 53.4 | 310.8 ± 51.5* | 300.2 ± 79.6 |
|  | 50 | 289.9 ± 44.8* | 258.2 ± 43.6** | 311.5 ± 98.3 |
|  | 100 | 288.3 ± 50.4** | 235.8 ± 49.8** | 322.6 ± 76.8 |
| Example 37 | 25 | 321.4 ± 62.4 | 288.0 ± 38.9* | 335.3 ± 65.2 |
|  | 50 | 279.7 ± 46.3* | 259.5 ± 46.5* | 333.8 ± 87.8 |
|  | 100 | 277.3 ± 45.7** | 222.8 ± 43.2** | 317.8 ± 62.3 |
| Example 38 | 25 | 312.9 ± 40.6* | 296.2 ± 34.6* | 268.9 ± 82.8 |
|  | 50 | 259.2 ± 54.6** | 257.1 ± 57.2** | 279.7 ± 76.5 |
|  | 100 | 182.7 ± 41.3*** | 165.4 ± 56.2*** | 324.7 ± 80.9 |
| Example 39 | 25 | 277.8 ± 50.4* | 287.3 ± 41.9* | 305.8 ± 76.4 |
|  | 50 | 184.1 ± 49.2*** | 191.7 ± 55.3*** | 298.6 ± 92.3 |
|  | 100 | 119.6 ± 50.3*** | 144.3 ± 51.2*** | 305.2 ± 89.2 |
| Example 40 | 25 | 291.4 ± 51.5* | 276.0 ± 48.7* | 311.2 ± 79.9 |
|  | 50 | 245.7 ± 44.5** | 223.6 ± 43.8** | 288.9 ± 68.9 |
|  | 100 | 145.7 ± 39.8*** | 169.8 ± 40.5*** | 301.5 ± 91.8 |
|  | 25 | 285.2 ± 44.1* | 266.0 ± 40.6** | 307.2 ± 69.7 |

TABLE 7-continued influence on the autonomic activities of mice of compounds in embodiments of the present invention ($\bar{x} \pm s$, n = 10)

| Group | Dosage (mg/kg) | Times of activities in 1 h after drug administration/10 min | Times of activities in 2 h after drug administration/10 min | Times of activities in 24 h after drug administration/10 min |
|---|---|---|---|---|
| Example 41 | 50 | 260.4 ± 37.9** | 245.5 ± 28.1** | 306.2 ± 81.3 |
|  | 100 | 198.6 ± 58.8*** | 171.5 ± 56.7*** | 291.5 ± 70.0 |
|  | 25 | 231.2 ± 47.3** | 233.2 ± 35.1** | 313.5 ± 68.2 |
| Example 42 | 50 | 154.5 ± 43.2*** | 145.3 ± 41.3*** | 310.3 ± 62.5 |
|  | 100 | 108.5 ± 48.5*** | 104.3 ± 42.5*** | 302.6 ± 69.3 |
|  | 25 | 293.7 ± 41.4* | 306.3 ± 51.6 | 324.7 ± 71.3 |
| Example 43 | 50 | 254.1 ± 42.7** | 252.6 ± 41.6** | 313.7 ± 68.5 |
|  | 100 | 265.4 ± 49.2** | 258.1 ± 32.7** | 294.1 ± 72.3 |
|  | 25 | 220.8 ± 54.6** | 228.7 ± 43.3** | 311.6 ± 60.1 |
| Example 44 | 50 | 143.4 ± 41.3*** | 133.5 ± 38.3*** | 315.1 ± 85.5 |
|  | 100 | 103.4 ± 43.5*** | 101.7 ± 45.1*** | 303.8 ± 81.2 |
|  | 25 | 235.6 ± 44.5** | 223.2 ± 41.4** | 299.2 ± 61.3 |
| Example 45 | 50 | 136.6 ± 40.5*** | 123.3 ± 47.6*** | 291.5 ± 60.4 |
|  | 100 | 112.5 ± 35.4*** | 105.6 ± 48.5*** | 288.8 ± 69.5 |
|  | 25 | 300.8 ± 49.2* | 299.2 ± 38.9* | 275.4 ± 81.3 |
| Example 46 | 50 | 264.4 ± 41.3** | 254.1 ± 53.2** | 284.7 ± 78.7 |
|  | 100 | 176.8 ± 43.2*** | 163.4 ± 36.5*** | 294.4 ± 67.5 |
|  | 25 | 328.6 ± 49.7 | 312.7 ± 56.1 | 315.1 ± 85.4 |
| Example 47 | 50 | 280.7 ± 61.3* | 278.6 ± 47.5* | 310.5 ± 75.3 |
|  | 100 | 237.2 ± 35.6** | 250.3 ± 46.2** | 307.1 ± 82.3 |
|  | 25 | 225.6 ± 43.2** | 229.4 ± 53.7** | 308.5 ± 75.2 |
| Example 48 | 50 | 145.1 ± 41.6*** | 140.6 ± 40.8*** | 317.4 ± 95.6 |
|  | 100 | 120.3 ± 48.3*** | 118.5 ± 42.6*** | 302.1 ± 89.0 |
| Example 49 | 25 | 305.2 ± 78.7* | 299.8 ± 94.1* | 281.4 ± 94.3 |
|  | 50 | 267.9 ± 21.5** | 246.6 ± 13.9** | 274.2 ± 34.8 |
|  | 100 | 179.9 ± 35.9*** | 170.5 ± 34.1*** | 286.1 ± 12.7 |
|  | 25 | 319.2 ± 55.4 | 290.6 ± 41.2* | 303.2 ± 78.6 |
| Example 50 | 50 | 297.5 ± 42.5* | 253.5 ± 40.4** | 304.7 ± 92.8 |
|  | 100 | 279.4 ± 48.3* | 224.7 ± 46.3** | 312.4 ± 79.1 |
|  | 25 | 227.8 ± 75.6** | 231.8 ± 79.8** | 321.6 ± 70.7 |
| Example 51 | 50 | 143.3 ± 64.7*** | 130.7 ± 63.2*** | 306.3 ± 68.2 |
|  | 100 | 115.8 ± 34.4*** | 108.8 ± 39.4*** | 300.4 ± 77.5 |
|  | 25 | 300.5 ± 71.3* | 280.7 ± 76.4* | 320.3 ± 65.5 |
| Example 52 | 50 | 246.2 ± 62.2** | 233.5 ± 61.3** | 299.6 ± 80.3 |
|  | 100 | 198.7 ± 34.0*** | 191.7 ± 39.6*** | 287.5 ± 90.2 |
|  | 25 | 303.8 ± 67.4* | 283.8 ± 73.8* | 314.9 ± 68.9 |
| Example 53 | 50 | 249.3 ± 61.0** | 236.7 ± 60.8** | 297.7 ± 87.6 |
|  | 100 | 201.8 ± 36.6*** | 194.8 ± 42.5*** | 330.9 ± 73.6 |
|  | 25 | 307.3 ± 65.2* | 287.3 ± 72.9* | 331.2 ± 67.4 |
| Example 54 | 50 | 252.8 ± 62.1** | 240.2 ± 62.6** | 320.7 ± 75.1 |
|  | 100 | 205.3 ± 42.8*** | 198.3 ± 48.5*** | 315.3 ± 79.2 |
|  | 25 | 232.5 ± 66.1** | 229.8 ± 75.0** | 295.2 ± 89.3 |
| Example 55 | 50 | 138.3 ± 67.6*** | 135.6 ± 69.2*** | 297.5 ± 81.0 |
|  | 100 | 110.8 ± 55.7*** | 103.8 ± 60.9*** | 289.8 ± 89.7 |
|  | 25 | 317.2 ± 70.8 | 297.4 ± 81.1 | 333.5 ± 68.2 |
| Example 56 | 50 | 262.5 ± 75.7** | 250.3 ± 78.8** | 296.1 ± 88.3 |
|  | 100 | 215.4 ± 69.9** | 208.4 ± 74.6** | 327.6 ± 66.1 |
|  | 25 | 299.9 ± 58.2* | 288.1 ± 73.0* | 311.7 ± 81.2 |
| Example 57 | 50 | 245.4 ± 45.9** | 240.8 ± 63.24** | 315.9 ± 85.6 |
|  | 100 | 206.6 ± 44.2*** | 199.6 ± 49.9*** | 325.7 ± 82.6 |
|  | 25 | 298.2 ± 57.7* | 288.7 ± 73.1* | 301.7 ± 93.5 |
| Example 58 | 50 | 244.1 ± 45.3** | 241.5 ± 63.9** | 318.5 ± 92.3 |
|  | 100 | 206.6 ± 45.8*** | 199.7 ± 51.3*** | 307.1 ± 88.7 |
|  | 25 | 280.4 ± 62.8** | 277.8 ± 79.8* | 296.4 ± 92.8 |
| Example 59 | 50 | 234.1 ± 45.3** | 230.7 ± 63.2** | 297.9 ± 86.8 |
|  | 100 | 195.8 ± 34.4*** | 188.8 ± 39.4*** | 305.9 ± 77.7 |
|  | 25 | 243.8 ± 73.8** | 238.9 ± 78.3** | 340.4 ± 76.8 |
| Example 60 | 50 | 143.3 ± 64.7*** | 131.8 ± 62.3*** | 327.6 ± 75.3 |
|  | 100 | 116.9 ± 33.8*** | 109.9 ± 39.2*** | 293.4 ± 84.9 |
|  | 25 | 317.3 ± 50.1 | 289.4 ± 40.2* | 301.9 ± 77.5 |
| Example 61 | 50 | 295.1 ± 41.9* | 250.7 ± 42.8** | 300.2 ± 91.3 |
|  | 100 | 287.1 ± 45.9** | 221.5 ± 45.8** | 317.9 ± 80.3 |
| Example 62 | 25 | 279.2 ± 45.4* | 264.9 ± 44.7* | 309.0 ± 81.9 |
|  | 50 | 237.4 ± 41.9** | 242.6 ± 49.2** | 297.2 ± 69.5 |
|  | 100 | 125.6 ± 32.8** | 170.2 ± 35.2** | 279.4 ± 86.3 |
|  | 25 | 250.6 ± 35.5** | 239.4 ± 34.6** | 269.5 ± 79.5 |
| Example 63 | 50 | 168.5 ± 53.0*** | 151.3 ± 57.0*** | 283.8 ± 79.3 |
|  | 100 | 124.5 ± 42.0*** | 117.3 ± 54.8*** | 320.3 ± 76.0 |
|  | 25 | 323.9 ± 45.4 | 310.9 ± 55.9 | 331.3 ± 94.5 |
| Example 64 | 50 | 283.8 ± 60.4* | 269.7 ± 44.6* | 313.6 ± 93.1 |
|  | 100 | 239.4 ± 35.6** | 248.2 ± 44.7** | 300.1 ± 81.3 |
|  | 25 | 280.5 ± 47.4* | 279.4 ± 43.5* | 291.2 ± 83.6 |
| Example 65 | 50 | 174.3 ± 49.2*** | 185.5 ± 56.6*** | 289.0 ± 89.4 |
|  | 100 | 127.5 ± 36.5*** | 132.6 ± 44.6*** | 280.7 ± 92.3 |
|  | 25 | 307.7 ± 54.6 | 281.3 ± 31.2* | 314.7 ± 66.7 |
| Example 66 | 50 | 275.8 ± 44.3* | 270.7 ± 46.3** | 314.1 ± 81.4 |
|  | 100 | 258.4 ± 40.3** | 243.9 ± 41.2** | 334.7 ± 62.9 |
|  | 25 | 287.7 ± 45.4* | 312.5 ± 54.8 | 307.4 ± 77.0 |
| Example 67 | 50 | 247.2 ± 44.5** | 251.3 ± 38.8** | 314.6 ± 94.9 |
|  | 100 | 223.4 ± 46.5** | 243.7 ± 40.6** | 301.9 ± 88.6 |
|  | 25 | 287.3 ± 47.9* | 267.7 ± 40.4* | 322.9 ± 76.0 |
| Example 68 | 50 | 248.2 ± 57.4** | 243.2 ± 54.6** | 319.6 ± 75.9 |
|  | 100 | 128.2 ± 30.9** | 241.7 ± 40.9** | 298.1 ± 80.2 |
|  | 25 | 322.3 ± 51.3 | 278.3 ± 40.3* | 299.1 ± 80.7 |
| Example 69 | 50 | 298.0 ± 41.5* | 251.7 ± 39.4* | 309.1 ± 91.0 |
|  | 100 | 289.3 ± 50.7** | 235.8 ± 47.4** | 320.4 ± 80.4 |
|  | 25 | 233.5 ± 58.2** | 227.8 ± 32.9** | 316.0 ± 66.9 |
| Example 70 | 50 | 159.9 ± 45.0*** | 141.0 ± 46.3*** | 320.9 ± 81.4 |
|  | 100 | 129.3 ± 41.3*** | 117.8 ± 39.6*** | 320.7 ± 60.9 |
|  | 25 | 301.5 ± 58.2 | 267.8 ± 32.9* | 318.0 ± 66.9 |
| Example 71 | 50 | 278.9 ± 45.0* | 263.0 ± 46.3** | 322.9 ± 81.4 |
|  | 100 | 249.3 ± 41.3** | 245.8 ± 39.6** | 325.7 ± 60.9 |

Compared with the control group, *P < 0.05, P < 0.01, *P < 0.001.

2.3 Influence on Hypnosis Effect with Mice Pentobarbital Sodium Doses Below the Threshold The drug was intragastric administered in mice for single time. In 60 min after drug administration, the animals were intraperitoneally injected sodium pentobarbital 25 mg/kg, and were observed of sleep condition in 30 min. Compared with the control group, incidence of sleep of low dose group, middle dose group and high dose group of drug administration were increased at different level (P<0.05~P<0.001). It suggested synergistically hypnotic effect below the threshold dose of sodium pentobarbital, the results is shown in Table 8. Table 8 shows test result of influence on the hypnotic effect with mice pentobarbital sodium doses below the threshold of compounds of Examples 1 to 71 in embodiments of the present invention.

TABLE 8 influence result on the hypnotic effect with mice pentobarbital sodium doses below the threshold of compounds in embodiments of the present invention ($\bar{x} \pm s$, n = 10)

| Group | dosage (mg/kg) | Number of sleeping animals | rate of sleeping (%) | P |
|---|---|---|---|---|
| Control group | 0 | 0 | 0 | — |
|  | 25 | 5 | 50** | 0.0098 |
| Example 1 | 50 | 7 | 70** | 0.0010 |
|  | 100 | 100 | 100*** | 0.0000 |
|  | 25 | 5 | 50** | 0.0098 |
| Example 2 | 50 | 6 | 60** | 0.0034 |
|  | 100 | 7 | 70** | 0.0010 |
|  | 25 | 3 | 30 | 0.0603 |

TABLE 8-continued influence result on the hypnotic effect with mice pentobarbital sodium doses below the threshold of compounds in embodiments of the present invention ($\bar{x} \pm s$, n = 10)

| Group | dosage (mg/kg) | Number of sleeping animals | rate of sleeping (%) | P |
|---|---|---|---|---|
| Example 3 | 50 | 4 | 40* | 0.0253 |
|  | 100 | 6 | 60** | 0.0034 |
|  | 25 | 6 | 60** | 0.0034 |
| Example 4 | 50 | 7 | 70** | 0.0010 |
|  | 100 | 8 | 80*** | 0.0002 |
|  | 25 | 6 | 60** | 0.0034 |
| Example 5 | 50 | 8 | 80*** | 0.0002 |
|  | 100 | 9 | 90*** | 0.0000 |
|  | 25 | 3 | 30 | 0.0603 |
| Example 6 | 50 | 5 | 50** | 0.0098 |
|  | 100 | 6 | 60** | 0.0034 |
|  | 25 | 5 | 50** | 0.0098 |
| Example 7 | 50 | 6 | 60** | 0.0034 |
|  | 100 | 9 | 90*** | 0.0000 |
|  | 25 | 5 | 50** | 0.0098 |
| Example 8 | 50 | 6 | 60** | 0.0034 |
|  | 100 | 8 | 80*** | 0.0002 |
|  | 25 | 6 | 60** | 0.0034 |
| Example 9 | 50 | 7 | 70** | 0.0010 |
|  | 100 | 8 | 80*** | 0.0002 |
|  | 25 | 2 | 20 | 0.1360 |
| Example 10 | 50 | 5 | 50** | 0.0098 |
|  | 100 | 6 | 60** | 0.0034 |
|  | 25 | 5 | 50** | 0.0098 |
| Example 11 | 50 | 6 | 60** | 0.0034 |
|  | 100 | 8 | 80*** | 0.0002 |
|  | 25 | 5 | 50** | 0.0098 |
| Example 12 | 50 | 8 | 80*** | 0.0002 |
|  | 100 | 8 | 80*** | 0.0000 |
|  | 25 | 4 | 40* | 0.0253 |
| Example 13 | 50 | 6 | 60** | 0.0034 |
|  | 100 | 7 | 70** | 0.0010 |
|  | 25 | 4 | 40* | 0.025 |
| Example 14 | 50 | 6 | 60** | 0.0034 |
|  | 100 | 7 | 70** | 0.0010 |
|  | 25 | 3 | 30 | 0.0603 |
| Example 15 | 50 | 6 | 60** | 0.0034 |
|  | 100 | 8 | 80*** | 0.0002 |
|  | 25 | 2 | 20 | 0.1360 |
| Example 16 | 50 | 4 | 40* | 0.0253 |
|  | 100 | 6 | 60** | 0.0034 |
|  | 25 | 3 | 30 | 0.0603 |
| Example 17 | 50 | 6 | 60** | 0.0034 |
|  | 100 | 7 | 70** | 0.0010 |
|  | 25 | 5 | 50** | 0.0098 |
| Example 18 | 50 | 6 | 60** | 0.0034 |
|  | 100 | 8 | 80*** | 0.0002 |
|  | 25 | 3 | 30 | 0.0603 |
| Example 19 | 50 | 6 | 60** | 0.0034 |
|  | 100 | 7 | 70** | 0.0010 |
| Example 20 | 25 | 4 | 40* | 0.0253 |
|  | 50 | 6 | 60** | 0.0034 |
|  | 100 | 6 | 60** | 0.0034 |
|  | 25 | 6 | 60** | 0.0034 |
| Example 21 | 50 | 7 | 70** | 0.0010 |
|  | 100 | 8 | 80*** | 0.0002 |
|  | 25 | 6 | 60** | 0.0034 |
| Example 22 | 50 | 7 | 70** | 0.0010 |
|  | 100 | 9 | 90*** | 0.0000 |
|  | 25 | 3 | 30 | 0.0603 |
| Example 23 | 50 | 4 | 40* | 0.0253 |
|  | 100 | 7 | 70** | 0.0010 |
|  | 25 | 5 | 50** | 0.0098 |
| Example 24 | 50 | 6 | 60** | 0.0034 |
|  | 100 | 9 | 90*** | 0.0000 |
|  | 25 | 4 | 40* | 0.025 |
| Example 25 | 50 | 7 | 70** | 0.0010 |
|  | 100 | 7 | 70** | 0.0010 |
|  | 25 | 4 | 40* | 0.0253 |
| Example 26 | 50 | 5 | 50** | 0.0098 |
|  | 100 | 7 | 70** | 0.0010 |
|  | 25 | 5 | 50** | 0.0098 |
| Example 27 | 50 | 6 | 60** | 0.0034 |
|  | 100 | 7 | 70** | 0.0010 |
|  | 25 | 3 | 30 | 0.0603 |
| Example 28 | 50 | 5 | 50** | 0.0098 |
|  | 100 | 6 | 60** | 0.0034 |
|  | 25 | 2 | 20 | 0.1360 |
| Example 29 | 50 | 4 | 40* | 0.0253 |
|  | 100 | 6 | 60** | 0.0034 |
|  | 25 | 5 | 50** | 0.0098 |
| Example 30 | 50 | 6 | 60** | 0.0034 |
|  | 100 | 8 | 80*** | 0.0002 |
|  | 25 | 5 | 50** | 0.0098 |
| Example 31 | 50 | 6 | 60** | 0.0034 |
|  | 100 | 8 | 80*** | 0.0002 |
|  | 25 | 3 | 30 | 0.0603 |
| Example 32 | 50 | 5 | 50** | 0.0098 |
|  | 100 | 6 | 60** | 0.0034 |
|  | 25 | 5 | 50** | 0.0098 |
| Example 33 | 50 | 6 | 60** | 0.0034 |
|  | 100 | 7 | 70*** | 0.0010 |
|  | 25 | 2 | 20 | 0.1360 |
| Example 34 | 50 | 4 | 40* | 0.0253 |
|  | 100 | 6 | 60** | 0.0034 |
|  | 25 | 4 | 40* | 0.0253 |
| Example 35 | 50 | 6 | 60** | 0.0034 |
|  | 100 | 7 | 70** | 0.0010 |
|  | 25 | 3 | 30 | 0.0603 |
| Example 36 | 50 | 4 | 40* | 0.0253 |
|  | 100 | 6 | 60** | 0.0034 |
|  | 25 | 3 | 30 | 0.0603 |
| Example 37 | 50 | 6 | 60** | 0.0034 |
|  | 100 | 7 | 70** | 0.0010 |
|  | 25 | 6 | 60** | 0.0034 |
| Example 38 | 50 | 8 | 80*** | 0.0002 |
|  | 100 | 9 | 90*** | 0.0000 |
|  | 25 | 5 | 50** | 0.0098 |
| Example 39 | 50 | 6 | 60** | 0.0034 |
|  | 100 | 7 | 70** | 0.0010 |
|  | 25 | 4 | 40* | 0.025 |
| Example 40 | 50 | 6 | 60** | 0.0034 |
|  | 100 | 7 | 70** | 0.0010 |
|  | 25 | 4 | 40* | 0.025 |
| Example 41 | 50 | 6 | 60** | 0.0034 |
|  | 100 | 8 | 80*** | 0.0002 |
|  | 25 | 5 | 50** | 0.0098 |
| Example 42 | 50 | 8 | 80*** | 0.0002 |
|  | 100 | 9 | 90*** | 0.0000 |
|  | 25 | 5 | 50** | 0.0098 |
| Example 43 | 50 | 7 | 70** | 0.0010 |
|  | 100 | 8 | 80*** | 0.0002 |
|  | 25 | 6 | 60** | 0.0034 |
| Example 44 | 50 | 7 | 70** | 0.0010 |
|  | 100 | 9 | 90*** | 0.0000 |
|  | 25 | 5 | 50** | 0.0098 |
| Example 45 | 50 | 6 | 60** | 0.0034 |
|  | 100 | 100 | 100*** | 0.0000 |
|  | 25 | 3 | 30 | 0.0603 |
| Example 46 | 50 | 6 | 60** | 0.0034 |
|  | 100 | 7 | 70** | 0.0010 |
|  | 25 | 4 | 40* | 0.025 |
| Example 47 | 50 | 7 | 70** | 0.0010 |
|  | 100 | 8 | 80*** | 0.0002 |
|  | 25 | 5 | 50** | 0.0098 |
| Example 48 | 50 | 6 | 60** | 0.0034 |
|  | 100 | 8 | 80*** | 0.0002 |
|  | 25 | 4 | 40* | 0.0253 |

TABLE 8-continued influence result on the hypnotic effect with mice pentobarbital sodium doses below the threshold of compounds in embodiments of the present invention ($\bar{x} \pm s$, n = 10)

| Group | dosage (mg/kg) | Number of sleeping animals | rate of sleeping (%) | P |
|---|---|---|---|---|
| Example 49 | 50 | 6 | 60** | 0.0034 |
| | 100 | 7 | 70** | 0.0010 |
| | 25 | 2 | 20 | 0.1360 |
| Example 50 | 50 | 4 | 40* | 0.0253 |
| | 100 | 7 | 70** | 0.0010 |
| | 25 | 6 | 60** | 0.0034 |
| Example 51 | 50 | 6 | 60** | 0.0034 |
| | 100 | 8 | 80*** | 0.0002 |
| | 25 | 2 | 20 | 0.1360 |
| Example 52 | 50 | 5 | 50** | 0.0098 |
| | 100 | 7 | 70** | 0.0010 |
| | 25 | 4 | 40* | 0.0253 |
| Example 53 | 50 | 6 | 60** | 0.0034 |
| | 100 | 7 | 70** | 0.0010 |
| | 25 | 3 | 30 | 0.0603 |
| Example 54 | 50 | 5 | 50** | 0.0098 |
| | 100 | 7 | 70** | 0.0010 |
| | 25 | 5 | 50** | 0.0098 |
| Example 55 | 50 | 6 | 60** | 0.0034 |
| | 100 | 9 | 90*** | 0.0000 |
| | 25 | 3 | 30 | 0.0603 |
| Example 56 | 50 | 5 | 50** | 0.0098 |
| | 100 | 6 | 60** | 0.0034 |
| Example 57 | 25 | 4 | 40* | 0.0253 |
| | 50 | 6 | 60** | 0.0034 |
| | 100 | 7 | 70** | 0.0010 |
| | 25 | 3 | 30 | 0.0603 |
| Example 58 | 50 | 4 | 40* | 0.0253 |
| | 100 | 6 | 60** | 0.0034 |
| | 25 | 3 | 30 | 0.0603 |
| Example 59 | 50 | 6 | 60** | 0.0034 |
| | 100 | 7 | 70** | 0.0010 |
| | 25 | 5 | 50** | 0.0098 |
| Example 60 | 50 | 6 | 60** | 0.0034 |
| | 100 | 9 | 90*** | 0.0000 |
| | 25 | 5 | 50** | 0.0098 |
| Example 61 | 50 | 6 | 60** | 0.0034 |
| | 100 | 8 | 80*** | 0.0002 |
| | 25 | 3 | 30 | 0.0603 |
| Example 62 | 50 | 4 | 40* | 0.025 |
| | 100 | 6 | 60** | 0.0034 |
| | 25 | 6 | 60** | 0.0034 |
| Example 63 | 50 | 8 | 80*** | 0.0002 |
| | 100 | 9 | 90*** | 0.0000 |
| | 25 | 4 | 40* | 0.025 |
| Example 64 | 50 | 7 | 70** | 0.0010 |
| | 100 | 8 | 80*** | 0.0002 |
| | 25 | 4 | 40* | 0.0253 |
| Example 65 | 50 | 6 | 60** | 0.0034 |
| | 100 | 7 | 70** | 0.0010 |
| | 25 | 3 | 30 | 0.0603 |
| Example 66 | 50 | 5 | 50** | 0.0098 |
| | 100 | 8 | 80*** | 0.0002 |
| | 25 | 5 | 50** | 0.0098 |
| Example 67 | 50 | 6 | 60** | 0.0034 |
| | 100 | 7 | 70** | 0.0010 |
| | 25 | 3 | 30 | 0.0603 |
| Example 68 | 50 | 4 | 40* | 0.0253 |
| | 100 | 6 | 60** | 0.0034 |
| | 25 | 3 | 30 | 0.0603 |
| Example 69 | 50 | 5 | 50* | 0.0153 |
| | 100 | 7 | 70** | 0.0010 |
| | 25 | 6 | 60** | 0.0034 |
| Example 70 | 50 | 8 | 80*** | 0.0002 |
| | 100 | 9 | 90*** | 0.0000 |
| | 25 | 3 | 30 | 0.0603 |
| Example 71 | 50 | 5 | 50* | 0.0153 |
| | 100 | 6 | 60** | 0.0034 |

Comparing with the control group: *P < 0.05, P < 0.01, *P < 0.001.

2.4 Influence on Hypnosis Effect with Mice Pentobarbital Sodium Doses at the Threshold The drug was intragastric administered in mice for single time. In 60 min after drug administration, the animals were intraperitoneally injected sodium pentobarbital 50 mg/kg. Time to fall asleep (sleep latency) and sleep duration of the animals were recorded. Compared with the control group, time to fall asleep (sleep latency) of low dose group, middle dose group and high dose group of drug administration were reduced at different level (P<0.05~P<0.001). It suggested synergistically hypnotic effect at the threshold dose of sodium pentobarbital, the results is shown in Table 9. Table 9 shows test result of influence on the hypnotic effect with mice pentobarbital sodium doses at the threshold of compounds of Examples 1 to 71 in embodiments of the present invention.

TABLE 9 influence result on the hypnotic effect with mice pentobarbital sodium doses at the threshold of compounds in embodiments of the present invention ($\bar{x} \pm s$, n = 10)

| Group | dosage (mg/kg) | time to sleep (min) | duration of sleep (min) |
|---|---|---|---|
| control group | 0 | 6.57 ± 2.14 | 25.17 ± 12.46 |
| | 25 | 3.84 ± 1.65** | 65.42 ± 27.30** |
| Example 1 | 50 | 3.54 ± 1.44** | 78.60 ± 14.67** |
| | 100 | 2.75 ± 1.62*** | 98.33 ± 21.63*** |
| Example 2 | 25 | 6.61 ± 2.22 | 35.56 ± 15.89 |
| | 50 | 4.95 ± 2.23 | 39.23 ± 23.45 |
| | 100 | 3.92 ± 1.12** | 53.55 ± 22.04** |
| | 25 | 4.41 ± 1.43* | 39.65 ± 18.32* |
| Example 3 | 50 | 3.90 ± 1.93** | 56.76 ± 24.86** |
| | 100 | 3.86 ± 1.22** | 59.76 ± 25.75** |
| | 25 | 3.75 ± 1.81** | 63.65 ± 19.54** |
| Example 4 | 50 | 3.41 ± 1.69** | 69.91 ± 19.82** |
| | 100 | 2.51 ± 1.61*** | 81.66 ± 30.31*** |
| | 25 | 3.39 ± 1.71** | 59.92 ± 17.44** |
| Example 5 | 50 | 3.26 ± 1.47** | 74.82 ± 22.78** |
| | 100 | 2.23 ± 1.19*** | 89.01 ± 18.25*** |
| | 25 | 5.51 ± 1.39 | 29.81 ± 21.65 |
| Example 6 | 50 | 4.20 ± 1.40* | 47.21 ± 22.93* |
| | 100 | 3.91 ± 2.16** | 55.33 ± 19.32** |
| | 25 | 3.25 ± 1.93** | 61.21 ± 22.82** |
| Example 7 | 50 | 3.03 ± 1.41** | 79.27 ± 21.17** |
| | 100 | 2.32 ± 1.21*** | 87.43 ± 21.56*** |
| | 25 | 5.40 ± 1.83 | 21.52 ± 16.93 |
| Example 8 | 50 | 5.05 ± 1.73 | 29.13 ± 26.44 |
| | 100 | 3.21 ± 1.32** | 66.82 ± 33.63*** |
| | 25 | 3.31 ± 1.81** | 49.14 ± 16.71* |
| Example 9 | 50 | 2.91 ± 1.52** | 72.31 ± 21.42** |
| | 100 | 2.12 ± 1.12*** | 85.16 ± 21.97*** |
| | 25 | 5.42 ± 1.58 | 31.72 ± 21.73 |
| Example 10 | 50 | 3.90 ± 1.34** | 39.41 ± 21.74* |
| | 100 | 3.81 ± 1.63** | 59.21 ± 22.41** |
| | 25 | 3.42 ± 1.37** | 47.25 ± 14.42* |
| Example 11 | 50 | 3.13 ± 1.21** | 63.75 ± 20.27** |
| | 100 | 2.13 ± 1.33*** | 78.54 ± 19.27** |
| | 25 | 5.43 ± 2.05 | 22.71 ± 26.17 |
| Example 12 | 50 | 5.01 ± 2.00 | 28.68 ± 27.56 |
| | 100 | 4.25 ± 1.16* | 38.55 ± 23.27* |
| | 25 | 4.26 ± 1.23* | 39.25 ± 17.25* |
| Example 13 | 50 | 3.93 ± 1.15** | 57.33 ± 29.41** |
| | 100 | 3.83 ± 1.21** | 59.23 ± 25.36** |
| | 25 | 4.78 ± 1.81 | 34.12 ± 28.26 |
| Example 14 | 50 | 4.25 ± 1.55* | 57.34 ± 19.33** |
| | 100 | 3.93 ± 1.57** | 60.26 ± 32.36** |
| | 25 | 4.31 ± 1.65* | 39.93 ± 15.22* |
| Example 15 | 50 | 3.53 ± 1.22** | 51.53 ± 21.35** |
| | 100 | 3.29 ± 1.58** | 58.25 ± 21.48** |
| | 25 | 5.48 ± 2.25 | 25.69 ± 27.26 |
| Example 16 | 50 | 4.21 ± 1.53* | 48.11 ± 25.41* |
| | 100 | 3.86 ± 1.45** | 55.62 ± 19.72** |
| | 25 | 5.55 ± 1.45 | 32.56 ± 25.95 |

TABLE 9-continued influence result on the hypnotic effect with mice pentobarbital sodium doses at the threshold of compounds in embodiments of the present invention ($\bar{x} \pm s$, n = 10)

| Group | dosage (mg/kg) | time to sleep (min) | duration of sleep (min) |
|---|---|---|---|
| Example 17 | 50 | 3.97 ± 1.26** | 45.62 ± 21.08* |
|  | 100 | 3.96 ± 1.14** | 57.86 ± 25.22** |
|  | 25 | 5.51 ± 2.06 | 21.71 ± 22.17 |
| Example 18 | 50 | 4.21 ± 1.53* | 31.68 ± 20.56 |
|  | 100 | 3.25 ± 1.28** | 61.47 ± 35.29** |
|  | 25 | 4.95 ± 2.00 | 30.63 ± 20.25 |
| Example 19 | 50 | 4.57 ± 1.65* | 37.67 ± 13.45* |
|  | 100 | 3.94 ± 1.23** | 52.65 ± 20.15** |
|  | 25 | 4.33 ± 1.58* | 38.67 ± 21.87* |
| Example 20 | 50 | 3.36 ± 1.20** | 66.34 ± 22.15*** |
|  | 100 | 3.18 ± 1.10*** | 68.09 ± 29.56*** |
|  | 25 | 3.15 ± 1.76** | 50.52 ± 23.64** |
| Example 21 | 50 | 3.05 ± 1.44** | 69.79 ± 19.97** |
|  | 100 | 2.28 ± 1.51*** | 77.81 ± 22.58** |
|  | 25 | 4.79 ± 2.43 | 30.12 ± 20.60 |
| Example 22 | 50 | 4.68 ± 1.59* | 37.78 ± 14.02* |
|  | 100 | 3.88 ± 1.18** | 52.57 ± 20.74** |
|  | 25 | 5.35 ± 2.33 | 22.77 ± 25.89 |
| Example 23 | 50 | 5.17 ± 2.26 | 28.59 ± 26.98 |
|  | 100 | 3.14 ± 1.21*** | 64.89 ± 45.78*** |
|  | 25 | 3.53 ± 1.58* | 59.05 ± 15.88** |
| Example 24 | 50 | 3.03 ± 1.39** | 73.65 ± 22.01** |
|  | 100 | 2.31 ± 1.28*** | 78.48 ± 19.29** |
|  | 25 | 4.41 ± 1.67* | 41.02 ± 18.97* |
| Example 25 | 50 | 3.84 ± 1.31** | 62.87 ± 28.45** |
|  | 100 | 3.05 ± 1.20*** | 70.23 ± 23.65*** |
|  | 25 | 5.38 ± 2.22 | 23.01 ± 25.99 |
| Example 26 | 50 | 5.12 ± 2.32 | 28.69 ± 26.56 |
|  | 100 | 3.24 ± 1.16** | 65.28 ± 46.29*** |
|  | 25 | 4.88 ± 1.89 | 31.32 ± 22.99 |
| Example 27 | 50 | 4.15 ± 1.65* | 60.34 ± 16.90** |
|  | 100 | 3.73 ± 1.47** | 62.15 ± 33.37** |
|  | 25 | 5.48 ± 2.25 | 27.68 ± 23.55 |
| Example 28 | 50 | 4.31 ± 1.19 | 46.89 ± 23.61* |
|  | 100 | 3.93 ± 2.45** | 55.49 ± 21.02** |
|  | 25 | 4.37 ± 1.48* | 38.15 ± 15.66* |
| Example 29 | 50 | 3.86 ± 1.31** | 56.89 ± 27.32** |
|  | 100 | 3.65 ± 1.31** | 60.12 ± 25.86** |
|  | 25 | 4.37 ± 1.58* | 38.82 ± 15.41* |
| Example 30 | 50 | 3.73 ± 1.22** | 43.66 ± 21.43* |
|  | 100 | 3.25 ± 1.31** | 58.74 ± 19.57** |
| Example 31 | 25 | 5.01 ± 2.03 | 31.28 ± 23.66 |
|  | 50 | 4.45 ± 1.54* | 60.14 ± 16.90** |
|  | 100 | 3.92 ± 1.57** | 60.05 ± 33.89** |
|  | 25 | 5.38 ± 2.21 | 25.80 ± 22.64 |
| Example 32 | 50 | 4.34 ± 1.45* | 46.11 ± 24.53* |
|  | 100 | 3.86 ± 2.35** | 54.78 ± 20.89** |
|  | 25 | 4.81 ± 2.37 | 30.43 ± 22.06 |
| Example 33 | 50 | 4.62 ± 1.75* | 36.53 ± 13.21* |
|  | 100 | 3.82 ± 1.12** | 51.56 ± 20.75** |
|  | 25 | 4.39 ± 1.61* | 37.89 ± 15.21* |
| Example 34 | 50 | 3.87 ± 1.42** | 44.75 ± 21.85* |
|  | 100 | 3.45 ± 1.38** | 54.77 ± 19.67** |
|  | 25 | 4.35 ± 1.42* | 38.25 ± 15.16* |
| Example 35 | 50 | 3.88 ± 1.16** | 57.54 ± 28.39** |
|  | 100 | 3.76 ± 1.49** | 58.38 ± 26.82** |
|  | 25 | 4.21 ± 1.65* | 38.32 ± 20.03* |
| Example 36 | 50 | 3.77 ± 1.12** | 61.41 ± 26.54** |
|  | 100 | 3.09 ± 1.25** | 72.03 ± 21.92*** |
|  | 25 | 4.99 ± 1.97 | 30.27 ± 22.71 |
| Example 37 | 50 | 3.98 ± 1.46** | 40.03 ± 20.58* |
|  | 100 | 3.88 ± 1.43** | 57.51 ± 25.63** |
|  | 25 | 4.92 ± 2.48 | 29.67 ± 21.25 |
| Example 38 | 50 | 4.67 ± 1.55* | 36.68 ± 12.30* |
|  | 100 | 3.98 ± 1.27** | 52.95 ± 20.05** |
|  | 25 | 4.52 ± 1.61* | 34.33 ± 16.25* |
| Example 39 | 50 | 4.36 ± 1.22** | 56.64 ± 27.89** |
|  | 100 | 3.91 ± 1.41** | 60.02 ± 25.52** |
|  | 25 | 5.32 ± 2.47 | 21.71 ± 26.77 |
| Example 40 | 50 | 5.13 ± 2.64 | 27.68 ± 27.86 |
|  | 100 | 4.92 ± 1.26* | 61.35 ± 45.27** |
|  | 25 | 5.33 ± 2.25 | 22.16 ± 16.23 |
| Example 41 | 50 | 5.12 ± 2.09 | 28.34 ± 17.13 |
|  | 100 | 3.16 ± 1.23*** | 65.44 ± 37.54*** |
|  | 25 | 4.42 ± 1.65* | 58.90 ± 15.38* |
| Example 42 | 50 | 3.30 ± 1.32** | 69.37 ± 20.24** |
|  | 100 | 2.26 ± 1.28*** | 78.53 ± 19.87** |
|  | 25 | 4.88 ± 1.91 | 32.33 ± 23.16 |
| Example 43 | 50 | 4.19 ± 1.74* | 59.98 ± 18.43** |
|  | 100 | 3.85 ± 1.76** | 63.07 ± 33.12** |
|  | 25 | 4.43 ± 1.55* | 58.25 ± 15.16* |
| Example 44 | 50 | 3.46 ± 1.23** | 76.74 ± 25.45** |
|  | 100 | 3.05 ± 1.57** | 89.39 ± 23.44*** |
|  | 25 | 4.19 ± 1.78* | 59.67 ± 19.87* |
| Example 45 | 50 | 3.26 ± 1.24** | 66.42 ± 28.90** |
|  | 100 | 2.17 ± 1.14*** | 90.03 ± 23.72** |
|  | 25 | 5.52 ± 2.31 | 27.80 ± 23.24 |
| Example 46 | 50 | 4.22 ± 1.23* | 47.16 ± 23.51* |
|  | 100 | 3.96 ± 2.45* | 55.58 ± 20.72** |
|  | 25 | 4.45 ± 1.43* | 39.86 ± 16.75* |
| Example 47 | 50 | 3.72 ± 1.65** | 43.26 ± 20.65* |
|  | 100 | 3.18 ± 1.54*** | 59.78 ± 19.65** |
|  | 25 | 3.40 ± 1.25** | 50.55 ± 20.76* |
| Example 48 | 50 | 3.19 ± 1.21** | 67.54 ± 21.07** |
|  | 100 | 2.05 ± 1.80*** | 87.51 ± 24.93*** |
|  | 25 | 4.59 ± 1.55* | 37.90 ± 13.18* |
| Example 49 | 50 | 3.69 ± 1.32** | 40.75 ± 23.05** |
|  | 100 | 3.38 ± 1.29** | 57.65 ± 17.87** |
|  | 25 | 5.41 ± 2.17 | 22.71 ± 26.17 |
| Example 50 | 50 | 5.07 ± 2.34 | 28.68 ± 27.56 |
|  | 100 | 3.25 ± 1.16** | 65.35 ± 46.27*** |
|  | 25 | 4.61 ± 1.74* | 49.88 ± 19.09* |
| Example 51 | 50 | 3.43 ± 1.99** | 57.61 ± 14.98** |
|  | 100 | 2.71 ± 1.72** | 82.27 ± 15.68*** |
|  | 25 | 4.86 ± 1.66* | 37.31 ± 16.74* |
| Example 52 | 50 | 4.35 ± 1.90* | 45.03 ± 13.56** |
|  | 100 | 3.65 ± 1.58** | 50.53 ± 16.58*** |
|  | 25 | 4.82 ± 1.61* | 39.56 ± 20.45* |
| Example 53 | 50 | 4.31 ± 1.84* | 47.28 ± 16.84*** |
|  | 100 | 3.61 ± 1.48** | 52.86 ± 19.25** |
|  | 25 | 4.84 ± 1.64* | 35.81 ± 17.2 |
| Example 54 | 50 | 4.33 ± 1.87* | 43.53 ± 14.97** |
|  | 100 | 3.63 ± 1.54*** | 47.53 ± 15.92** |
|  | 25 | 4.03 ± 1.97* | 37.98 ± 13.71 |
| Example 55 | 50 | 3.52 ± 2.22** | 58.53 ± 11.96** |
|  | 100 | 3.21 ± 2.01** | 65.94 ± 14.95** |
|  | 25 | 4.94 ± 1.80 | 33.64 ± 15.04 |
| Example 56 | 50 | 4.43 ± 2.04* | 41.36 ± 13.84** |
|  | 100 | 3.73 ± 1.78** | 46.03 ± 16.63** |
|  | 25 | 4.61 ± 1.53* | 41.14 ± 23.51* |
| Example 57 | 50 | 4.13 ± 1.71** | 48.87 ± 19.80** |
|  | 100 | 3.43 ± 1.20** | 54.44 ± 21.81*** |
|  | 25 | 4.44 ± 1.70* | 40.56 ± 22.36* |
| Example 58 | 50 | 3.93 ± 1.81** | 48.28 ± 18.68** |
|  | 100 | 3.23 ± 1.23*** | 52.94 ± 19.06*** |
|  | 25 | 4.48 ± 1.64* | 40.06 ± 21.38* |
| Example 59 | 50 | 3.98 ± 1.77** | 47.78 ± 17.73** |
|  | 100 | 3.28 ± 1.19*** | 53.94 ± 21.24** |
| Example 60 | 25 | 4.13 ± 1.59* | 46.64 ± 22.53* |
|  | 50 | 3.62 ± 1.74** | 58.37 ± 18.85** |
|  | 100 | 2.32 ± 1.17** | 73.03 ± 19.21** |
|  | 25 | 4.42 ± 1.43* | 38.44 ± 15.12* |
| Example 61 | 50 | 3.92 ± 1.31** | 58.53 ± 27.42** |
|  | 100 | 3.79 ± 1.44** | 58.47 ± 24.40** |
|  | 25 | 4.87 ± 1.96 | 34.29 ± 22.83 |
| Example 62 | 50 | 4.21 ± 1.72* | 57.24 ± 17.30** |
|  | 100 | 3.78 ± 1.90** | 65.03 ± 32.12*** |
|  | 25 | 3.43 ± 1.46** | 47.87 ± 14.62* |
| Example 63 | 50 | 3.09 ± 1.41** | 62.64 ± 22.64** |
|  | 100 | 2.33 ± 1.27*** | 87.42 ± 18.53** |
|  | 25 | 5.87 ± 2.32 | 24.78 ± 24.51 |
| Example 64 | 50 | 4.32 ± 1.29* | 48.23 ± 24.48* |
|  | 100 | 3.87 ± 2.43** | 53.43 ± 21.81** |
|  | 25 | 5.65 ± 1.83 | 31.48 ± 22.67 |

TABLE 9-continued influence result on the hypnotic effect with mice pentobarbital sodium doses at the threshold of compounds in embodiments of the present invention ($\bar{x} \pm s$, n = 10)

| Group | dosage (mg/kg) | time to sleep (min) | duration of sleep (min) |
| --- | --- | --- | --- |
| Example 65 | 50 | 3.93 ± 1.39** | 39.63 ± 20.19* |
|  | 100 | 3.92 ± 1.40** | 57.62 ± 24.57** |
|  | 25 | 5.37 ± 2.12 | 23.81 ± 25.29 |
| Example 66 | 50 | 5.12 ± 2.65 | 27.79 ± 26.78 |
|  | 100 | 3.14 ± 1.10*** | 61.44 ± 47.33** |
|  | 25 | 4.34 ± 1.26* | 80.69 ± 20.87*** |
| Example 67 | 50 | 4.09 ± 1.45* | 48.12 ± 22.48* |
|  | 100 | 3.87 ± 2.98** | 54.43 ± 19.81** |
|  | 25 | 5.36 ± 2.23 | 20.69 ± 25.22 |
| Example 68 | 50 | 5.09 ± 2.44 | 29.78 ± 28.77 |
|  | 100 | 3.31 ± 1.14** | 64.55 ± 47.91*** |
|  | 25 | 4.98 ± 1.88 | 31.77 ± 22.78 |
| Example 69 | 50 | 4.27 ± 1.62* | 57.73 ± 18.49** |
|  | 100 | 3.87 ± 1.78** | 64.09 ± 31.23*** |
|  | 25 | 3.60 ± 1.69* | 47.57 ± 18.97* |
| Example 70 | 50 | 3.21 ± 1.35** | 61.38 ± 27.39** |
|  | 100 | 2.28 ± 1.13*** | 73.09 ± 25.56** |
|  | 25 | 5.55 ± 1.83 | 30.48 ± 22.67 |
| Example 71 | 50 | 3.73 ± 1.39** | 36.63 ± 20.19* |
|  | 100 | 3.82 ± 1.40** | 56.62 ± 24.57** |

Comparing with the control group, *P < 0.05, P < 0.01 and *P < 0.001

3. CONCLUSION

The flavone derivatives having a structure of Formula (I) or the flavanone derivatives having a structure of Formula (II) prepared in Examples 1-71 of embodiments of the present invention are administered intragastricly to mouse as a single dosage. It is found that within the dosage of 25~100 mg/kg, the central nervous systems of mouse are significantly inhibited, the sleep time under pentobarbital sodium, and the number of mouse increases for those receiving pentobarbital sodium doses below the threshold. Meanwhile, the above responses show a dosage dependent pattern.

On the basis of the above pharmacology experiments, the compounds of embodiments of the present invention have valuable inhibiting effect on the central nervous system, and may be used to prepare sedative or hypotonic drugs.

The uses of flavone and flavanone derivatives in embodiments of the present invention in the preparation of sedative or hypotonic drugs have been described by the examples. Obviously, those skilled in the art may amend, properly change or combine the uses of the compounds described herein to carry out embodiments of the present invention without going beyond the context, spirit and scope of embodiments of the present invention. It should be particularly highlighted that, all the replacements and changes involving similar objects are obvious to those skilled in the art, and they should be regarded as being comprised in the spirit, scope and context of embodiments of the present invention.

The invention claimed is:

1. A method for sedating or hypnotizing a patient, comprising administering a compound having a structure of Formula (I) or Formula (II), metabolite, isomers and/or pharmaceutically accepted salts thereof to the patient:

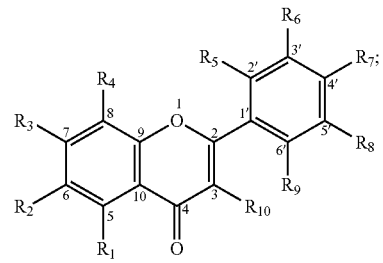

Formula (I)

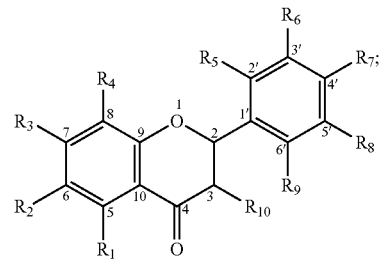

Formula (II)

wherein $R_1$, $R_2$, $R_3$, $R_4$, $R_5$, $R_6$, $R_7$, $R_8$, $R_9$ and $R_{10}$ are same or different, and they are any one independently selected from hydrogen, nitro group, halogen, cyano group, hydroxyl group, thiocyanate group, carboxyl group, amino group C1-C25 alkoxy or substituted alkoxy group, C1-C25 alkyl or substituted alkyl group, C1-C25 alkynyl or substituted alkynyl group, C1-C25 alkenyl or substituted alkenyl group, C1-C25 alkyl amide group, phenyl or substituted phenyl group, C1-C25 alkyl carbonate ester group, C1-C25 alkyl ester group, C1-C25 alkyl acyl group, C1-C25 alkyl thio-ether group, C1-C25 alkyl sulfonyl group, phenoxy or substituted phenoxy group, wherein three or more of $R_1$, $R_2$, $R_3$, $R_4$, $R_5$, $R_6$, $R_7$, $R_8$, $R_9$ and $R_{10}$ are alkoxy group.

2. The method according to claim 1, characterized in that, said compound has a structure of Formula (III) or a structure of Formula (V):

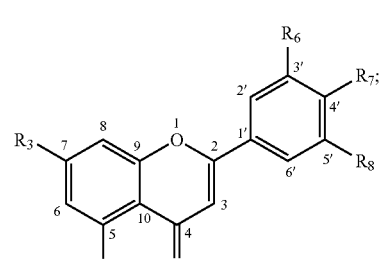

Formula (III)

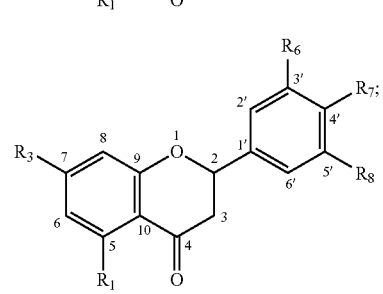

Formula (V)

wherein $R_1$, $R_3$, $R_6$, $R_7$ and $R_8$ are same or different, and they are any one independently selected from hydrogen, nitro group, halogen, cyano group, hydroxyl group, thiocyanate group, carboxyl group, amino group, C1-C25 alkoxy or substituted alkoxy group, C1-C25 alkyl or substituted alkyl group, C1-C25 alkynyl or substituted alkynyl group, C1-C25 alkenyl or substituted alkenyl group, C1-C25 alkyl amide group, phenyl or substituted phenyl group, C1-C25 alkyl carbonate ester group, C1-C25 alkyl ester group, C1-C25 alkyl acyl group, C1-C25 alkyl thioether group, C1-C25 alkyl sulfonyl group, phenoxy or substituted phenoxy group.

3. The method according to claim 1, characterized in that, said compound has a structure of Formula (IV) or a structure of Formula (VI):

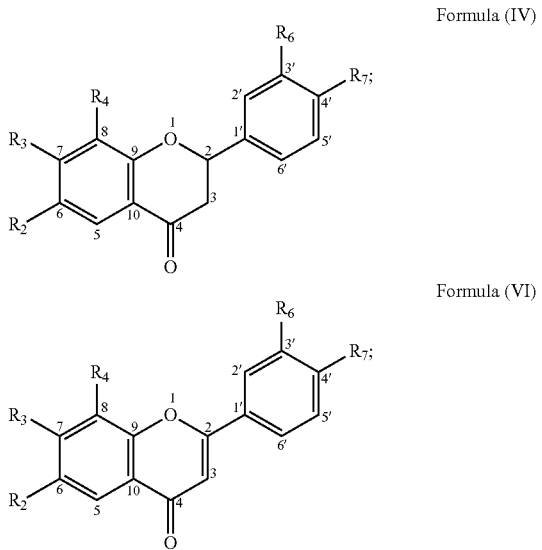

Formula (IV)

Formula (VI)

wherein $R_2$, $R_3$, $R_4$, $R_6$ and $R_7$ are same or different, and are independently selected from hydrogen, nitro group, halogen, cyano group, hydroxyl group, thiocyanate group, carboxyl group, amino group, C1-C25 alkoxy or substituted alkoxy group, C1-C25 alkyl or substituted alkyl group, C1-C25 alkynyl or substituted alkynyl group, C1-C25 alkenyl or substituted alkenyl group, C1-C25 alkyl amide group, phenyl or substituted phenyl group, C1-C25 alkyl carbonate ester group, C1-C25 alkyl ester group, C1-C25 alkyl acyl group, C1-C25 alkyl thioether group, C1-C25 alkyl sulfonyl group, phenoxy or substituted phenoxy group.

4. The method according to claim 1, characterized in that, said compound has a structure of Formula (VII):

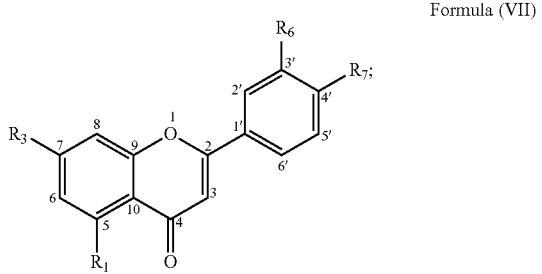

Formula (VII)

wherein $R_1$, $R_3$, $R_6$ and $R_7$ are same or different, and are independently selected from hydrogen, nitro group, halogen, cyano group, hydroxyl group, thiocyanate group, carboxyl group, amino group, C1-C25 alkoxy or substituted alkoxy group, C1-C25 alkyl or substituted alkyl group, C1-C25 alkynyl or substituted alkynyl group, C1-C25 alkenyl or substituted alkenyl group, C1-C25 alkyl amide group, phenyl or substituted phenyl group, C1-C25 alkyl carbonate ester group, C1-C25 alkyl ester group, C1-C25 alkyl acyl group, C1-C25 alkyl thioether group, C1-C25 alkyl sulfonyl group, phenoxy or substituted phenoxy group.

5. The method according to claim 1, characterized in that, the pharmaceutically acceptable salts are sodium salts, calcium salts, or potassium salts.

6. The method according to claim 1, characterized in that, at least two of $R_1$, $R_2$, $R_3$, $R_4$, $R_5$, $R_6$, $R_7$, $R_8$, $R_9$ and $R_{10}$ are not hydrogen.

7. The method according to claim 1, characterized in that, three or more of $R_1$, $R_2$, $R_3$, $R_4$, $R_5$, $R_6$, $R_7$, $R_8$, $R_9$ and $R_{10}$ are methoxy group.

8. The method according to claim 1, characterized in that, the compounds are particularly selected from the following compounds: 5,7,3',4',5'-penta methoxyl-flavone, 6,7,8,3',4'-penta methoxyl-flavanone, 5-hydroxyl-6,7,8,3',4'-penta methoxyl-flavone, 5,7,3',4'-tetramethoxyl-flavone, 5,7,3',4',5'-penta methoxyl-flavanone, 3,5,7,8,3',4',5',6'-octamethoxyl-flavone, 3,5,6,7,8,3',4',5'-octamethoxyl-flavone, 3,5,6,7,8,3',4'-heptamethoxyl-flavone, 3,5,6,7,3',4',5'-heptamethoxyl-flavone, 3,5,7,8,3',4',5'-heptamethoxyl-flavone, 5,6,7,8,3',4'-hexamethoxyl-flavone, 1,5,6,7,3',4'-hexamethoxyl-flavone, 1,5,7,8,3',4'-hexamethoxyl-flavone, 3,5,6,7,3',4'-hexamethoxyl-flavone, 5,7,8,3',4',5'-hexamethoxyl-flavone, 6,7,8,3',4',5'-hexamethoxyl-flavone, 5-hydroxyl-3,6,7,8,3',4'-hexamethoxyl-flavone, 3-hydroxyl-5,6,7,8,3',4'-hexamethoxyl-flavone, 7-hydroxyl-3,5,6,8,3',4'-hexamethoxyl-flavone, 4'-hydroxyl-3,5,6,7,3',5'-hexamethoxyl-flavone, 5-hydroxyl-6,7,8,3',4',5'-hexamethoxyl-flavone, 2'-hydroxyl-3,4,3',4',5',6'-hexamethoxyl-flavone, 5,6,7,3',4'-penta methoxyl-flavone, 5,7,8,3',4'-penta methoxyl-flavone, 5,6,7,8,4'-penta methoxyl-flavone, 6,7,8,3',4'-penta methoxyl-flavone, 7-hydroxyl-3,5,6,3',4'-penta methoxyl-flavone, 5-hydroxyl-3,7,8,3',4'-penta methoxyl-flavone, 5-hydroxyl-6,7,3',4',5'-penta methoxyl-flavone, 3-hydroxyl-5,7,3',4',5'-penta methoxyl-flavone, 2'-hydroxyl-4',5',6',3,4-penta methoxyl-flavone, 5,3'-dihydroxyl-6,7,8,4',5'-penta methoxyl-flavone, 5,6,7,4'-tetramethoxyl-flavone, 5,7,8,4'-tetramethoxyl-flavone, 5-hydroxyl-3,7,3',4'-tetramethoxyl-flavone, 5-hydroxyl-6,7,8,4'-tetramethoxyl-flavone, 3-hydroxyl-5,6,7,4'-tetramethoxyl-flavone, 3-hydroxyl-5,7,8,4'-tetramethoxyl-flavone, 5,3',5'-trihydroxyl-6,7,8,4'-tetramethoxyl-flavone, 5,3'-dihydroxyl-6,7,4',5'-tetramethoxyl-flavone, 5,7,4'-trimethoxyl-flavone, 5-hydroxyl-6,7,4'-trimethoxyl-flavone, 7-hydroxyl-5,3',4'-trimethoxyl-flavone, 3'-hydroxyl-5,7,4'-trimethoxyl-flavone, 5,7,4'-trihydroxyl-6,8,3'-trimethoxyl-flavone, 5,3',5'-trihydroxyl-6,7,4'-trimethoxyl-flavone, 5,7,8,3',4'-penta methoxyl-flavanone, 5-hydroxyl-6,7,8,3',4'-penta methoxyl-flavanone, 5,6,7,4'-tetramethoxyl-flavanone, 5,7,2',3',4',5'-hexamethoxyl-flavanone, 5,7,3',4',5',6'-hexamethoxyl-flavone, 3,5,7, 3',4',5',6'-heptamethoxyl-flavone, 3-hydroxyl-5,7,2',3',4',5',6'-heptamethoxyl-flavone, 4'-hydroxyl-5,7,3',5'-tetramethoxyl-flavone, 5'-hydroxyl-5,7,3',4'-tetramethoxyl-flavone, 5-hydroxyl-7,3',4',5'-tetramethoxyl-flavone, 7-hydroxyl-5,3',4',5'-tetramethoxyl-flavone, 7-ethoxyl-5,3',4',5'-tetramethoxyl-flavone, 6,7,8,3',4',5'-hexamethoxyl-flavanone, 6,7,8,3',4',5',6'-heptamethoxyl-flavanone, 3,6,7,8,3',4',5',6'-octamethoxyl-flavanone, 3,6,7,8,3',5',6'-heptamethoxyl-flavanone, 3,6,7,8,4',5',6'-heptamethoxyl-flavanone, 3,6,7,8,3',4',6'-heptamethoxyl-flavanone, 3,6,7,8,3',4',5'-heptamethoxyl-flavanone,
5-hydroxyl-3,6,7,8,3',4',5',6'-octamethoxyl-flavanone, 6-hydroxyl-3,7,8,3',4',5',6'-heptamethoxyl-flavanone, 7-hydroxyl-3,6,8,3',4',5',6'-heptamethoxyl-flavanone, 8-hydroxyl-3,6,7,3',4',5',6'-heptamethoxyl-flavanone, 3'-hydroxyl-3,6,7,8,4',5',6'-heptamethoxyl-flavanone, 4'-hydroxyl-3,6,7,8,3',5',6'-heptamethoxyl-flavanone, 5'-hydroxyl-3,6,7,8,3',4',6'-heptamethoxyl-flavanone, 6'-hydroxyl-3,6,7,8,3',4',5'-heptamethoxyl-flavanone, 3-hydroxyl-6,7,8,3',4',5',6'-heptamethoxyl-flavanone, 5,6,4',5',6'-penta methoxyl-flavone, 5,6,4',5'-tetramethoxyl-flavone, 6-amino-7,4',5'-trimethoxyl-flavone, 3'-hydroxyl-5,7,4',5'-tetramethoxyl-flavone, 5,5'-dihydroxyl-7,8,2'-trimethoxyl-flavone, 5,3'-dihydroxyl-7,8,4'-trimethoxyl-flavone, 2'-hydroxyl-5,7,8-trimethoxyl-flavone, 6,7,8,4'-tetramethoxyl-flavone, 5,6,7,8,4'-penta methoxyl-flavone, 5-hydroxyl-7,8,2',3',4'-penta methoxyl-flavone, 5,6,7,3',4',5'-hexamethoxyl-flavone, 5,6,7,8,3',4',5'-heptamethoxyl-flavone, 5-hydroxyl-6,7,8,4'-tetramethoxyl-flavanone, 5-hydroxyl-6,7,8,3',4'-penta methoxyl-flavanone, 5,6,7,8,4'-penta methoxyl-flavanone, 5,6,7,8,3',4'-hexamethoxyl-flavanone.